United States Patent
Panitch et al.

(10) Patent No.: US 9,890,195 B2
(45) Date of Patent: *Feb. 13, 2018

(54) MK2 INHIBITOR COMPOSITIONS AND METHODS TO ENHANCE NEURITE OUTGROWTH, NEUROPROTECTION, AND NERVE REGENERATION

(75) Inventors: Alyssa Panitch, W. Lafayette, IN (US); Kevin Otto, West Lafayette, IN (US); Nnadozie Onunkwo, West Lafayette, IN (US); Andrew Woolley, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 872 days.

This patent is subject to a terminal disclaimer.

(21) Appl. No.: 12/844,815

(22) Filed: Jul. 27, 2010

(65) Prior Publication Data

US 2011/0052658 A1    Mar. 3, 2011

Related U.S. Application Data

(60) Provisional application No. 61/228,738, filed on Jul. 27, 2009.

(51) Int. Cl.
| | |
|---|---|
| C07K 7/06 | (2006.01) |
| C07K 14/00 | (2006.01) |
| A61L 15/32 | (2006.01) |
| A61K 38/16 | (2006.01) |
| A61K 38/00 | (2006.01) |
| A61K 38/04 | (2006.01) |
| C07K 7/08 | (2006.01) |
| A61L 15/44 | (2006.01) |
| A61L 27/22 | (2006.01) |
| A61L 27/54 | (2006.01) |
| A61L 29/04 | (2006.01) |
| A61L 29/16 | (2006.01) |
| A61L 31/04 | (2006.01) |
| A61L 31/16 | (2006.01) |

(52) U.S. Cl.
CPC ............ *C07K 7/08* (2013.01); *A61L 15/32* (2013.01); *A61L 15/44* (2013.01); *A61L 27/227* (2013.01); *A61L 27/54* (2013.01); *A61L 29/048* (2013.01); *A61L 29/16* (2013.01); *A61L 31/047* (2013.01); *A61L 31/16* (2013.01); *C07K 7/06* (2013.01); *C07K 14/001* (2013.01); *A61K 38/00* (2013.01); *A61L 2300/252* (2013.01); *A61L 2300/41* (2013.01); *A61L 2300/412* (2013.01); *A61L 2300/434* (2013.01); *A61L 2430/32* (2013.01)

(58) Field of Classification Search
CPC .... A61L 15/32; A61L 15/44; A61L 2300/252; A61L 2300/41; A61L 2300/412; A61L 2300/434; A61L 2430/32; A61L 29/048; A61L 29/16; A61L 31/047; A61L 31/16; C07K 14/001; C07K 7/06; C07K 7/08

See application file for complete search history.

(56) References Cited

U.S. PATENT DOCUMENTS

| | | | |
|---|---|---|---|
| 4,105,027 | A | 8/1978 | Lundquist |
| 4,192,309 | A | 3/1980 | Poulsen |
| 4,227,522 | A | 10/1980 | Carris |
| 4,627,432 | A | 12/1986 | Newell et al. |
| 4,778,054 | A | 10/1988 | Newell et al. |
| 4,811,731 | A | 3/1989 | Newell et al. |
| 5,035,237 | A | 7/1991 | Newell et al. |
| 5,175,144 | A | 12/1992 | Walser |
| 5,415,864 | A | 5/1995 | Kopecek et al. |
| 5,565,350 | A | 10/1996 | Kmiec et al. |
| 6,855,693 | B2 | 2/2005 | Mochly-Rosen et al. |
| 6,921,527 | B2 | 7/2005 | Platz et al. |
| 7,041,814 | B1 | 5/2006 | Weinstock et al. |
| 7,135,453 | B2 | 11/2006 | Brophy et al. |
| 7,361,352 | B2 | 4/2008 | Birkett et al. |
| 8,536,303 | B2 | 9/2013 | Panitch et al. |
| 8,741,849 | B2 | 6/2014 | Panitch et al. |
| 2002/0009491 | A1 | 1/2002 | Rothbard et al. |
| 2002/0041899 | A1 | 4/2002 | Chudzik et al. |
| 2002/0128444 | A1 | 9/2002 | Gingras et al. |
| 2003/0134810 | A1 | 7/2003 | Springate et al. |
| 2003/0187232 | A1 | 10/2003 | Hubbell et al. |
| 2003/0190364 | A1 | 10/2003 | Panitch et al. |
| 2005/0153372 | A1 | 7/2005 | Greengard et al. |
| 2006/0024264 | A1 | 2/2006 | Kuroda et al. |
| 2006/0035814 | A1 | 2/2006 | Brophy et al. |
| 2006/0115453 | A1 | 6/2006 | Yaffe et al. |
| 2006/0193920 | A1 | 8/2006 | Bosch et al. |
| 2006/0293234 | A1 | 12/2006 | Schroeder |
| 2007/0026518 | A1 | 2/2007 | Healy et al. |

(Continued)

FOREIGN PATENT DOCUMENTS

| | | | |
|---|---|---|---|
| CA | 2689296 | * | 2/1927 |
| CN | 1747949 | | 3/2006 |

(Continued)

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Abergel et al., "Biochemical composition of the connective tissue in keloids and analysis of collagen metabolism in keloid fibroblast cultures," J Invest Dermatol, vol. 84, pp. 384-390, May 1985.
Achari et al., 1997, J Polym Sci A: Polym Chem, 35: 2513-2520.
Allaire et al. (1997) Ann Thorac Surg 63(2):582-91.
Altschul et al., Nucleic Acids Res. 25: 3389-3402 (1997).

(Continued)

*Primary Examiner* — Chang-Yu Wang
(74) *Attorney, Agent, or Firm* — McCarter & English LLP

(57) ABSTRACT

The described invention provides compositions comprising at least one peptide of formula I for enhancing neurite outgrowth, neuroprotection, and nerve regeneration, and methods of use thereof.

29 Claims, 16 Drawing Sheets

(56) References Cited

U.S. PATENT DOCUMENTS

| | | | |
|---|---|---|---|
| 2007/0078092 A1 | 4/2007 | Livnah et al. | |
| 2007/0154448 A1 | 7/2007 | Reid et al. | |
| 2007/0202189 A1 | 8/2007 | Ahlfors | |
| 2008/0038352 A1 | 2/2008 | Simpson et al. | |
| 2008/0113971 A1 | 5/2008 | Hanau et al. | |
| 2008/0132443 A1 | 6/2008 | Brophy et al. | |
| 2008/0293640 A1 | 11/2008 | Brophy et al. | |
| 2009/0149389 A1* | 6/2009 | Panitch et al. | 514/13 |
| 2009/0176694 A1 | 7/2009 | Brophy et al. | |
| 2009/0176695 A1 | 7/2009 | Brophy et al. | |
| 2009/0179638 A1 | 7/2009 | Barker et al. | |
| 2009/0196927 A1* | 8/2009 | Panitch et al. | 424/484 |
| 2009/0258819 A1 | 10/2009 | Brophy et al. | |
| 2009/0269406 A1 | 10/2009 | Panitch et al. | |
| 2010/0004165 A1 | 1/2010 | Brophy et al. | |
| 2010/0009903 A1 | 1/2010 | Brophy et al. | |
| 2010/0098760 A1* | 4/2010 | Panitch | 424/484 |
| 2010/0158968 A1* | 6/2010 | Panitch et al. | 424/422 |
| 2011/0052658 A1 | 3/2011 | Whitekettle et al. | |
| 2011/0288036 A1 | 11/2011 | Lander et al. | |
| 2012/0263680 A1 | 10/2012 | Lander et al. | |
| 2014/0112947 A1 | 4/2014 | Panitch et al. | |

FOREIGN PATENT DOCUMENTS

| | | | |
|---|---|---|---|
| JP | 2002-505077 | 2/2002 | |
| JP | 2006-515159 | 2/2004 | |
| WO | WO 1991/16038 | 10/1991 | |
| WO | WO 1993/022443 | 11/1993 | |
| WO | WO 2002/083933 | 10/2002 | |
| WO | WO 2003/018758 | 3/2003 | |
| WO | WO 2003/076333 | 9/2003 | |
| WO | WO 2004/075914 | 9/2004 | |
| WO | WO 2004/110337 | 12/2004 | |
| WO | WO 2005/037236 | 4/2005 | |
| WO | WO 2005/114221 | 12/2005 | |
| WO | WO 2006/053315 | 5/2006 | |
| WO | WO 2006/071456 | 7/2006 | |
| WO | WO 2007/053512 | 5/2007 | |
| WO | WO 2008/008772 | 1/2008 | |
| WO | 2689296 | 7/2008 | |
| WO | WO 2008/085191 | 7/2008 | |
| WO | WO2008085191 | * 7/2008 | C07K 7/08 |
| WO | WO 2009/021137 | 2/2009 | |
| WO | WO 2009/123759 | 10/2009 | |
| WO | WO 2010/065206 | 6/2010 | |
| WO | WO 2010/068692 | 6/2010 | |
| WO | WO 2011/017132 | 2/2011 | |

OTHER PUBLICATIONS

Arnano et al., "Formation of Actin Stress Fibers and Focal Adhesions Enhanced by RhoKinase", Science, Feb. 28, 1997, vol. 275, No. 5304, 1308-1311.
Andrew et al., "Spinothalamic lamina I neurons selectively sensitive to histamine: a central neural pathway for itch," Nature Neuroscience, 2001 4(1): p. 72-77.
Andrews et al. (1993) "Report of the AVMA panel on Euthanasia," Journal of the American Veterinary Association, 202(2): 229-249.
Auwerx. "The Human Leukemia-Cell Line, Thp-1-a Multifaceted Model for the Study of Monocyte-Macrophage Differentiation," Experientia, 1991, 47, 22-31.
Bareyre et al., "Inflammation, degeneration and regeneration in the injured spinal cord: insights from DNA microarrays," Trends Neurosci, 2003, 26(10): p. 555-63.
Beutler, 1999; J. Rheurnatol., 26:16-21.
Biomol International (online), Kinase Inhibitors, 2006, retrieved from www.biomol.com/Online_Catalog/Online_Catalog/Products/36/?search=&mode=product&lastSort=&all=true&categoryId=714.
Biomol International (online), Kinases, 2006, retrieved from www.biomol.com/Online_Catalog/Online_Catalog/Products/36/?search=&mode=product&lastSort=&all=true&categoryId=713.

Brennan et al., "Cylokine Expression in Chronic Inflammatory Disease," British Medical Bulletin, 1995, 51(2), 368-384.
Brophy et al, (1998) J Reprod Fertil 114(2):351-355.
Buckenmaier, C.C., 3rd, et al., "Comparison of antiadhesive treatments using an objective rat model," Am. Surg., 1999, 65(3):274-82.
Butler et al., "Use of organotypic coculture to study keloid biology," Am J Surg, 195(2): 144-148, Feb. 2008.
Calderon et al., "Increased proliferation in keloid fibroblasts wounded in vitro," J Surg Res, vol. 61, pp. 343-347, Mar. 1996.
Carpino et al., 1972, J. Org. Chem., 37:3403-3409.
Carroll et al., "Heparin stimulates production of bFGF and TGF-beta 1 by human normal, keloid, and fetal dermal fibroblasts," Med Sci Monit, vol. 9, pp. BR97-108, Mar. 2003.
Carroll et al., "Triamcinolone stimulates bFGF production and inhibits TGF-beta 1 production by human dermal fibroblasts." Dermato Surg, vol. 28, pp. 704-709, Aug. 2002.
Chiu et al., "Photodynamic therapy on keloid fibroblasts in tissue-engineered keratinocyte-fibroblast co-culture," Lasers Surg Med, vol. 37, pp. 231-244, Sep. 2005.
Choi, et al., 2005, Angewandte Chemie, 44(41): 6685-6689.
Glaverie et al., Comput. Chem., 17:191-201 (1993).
Clowes et al. (1991) J Vasc Surg, 13(6):885-91.
Corpet, et al., Nucleic Acids Research, 16:10881-90 (1988).
Coumans et al. (2001). "Axonal regeneration and functional recovery after complete spinal cord transection in rats by delayed with transplants and neurotrophins." The Journal of Neuroscience, 21(23):9334-9344.
Dalkowski et al., "Cryotherapy modifies synthetic activity and differentiation of keloidal fibroblasts in vitro," Exp Dermatol, vol. 12, pp. 673-681, Oct. 2003.
Davies et al. (2000) Biochem J 351(Pt 1):95-105.
DeGrado et al. (1999) Annual Review of Biochemistry 68:779-819.
DeMarzo et al., "Prostate stem cell compartments: expression of the cell cycle inhibitor p27Kip1 in normal, hyperplastic, and neoplastic cells", Am. J. Pathol., Sep. 1998, vol. 153, No. 3, 911-919.
Dreiza et al., "Transducible heat shock protein 20 phosphopeptide alters cytoskeletal dynamics," FASEB J. 19:261-263; 2004.
Dreiza et al. (2005) FASEB J 19(2):261-3.
Duncan et al. (1999) FASEB J 13(13): 1774-86.
Fawell et al., Proc Natl Acad Sci USA, 1994, 91(2): 664-668.
Feldmann et al., "Role of cytokines in rheumatoid arthritis," Annual Review of Immunology, 1996, 14, 397-440.
Feldmann et al., "The role of cytokines in the pathogenesis of rheumatoid arthritis," Rheumatology, 1999, 38, 3-7.
Fields et al., 1990, Int. J. Pept. Protein Res., 35: 161-214.
Firestein et al., "How important are Y cells in chronic rheumatoid synovitis? II. T cell-independent mechanisms from beginning to end," Arthritis and Rheumatism 2002, 46, (2), 298-308.
Fisher et al., 1994, Macromol Chem Phys. 195: 679-687.
Fragonas et al., Aricular cartilage repair in rabbits by using suspensions of allogenic chondrocytes in alginate, Biomaterials, 2000, 21(8): 795-801.
Frankel et al., Cell, 55(6): 1189-1193, 1988.
Fuchs et al. (1997) J Hypertens 15(3): 301-307.
Fuchs et al. (2000) Am J Physiol Regul Integr Comp Physiol 279(2): R492-8.
Gaestel et al., "Protein kinases as small molecule inhibitor targets in inflammation," Current Medicinal Chemistry, 2007, 14 (21): 2214-2234.
Gaestel, Nat. Rev. Mol. Cell. Biol. 7, 120-130, 2006.
Gerthoffer et al. (2001) J Appl Physiol 91:963-972, 2001.
Green et al., Cell, 1988, 55(60: 1179-1188.
Gu et al., 2002, J Appl Poly Sci, 86: 3412-3419.
Haapasalo et al., "Truncated trkB, T1 is dominant negative inhibitor of trkB,TK+-mediated cell survival", Biochem Biophys Res Comun, Feb. 9, 2001, vol. 280, No. 5, 1352-1358 (Abstract only).
Hanasono et al., "Autocrine growth factor by fetal, keloid, and normal dermal fibroblasts," Arch Facial Plast Surg. vol. 5, pp. 26-30, Jan.-Feb. 2003.
Hayess et al., "Effect of protein kinase inhibitors on activity of mammalian small heat-shock protein (HSP25) kinase", *Biochemical Pharmacology*, May 9, 1997, vol. 53, No. 9, 1239-1247.

(56) References Cited

OTHER PUBLICATIONS

Hedges et al., J Biol. Chem. 274, 24211-24219, 1999.
Hegen et al., "MAPKAP kinase 2-deficient mice are resistant to collagen-induced arthritis," Journal of Immunology 2006, 177(3), 1913-1917.
Henikoff et al. (1989) Proc. Natl. Acad. Sci. USA 89:10915).
Higgins et al., CABIOS, 5:151-153 (1989).
Higgins et al., Gene, 73:237-244 (1988).
Hirano et al., Journal of Surgical Research 102, 77-84, 2002.
Ho et al., "Synthetic Protein Transduction Domains: Enhanced Transduction Potential in Vitro and in Vivo," *Cancer Research*, 2001, 61: 474-477.
Hong et al., "Growth of keloid-producing fibroblasts in commercially available serum-free media," Otolaryngol Head Neck Surg, vol. 121, pp. 469-473, Oct. 1999.
Hruby, V.J. (2002) Nat Rev Drug Discov 1(11): 847-58.
Huang, et al., Computer Applications in the Biosciences 8:155-65 (1992).
Iwasaki et al., "Effect of transformig growth factor beta 1 on spinal motor neurons after axotomy," J Neurol Sci, 1997, 147(1): 9-12.
Jaccvella, Long-lasting results with hydroxylapatide (Radiesse) facial filler, Plastic and Reconstructive Surgery, 2006, 118(3S):15S-21S.
Jenkins et al., "The pathogenesis of rheumatoid arthritis: A guide to therapy," American Journal of the Medical Sciences, 2002, 323(4), 171-180.
Jobanputra et al., Colorectal Dis. Oct. 2007: 9 Suppl 2: 54-9.
Johnson et al. (2004) Nature Biotech 22(9):1093-1094.
Karlin et al., Proc. Natl. Acad. Sci. USA 90:5873-5787 (1993).
Kent et al. (2000) Ann Vasc Surg 18(2): 135-7.
Knoepp et al. (2000) J Vasc Surg 31:343-353.
Koch et al. "Serum-free keloid fibroblast cell culture: an in vitro model for the study of aberrant wound healing," in Plast Reconstr Sur., vol. 99, 1997, pp. 1094-1098.
Koonin et al., "Origin and evolution of eukaryotic apoptosis: the bacterial connection", Cell Death Differ, Apr. 2002, vol. 9, No. 4, 394-404.
Kossi et al., "Different metabolism of hexose sugars and sucrose in wound fluid and in. fibroblast cultures derived from granulation tissue, hypertrophic scar and keloid." Pathobiology; vol. 68, pp. 29-35, Jan.-Feb. 2000.
Kotlyarov et al., "MAPKAP kinase 2 is essential for LPS-induced TNF-alpha biosysnthesis," Nature Cell Biology, 1999, 1(2):94-97.
Kumar et al., "p38 map kinases: Key signaling molecules as therapeutic targets for inflammatory diseases," Nature Reviews Drug Discovery, 2003, 2, (9), 717-726.
Kwon et al., "The cdk2 Binding Domain of p27Kip Correlates with the Inhibition of the Kinase Activity of pdk2/Cyclin Complexes", Biochem Biophys Res Comm. 1996, vol. 220, 703-709.
Langer, 1990 Science 249, 1527-1533.
Lavoie et al., J Biol. Chem. 268, 24210-24214. 1993.
Lavoie et al., Mol Cel Biol. 15: 505-516, 1995.
Liu et al., De novo design, synthesis, and characterization of antimicrobial beta-peptides, J Am Chem Soc, 2001, 123(31):7553-7559.
LoGerto et al, (1984) Arch Surg 119:1212-1214.
Lopes et al., "Inhibition of HSP27 phosphorylation by a cell-permeant MAPKAP Kinase 2 inhibitor". *Biochemical and Biophysical Research Communications*, May 8, 2009, vol. 382, No. 3, 535-539.
Macomson et al. (2002) Neurosurgery 51(1): 204-10: discussion 210-1.
Mann et al. (1999) Lancet 354(9189): 1493-8.
Manjnissen et al., Tissue-engineered cartilage using serially passaged articular chondrocytes. Chrondrocytes in alginate, combined in vivo with a synthetic (E210) or biologic degradable carrier (DBM), Biomaterials, 2000.
Matsuoka et al., "Ultrastuctural characteristics of keloid fibroblasts." Am J Dermatopathol, vol. 10, pp. 505-508, Dec. 1988.

McCormack et al., "The effect of copper tripertide and tretinoin on growth factor production in a serum-free fibroblast model." Arch Facial Plast Surg, vol. 3, pp. 28-32, Jan.-Mar. 2001.
McLemore et al. (2005) J Am Coll Surg 201(1):30-6.
Merrifield, 1963, J. Am. Chem. Soc., 85:2149-2154.
Myers et al., Computer Applic. Biol. Sci., 4:11-17 (1988).
Mosse et al. (1985) Lab Invest 53(5):556-62.
Needleman et al., J. Mol. Biol., 48: 443 (1970).
Neidigh et al, (2002) Nature Structural Biology 9(6): 425-430.
Pearson et al., Methods in Molecular Biology, 24: 307-331 (1994).
Pearson et al., Proc. Natl. Acad. Sci., 85: 2444 (1988).
Pincus et al., "What is the Natural-History of Rheumatoid-Arthritis," Rheumatic Disease Clinics of North America, 1993, 19, (1), 123-151.
Pineau et al., Proinflaminatory cytokine synthesis in the injured mouse spinal cord: mulipphasic expression pattern and identification of the cell types involved,: J Comp Neurol, 2007, 500(2): pp. 267-285.
Pinol et al., "Effect of minoxidil on DNA synthesis in cultured fibroblasts from healthy skin or keloids," Med Cutan Ibero Lat Am, vol. 18, pp. 13-17, 1990.
Podolin et al., "Altenuation of murine collagen-induced arthritis by a novel, potent, selective small molecule inhibitor of I kappa B kinase 2, TPCA-1 (2-[(aminocarbonyl)amino]-5-(4-fluorophenyl)-3-thiophenecarboxamide), occurs via reduction of proinflammatory cytokines and antigen-induced T cell proliferation," Journal of Pharmacology and Experimental Therapeutics, 2005, 312, (1). 373-381.
Polo et al., "Effect of TGF-beta2 on proliferative scar fibroblast cell kinetics," Ann Plast Surg, vol. 43, pp. 185-190, Aug. 1999.
Seal et al., Biomacromolecules, 2003,4: 1572-1582.
Sestier et al., "In vitro toxicity of magnetic fluids evaluated for macrophage cell lines," Journal of Magnetism and Magnetic Materials, 2002, 252, (1-3), 403-405.
Shi et al. (2002) Biol Chem 383:1519-1536, 2002.
Silver et al., "Regeneration beyond the glial scar," Nature Reviews Neuroscience, 2004. 5(2): p. 146-156.
Smith and Waterman, Adv. Appl. Math., 2: 482 (1981).
Sousa et al. (2007) J Cell Biochem 100(6):1581-1592.
Stokoe, Biochem. J., 1993, 296 (pt 3): 843-849.
Takemura et al., "Evaluation of a human monobytic cell line THP-1 model for assay of the intracellular activities of antimicrobial agents against Legionella pneumophlia, " Journal of Antimicrobial.
Tanaka et al., 1976, Bulletin of the Chemical Society of Japan, 49(10):2821-2823.
Tang et al., Synthesis of urea oligomers and their antibacterial activity, Chem Commun. 2005, 1537-1539.
Terashima et al. (2002) J Am Coll Cardiol 39:228A.
Tessier et al. (2004) J Vasc Surg 40(1): 106-14.
Tew et al., De novo design of biomimetic antimicrobial polymers, PNAS, 2002, 99(8): 5110-5114.
Tapash et al., Transdermal and Tropical Drug Delivery, pp. 249-297 (1997).
Tyagi et al., J Biol Chem, 2001, 276(5): 3254-3261.
Vassalli, 1992, Annu. Rev. Immunol., 10:411-452.
Verlardo et al., "Patterns of Gene Expression Reveal a Temporarally Orchestrated Wound Healing Response in the Injured Spinal Cord," J. Neurosci.: 2004, 24(39): p. 8562-8576.
Vincent et al., "Human Skin Keloid Fibroblasts Display Bioenergetics of Cancer Cells," J. Invest Dermatol. 128(3): 702-709, Mar. 2008.
Violette et al., Mimicking hetical antibacterial peptides with nonpeptidic folding oligomers, Chemistry and Biology, 2006, 13(5): 531-538.
Wang et al., "Construction of animal models of keloid by tissue engineering," Di Yi Jun Yi Da Xue Xue Bao, vol. 25, pp. 815-819, 832, Jul. 2005. (Japanese language with English Abstract provided).
Wang et al., "p27Kip1 overexpression causes apoptotic death in mammallan cells", Oncogene, Dec. 11, 1997, vol. 15, No. 24, 2991-2997.
Ward et al., "Design of a bioactive cell-penetrating peptide: when a transduction domain does more than transduce", *Journal of Peptide Science*, Oct, 2009, vol. 15, No. 10, 668-674.

(56) References Cited

OTHER PUBLICATIONS

Weibel et al., Am. J. Surg. 1973; 126: 345-53.
Woerly et al, (2001) "Spinal cord reconstruction using Neurogel™ Implants and functional recovery chronic injury," Journal of Neuroscience Research, 66: 1187-1197.
Wooten et al., Comput. Chem., 17: 149-163 (1999).
Worm et al., "Abberant p27kip1 promoter methylation in malignant melonama", Oncogene, Oct. 19, 2000, vol. 19, No. 44, 5111-5115.
Xia et al., "Increased CCN2 transcirption in keloid fibroblasts requires cooperatively beween AP-1 and SMAD binding sites." Ann Surg. vol. 246, pp. 886-895, No. 2007.
Xia et al., "P38 MAP kinase mediates transforming growth factor-beta2 transcription in human keloid fibrolasts," Am J Physiol Regul Integr Comp Physiol. vol. 290, pp. R501-R508, Mar. 2006.
Xu et al., Oncogene 25, 2987-2998, 2006.
Yamanishi et al., "Regulation of joint destruction and inflammation by p53 in collagen-induced arthritis," American Journal of Pathology 2002. 160. (1), 123-130.
Yamboliev et al., Am. J Physiol. Heart Circ Physiol., 278, H1899-1907, 2000.
Yang et al., "Establishment of an animal model of human hyperplastic scar in nude mice," Zhonghua Shao Shang Za Zhi, vol. 20, pp. 82-84. Apr. 2004. (Japanese language with English Abstract provided).
Yang et al., "Early expression and cellular localization of proinflammatory cytokines interleukin-l beta, interleukin-6, and tumor necrosis factor-alpha in human traumatic spinal cord injury," Spine, 2004.
Zong, X., et al., "Prevention of postsurgery-induced abdominal adhesions by electrospun bioabsorable nanofibrous poly(lactide-co-clucolide)-based membranes," Am. Surg., 2004, 240(5): p. 910-5.
Colomer, Sub-Cellular Biochemistry, 2007, 45: 169-214.
Barone et al., "Inhibition of p38Mitogen-Activated Protein Kinase Provides Neuroprotection in Cerebral Focal Ischemia", Med Res. Rev., 2001, vol. 21, No. 2, 129-145.
Schindler et al., Examination of the kinetic mechanism of mitogen-activated protein kinase activated protein kinase-2, Biochimica et Biophysica Acta, Jul. 29, 2002, 1598(1-2): 88-97.
Burgess et al., J of Cell Bio., 1990, 11: 2129-2138.
Bowie et al., Science, 1990, 247: 1306-1310.
Pawson et al., Science 2003, 300: 445-452.
Zhongshu Song et al., "Fusarin C biosynthesis in Fusarium moniliforme and Fusarium venenatum", Chembiochem, 2004, 5(9):1196-1203.
Morrison et al., "Combinatorial alaine-scanning," Current Opinion in Chemical Biology, 2001, 5:302-307.
Del Gaizon et al, A Novel TAT-Mitochondrial Signal Sequence Fusion Protein Is Processed, Stays in Mitochondria, and Crosses the Placenta, Molecular Therapy, 2003, 7(6):720-730.
Yu, Pey-Jen et al; "Vascular injury and modulation of MAPKs: A targeted approach to therapy of restenosis," Cell, Signai, (2007) 19 pp. 1359-1371.
Tucker, Erik I. et al: "Prevention of vascular graft occlusion and thrombus-associated thrombin generation by inhibition of factor XI," Blood (2009) 113(4)p. 936-944.

Babapulle, Mohan N. et al: "A hierarchial bayesian meta analysis of randomized clinical trials of drug eluting stents." Lancet (2004) 364 p. 583-91.
Cyrus, Tillmann et al; "Effect of low dose aspirin on vascular inflammation, plaque stability, and atherogenesis in low density lipoprotein receptor deficient mice," Circulation (2002) 106 p. 1282-1287.
Dinarello, C. A.; "The IL-1 family and inflammatory diseases." Clin. Exp. Rheumatol. (2002) 20 (suppl. 27) p. S1-S13.
Tourneau Christophe Le et al; "Dose escalation methods in phase I cancer clinical trials." J. Natl. Cancer. Inst. (2009) 101 (10) p. 708-720, publication date May 20, 2009.
Schneider et al., 1998, In Vivo Evaluation of hsp27 as an Inhibitor of Actin Polymerization: Hsp27 Limits Actin Stress Fiber and Focal Adhesion Formation After Heat Shock, Journal of Cellular Physiology, 177: 575-584.
Beck et al., 2000, Molecular chaperones in the kidney: distribution, putative roles, and regulation, Am J Physiol Renal Physiol, 279: 203-215.
Keezer et al., Andiogenesis inhibitors Target the Endothelial Cell Cystoskeleton through Altered Regulation of Heat Shock Protein 27 and Cofilin, Cancer Res. 63: 6405-6412.
Cheek S., et al., "Sequence and structure classification of kinases", J. Mol. Biol., 2002, vol. 320, pp. 855-861.
Cagnello M., et al., "Activation and function of the MAPKs and their substrates, the MAPK-activated protein kinases", Microbiology adn Molecular Biology Reviews, 2011, vol. 75, pp. 50-83.
Ward B., et al., "Design of a bioactive cell-penetrating, peptide: when a transduction domain does more than transduce", J Pept Sci., 2009, vol. 15, pp. 668-674.
Powell et al. (2003) Moelcular and Cellular Biology, 23(15) 5376-5387.
Ridley et al., "Actions of 11-1 are Selectively controlled by P38 Mitogen-Activated Protein Kinase: regulation of prostaglandin H synthase-2, Metalloproteinases, and IL-6 at different levels", *J. immunol.*, 1997, vol. 158, 3165-31373.
Ross et al., "High-content screening analysis of the p38 pathway: Profiling of structurally related p38 alpha kinase inhibitors using cell-based assays," Assay and Drug Development Technologies, 2006, 4, (4), 397-409.
Russel et al., "The effect of histamine on the growth of cultured fibroblasts isolated from normal and keloid tissue," J Cell Physiol, vol. 93, pp. 389-393, Dec. 1977.
Sahara et al., "Suppression of in vitro proliferative scar fibroblast contraction by interferon alfa-2b," Wound Repair Regen, vol. 1, pp. 22-27, Jan. 1993.
Saklatvala, "The p38 MAP kinase pathway as a therapeutic target in inflammatory disease," Current Opinion in Pharmacology, 2004, 4, (4), 372-377.
Sawhney et al., Macromolecules (1993) 26, 581-587.
Schenk et al, Signal perception and transduction: the role of protein kinases, *Biochemica et Biophyica Acta*, 1999, vol. 1449, 1-24.
Schwarze et al., Science, 1999, 285(54339: 1569-1572.

* cited by examiner

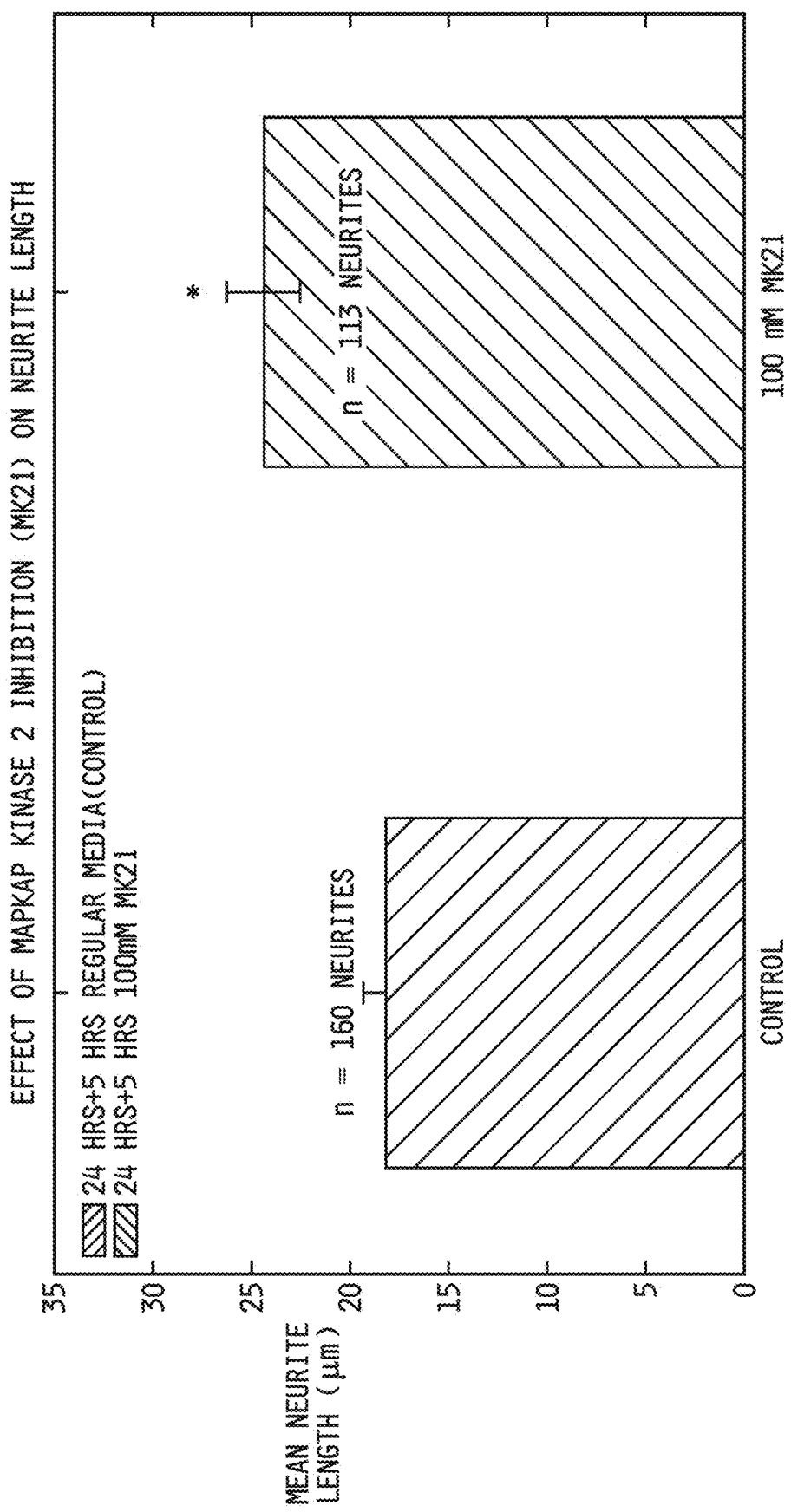

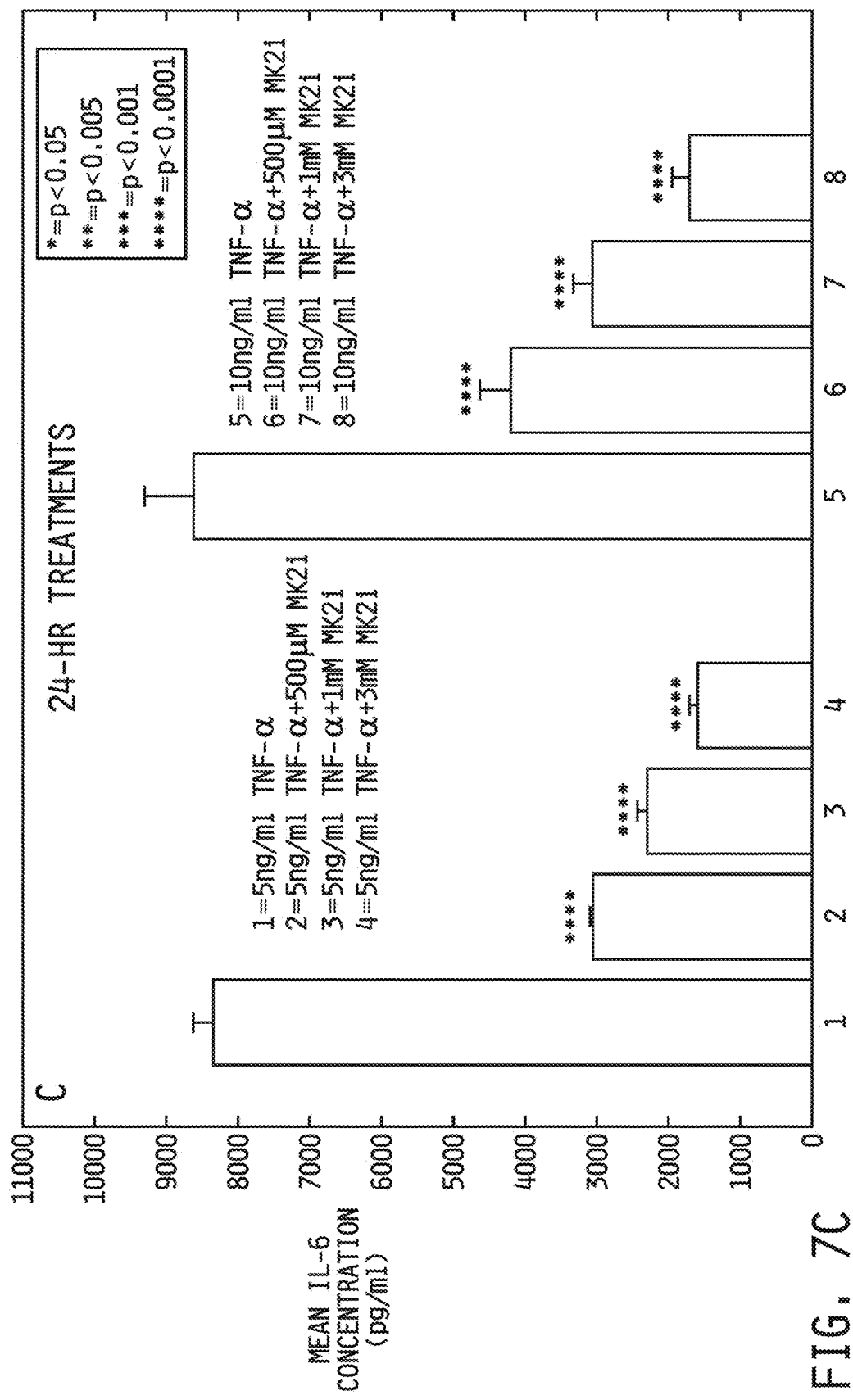

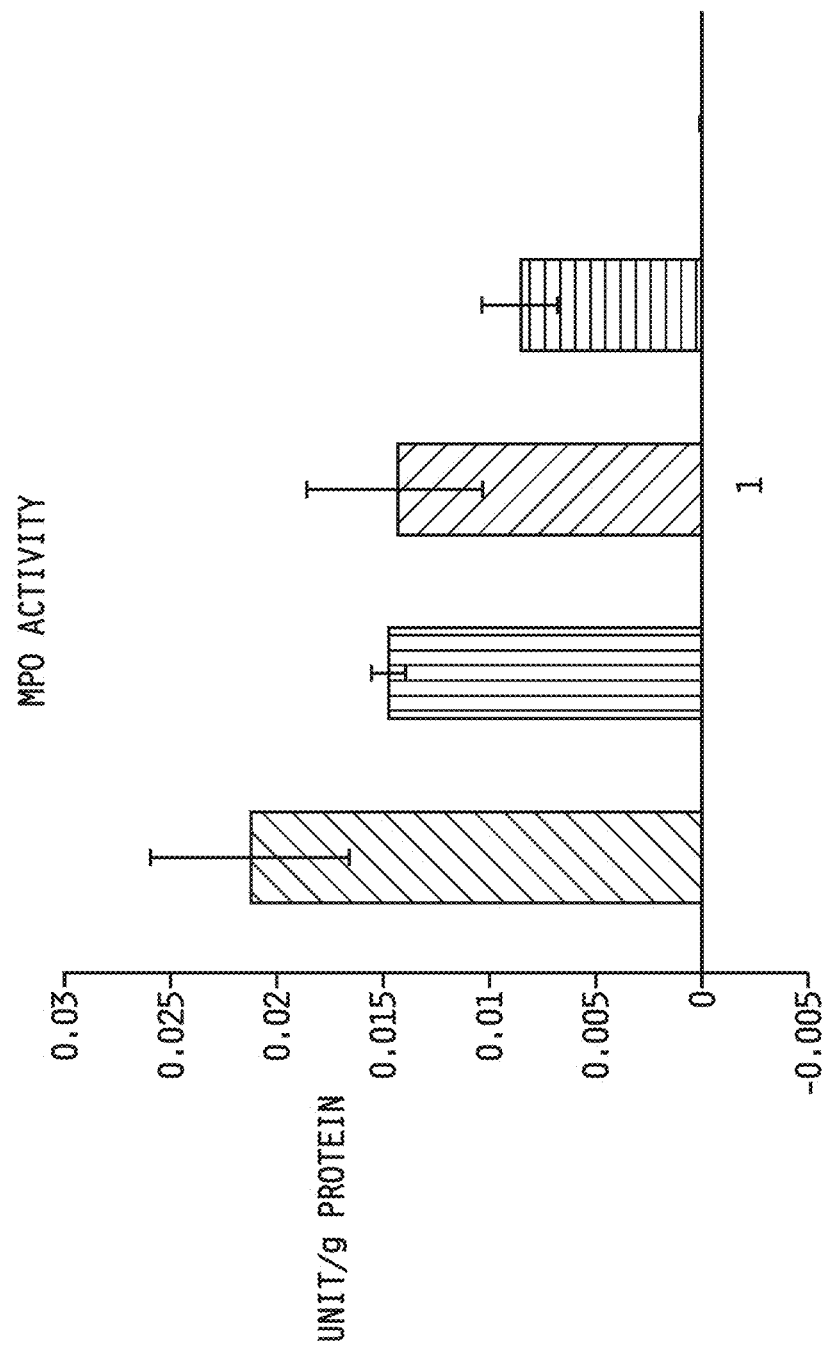

```
                        SEQUENCE LISTING

<160> NUMBER OF SEQ ID NOS: 60

<210> SEQ ID NO 1
    <211> LENGTH: 9
    <212> TYPE: PRT
    <213> ORGANISM: Unknown
    <220> FEATURE:
    <223> OTHER INFORMATION: MAMMALIAN
    <220> FEATURE:
    <221> NAME/KEY: MISC_FEATURE
    <222> LOCATION: (4)..(9)
    <223> OTHER INFORMATION: WHERE UP TO FIVE ARG ARE ABSENT

<400> SEQUENCE: 1

Arg Arg Arg Arg Arg Arg Arg Arg Arg
    1               5

<210> SEQ ID NO 2
    <211> LENGTH: 13
    <212> TYPE: PRT
    <213> ORGANISM: Unknown
    <220> FEATURE:
    <223> OTHER INFORMATION: MAMMALIAN

<400> SEQUENCE: 2

Gly Arg Lys Lys Arg Arg Gln Arg Arg Arg Pro Pro Gln
    1               5                   10

<210> SEQ ID NO 3
    <211> LENGTH: 8
    <212> TYPE: PRT
    <213> ORGANISM: Unknown
    <220> FEATURE:
    <223> OTHER INFORMATION: MAMMALIAN

<400> SEQUENCE: 3

Arg Gln Arg Arg Lys Lys Arg Gly
    1               5

<210> SEQ ID NO 4
    <211> LENGTH: 8
    <212> TYPE: PRT
    <213> ORGANISM: Unknown
    <220> FEATURE:
    <223> OTHER INFORMATION: MAMMALIAN

<400> SEQUENCE: 4

Gly Arg Lys Lys Arg Arg Gln Arg
    1               5

<210> SEQ ID NO 5
    <211> LENGTH: 12
```

```
<212> TYPE: PRT
<213> ORGANISM: Unknown
<220> FEATURE:
<223> OTHER INFORMATION: MAMMALIAN

<400> SEQUENCE: 5

Ala Tyr Ala Arg Ala Ala Ala Arg Gln Ala Arg Ala
1               5                   10

<210> SEQ ID NO 6
<211> LENGTH: 34
<212> TYPE: PRT
<213> ORGANISM: Unknown
<220> FEATURE:
<223> OTHER INFORMATION: MAMMALIAN

<400> SEQUENCE: 6

Asp Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Pro
            20                  25                  30

Val Glu

<210> SEQ ID NO 7
<211> LENGTH: 27
<212> TYPE: PRT
<213> ORGANISM: Unknown
<220> FEATURE:
<223> OTHER INFORMATION: MAMMALIAN

<400> SEQUENCE: 7

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 8
<211> LENGTH: 12
<212> TYPE: PRT
<213> ORGANISM: Unknown
<220> FEATURE:
<223> OTHER INFORMATION: MAMMALIAN

<400> SEQUENCE: 8

Pro Leu Ser Ser Ile Phe Ser Arg Ile Gly Asp Pro
1               5                   10

<210> SEQ ID NO 9
<211> LENGTH: 16
<212> TYPE: PRT
<213> ORGANISM: Unknown
<220> FEATURE:
<223> OTHER INFORMATION: MAMMALIAN

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 12
<212> TYPE: PRT
<213> ORGANISM: Unknown
<220> FEATURE:
<223> OTHER INFORMATION: MAMMALIAN

<400> SEQUENCE: 10
```

Ala Ala Val Leu Leu Pro Val Leu Leu Ala Ala Pro
1               5                   10

<210> SEQ ID NO 11
<211> LENGTH: 15
<212> TYPE: PRT
<213> ORGANISM: Unknown
<220> FEATURE:
<223> OTHER INFORMATION: MAMMALIAN

<400> SEQUENCE: 11

Val Thr Val Leu Ala Leu Gly Ala Leu Ala Gly Val Gly Val Gly
1               5                   10                  15

<210> SEQ ID NO 12
<211> LENGTH: 21
<212> TYPE: PRT
<213> ORGANISM: Unknown
<220> FEATURE:
<223> OTHER INFORMATION: MAMMALIAN

<400> SEQUENCE: 12

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 13
<211> LENGTH: 18
<212> TYPE: PRT
<213> ORGANISM: Unknown
<220> FEATURE:
<223> OTHER INFORMATION: MAMMALIAN

<400> SEQUENCE: 13

Lys Leu Ala Leu Lys Leu Ala Leu Lys Ala Leu Lys Ala Ala Leu Lys
1               5                   10                  15

Leu Ala

<210> SEQ ID NO 14
<211> LENGTH: 21
<212> TYPE: PRT
<213> ORGANISM: Unknown
<220> FEATURE:
<223> OTHER INFORMATION: MAMMALIAN

<400> SEQUENCE: 14

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 15
<211> LENGTH: 14
<212> TYPE: PRT
<213> ORGANISM: Unknown
<220> FEATURE:
<223> OTHER INFORMATION: MAMMALIAN

<400> SEQUENCE: 15

Lys Ala Phe Ala Lys Leu Ala Ala Arg Leu Tyr Arg Lys Ala
1               5                   10

<210> SEQ ID NO 16

<211> LENGTH: 14
<212> TYPE: PRT
<213> ORGANISM: Unknown
<220> FEATURE:
<223> OTHER INFORMATION: MAMMALIAN

<400> SEQUENCE: 16

Lys Ala Phe Ala Lys Leu Ala Ala Arg Leu Tyr Arg Ala Ala
1               5                   10

<210> SEQ ID NO 17
<211> LENGTH: 15
<212> TYPE: PRT
<213> ORGANISM: Unknown
<220> FEATURE:
<223> OTHER INFORMATION: MAMMALIAN

<400> SEQUENCE: 17

Ala Ala Phe Ala Lys Leu Ala Ala Ala Arg Leu Tyr Arg Lys Ala
1               5                   10                  15

<210> SEQ ID NO 18
<211> LENGTH: 14
<212> TYPE: PRT
<213> ORGANISM: Unknown
<220> FEATURE:
<223> OTHER INFORMATION: MAMMALIAN

<400> SEQUENCE: 18

Lys Ala Phe Ala Ala Leu Ala Ala Arg Leu Tyr Arg Lys Ala
1               5                   10

<210> SEQ ID NO 19
<211> LENGTH: 13
<212> TYPE: PRT
<213> ORGANISM: Unknown
<220> FEATURE:
<223> OTHER INFORMATION: MAMMALIAN

<400> SEQUENCE: 19

Lys Ala Phe Ala Lys Leu Ala Ala Arg Leu Tyr Arg Ala
1               5                   10

<210> SEQ ID NO 20
<211> LENGTH: 16
<212> TYPE: PRT
<213> ORGANISM: Unknown
<220> FEATURE:
<223> OTHER INFORMATION: MAMMALIAN

<400> SEQUENCE: 20

Lys Ala Phe Ala Lys Leu Ala Ala Arg Leu Tyr Arg Lys Ala Gly Cys
1               5                   10                  15

<210> SEQ ID NO 21
<211> LENGTH: 16
<212> TYPE: PRT
<213> ORGANISM: Unknown
<220> FEATURE:
<223> OTHER INFORMATION: MAMMALIAN

<400> SEQUENCE: 21

Lys Ala Phe Ala Lys Leu Ala Ala Arg Leu Tyr Arg Ala Ala Gly Cys
1               5                   10                  15

<210> SEQ ID NO 22
<211> LENGTH: 16

<212> TYPE: PRT
<213> ORGANISM: Unknown
<220> FEATURE:
<223> OTHER INFORMATION: MAMMALIAN

<400> SEQUENCE: 22

Ala Ala Phe Ala Lys Leu Ala Ala Arg Leu Tyr Arg Lys Ala Gly Cys
1               5                   10                  15

<210> SEQ ID NO 23
<211> LENGTH: 16
<212> TYPE: PRT
<213> ORGANISM: Unknown
<220> FEATURE:
<223> OTHER INFORMATION: MAMMALIAN

<400> SEQUENCE: 23

Lys Ala Phe Ala Ala Leu Ala Ala Arg Leu Tyr Arg Lys Ala Gly Cys
1               5                   10                  15

<210> SEQ ID NO 24
<211> LENGTH: 16
<212> TYPE: PRT
<213> ORGANISM: Unknown
<220> FEATURE:
<223> OTHER INFORMATION: MAMMALIAN

<400> SEQUENCE: 24

Lys Ala Phe Ala Lys Leu Ala Ala Gln Leu Tyr Arg Lys Ala Gly Cys
1               5                   10                  15

<210> SEQ ID NO 25
<211> LENGTH: 16
<212> TYPE: PRT
<213> ORGANISM: Unknown
<220> FEATURE:
<223> OTHER INFORMATION: MAMMALIAN

<400> SEQUENCE: 25

Ala Gly Gly Gly Gly Tyr Gly Arg Lys Lys Arg Arg Gln Arg Arg Arg
1               5                   10                  15

<210> SEQ ID NO 26
<211> LENGTH: 11
<212> TYPE: PRT
<213> ORGANISM: Unknown
<220> FEATURE:
<223> OTHER INFORMATION: MAMMALIAN

<400> SEQUENCE: 26

Tyr Ala Arg Ala Ala Ala Arg Gln Ala Arg Ala
1               5                   10

<210> SEQ ID NO 27
<211> LENGTH: 11
<212> TYPE: PRT
<213> ORGANISM: Unknown
<220> FEATURE:
<223> OTHER INFORMATION: MAMMALIAN

<400> SEQUENCE: 27

Tyr Gly Arg Lys Lys Arg Arg Gln Arg Arg Arg
1               5                   10

<210> SEQ ID NO 28
<211> LENGTH: 14
<212> TYPE: PRT

```
<213> ORGANISM: Unknown
<220> FEATURE:
<223> OTHER INFORMATION: MAMMALIAN

<400> SEQUENCE: 28

Trp Leu Arg Arg Ile Lys Ala Trp Leu Arg Arg Ile Lys Ala
1               5                   10

<210> SEQ ID NO 29
<211> LENGTH: 21
<212> TYPE: PRT
<213> ORGANISM: Unknown
<220> FEATURE:
<223> OTHER INFORMATION: MAMMALIAN

<400> SEQUENCE: 29

Trp Leu Arg Arg Ile Lys Ala Trp Leu Arg Arg Ile Lys Ala Trp Leu
1               5                   10                  15

Arg Arg Ile Lys Ala
            20

<210> SEQ ID NO 30
<211> LENGTH: 12
<212> TYPE: PRT
<213> ORGANISM: Unknown
<220> FEATURE:
<223> OTHER INFORMATION: MAMMALIAN

<400> SEQUENCE: 30

Phe Ala Lys Leu Ala Ala Arg Leu Tyr Arg Lys Ala
1               5                   10

<210> SEQ ID NO 31
<211> LENGTH: 12
<212> TYPE: PRT
<213> ORGANISM: Unknown
<220> FEATURE:
<223> OTHER INFORMATION: MAMMALIAN

<400> SEQUENCE: 31

Phe Ala Lys Leu Ala Ala Arg Leu Tyr Arg Ala Ala
1               5                   10

<210> SEQ ID NO 32
<211> LENGTH: 11
<212> TYPE: PRT
<213> ORGANISM: Unknown
<220> FEATURE:
<223> OTHER INFORMATION: MAMMALIAN

<400> SEQUENCE: 32

Phe Ala Lys Leu Ala Ala Arg Leu Tyr Arg Ala
1               5                   10

<210> SEQ ID NO 33
<211> LENGTH: 22
<212> TYPE: PRT
<213> ORGANISM: Unknown
<220> FEATURE:
<223> OTHER INFORMATION: MAMMALIAN

<400> SEQUENCE: 33

Tyr Ala Arg Ala Ala Ala Arg Gln Ala Arg Ala Lys Ala Leu Ala Arg
1               5                   10                  15

Gln Leu Gly Val Ala Ala
            20
```

```
<210> SEQ ID NO 34
<211> LENGTH: 22
<212> TYPE: PRT
<213> ORGANISM: Unknown
<220> FEATURE:
<223> OTHER INFORMATION: MAMMALIAN

<400> SEQUENCE: 34

Tyr Gly Arg Lys Lys Arg Arg Gln Arg Arg Lys Ala Leu Ala Arg
1               5                   10                  15

Gln Leu Gly Val Ala Ala
            20

<210> SEQ ID NO 35
<211> LENGTH: 19
<212> TYPE: PRT
<213> ORGANISM: Unknown
<220> FEATURE:
<223> OTHER INFORMATION: MAMMALIAN

<400> SEQUENCE: 35

Arg Gln Arg Arg Lys Lys Arg Gly Lys Ala Leu Ala Arg Gln Leu Gly
1               5                   10                  15

Val Ala Ala

<210> SEQ ID NO 36
<211> LENGTH: 19
<212> TYPE: PRT
<213> ORGANISM: Unknown
<220> FEATURE:
<223> OTHER INFORMATION: MAMMALIAN

<400> SEQUENCE: 36

Gly Arg Lys Lys Arg Arg Gln Arg Lys Ala Leu Ala Arg Gln Leu Gly
1               5                   10                  15

Val Ala Ala

<210> SEQ ID NO 37
<211> LENGTH: 25
<212> TYPE: PRT
<213> ORGANISM: Unknown
<220> FEATURE:
<223> OTHER INFORMATION: MAMMALIAN

<400> SEQUENCE: 37

Trp Leu Arg Arg Ile Lys Ala Trp Leu Arg Arg Ile Lys Ala Lys Ala
1               5                   10                  15

Leu Ala Arg Gln Leu Gly Val Ala Ala
20                  25

<210> SEQ ID NO 38
<211> LENGTH: 31
<212> TYPE: PRT
<213> ORGANISM: Unknown
<220> FEATURE:
<223> OTHER INFORMATION: MAMMALIAN

<400> SEQUENCE: 38

Trp Leu Arg Arg Ile Lys Ala Trp Leu Arg Ile Lys Ala Trp Leu Arg
1               5                   10                  15

Arg Ile Lys Ala Lys Ala Leu Ala Arg Gln Leu Gly Val Ala Ala
            20                  25                  30
```

```
<210> SEQ ID NO 39
<211> LENGTH: 24
<212> TYPE: PRT
<213> ORGANISM: Unknown
<220> FEATURE:
<223> OTHER INFORMATION: MAMMALIAN

<400> SEQUENCE: 39

Tyr Ala Arg Ala Ala Ala Arg Gln Ala Arg Ala Lys Lys Lys Ala Leu
1               5                   10                  15

Ala Arg Gln Leu Gly Val Ala Ala
            20

<210> SEQ ID NO 40
<211> LENGTH: 24
<212> TYPE: PRT
<213> ORGANISM: Unknown
<220> FEATURE:
<223> OTHER INFORMATION: MAMMALIAN

<400> SEQUENCE: 40

Tyr Gly Arg Lys Lys Arg Arg Gln Arg Arg Lys Lys Lys Ala Leu
1               5                   10                  15

Ala Arg Gln Leu Gly Val Ala Ala
            20

<210> SEQ ID NO 41
<211> LENGTH: 21
<212> TYPE: PRT
<213> ORGANISM: Unknown
<220> FEATURE:
<223> OTHER INFORMATION: MAMMALIAN

<400> SEQUENCE: 41

Arg Gln Arg Arg Lys Lys Arg Gly Lys Lys Ala Leu Ala Arg Gln
1               5                   10                  15

Leu Gly Val Ala Ala
            20

<210> SEQ ID NO 42
<211> LENGTH: 21
<212> TYPE: PRT
<213> ORGANISM: Unknown
<220> FEATURE:
<223> OTHER INFORMATION: MAMMALIAN

<400> SEQUENCE: 42

Gly Arg Lys Lys Arg Arg Gln Arg Lys Lys Ala Leu Ala Arg Gln
1               5                   10                  15

Leu Gly Val Ala Ala
            20

<210> SEQ ID NO 43
<211> LENGTH: 27
<212> TYPE: PRT
<213> ORGANISM: Unknown
<220> FEATURE:
<223> OTHER INFORMATION: MAMMALIAN

<400> SEQUENCE: 43

Trp Leu Arg Arg Ile Lys Ala Trp Leu Arg Arg Ile Lys Ala Lys Lys
1               5                   10                  15

Lys Ala Leu Ala Arg Gln Leu Gly Val Ala Ala
            20                  25
```

<210> SEQ ID NO 44
<211> LENGTH: 34
<212> TYPE: PRT
<213> ORGANISM: Unknown
<220> FEATURE:
<223> OTHER INFORMATION: MAMMALIAN

<400> SEQUENCE: 44

Trp Leu Arg Arg Ile Lys Ala Trp Leu Arg Arg Ile Lys Ala Trp Leu
1               5                   10                  15

Arg Arg Ile Lys Ala Lys Lys Lys Ala Leu Ala Arg Gln Leu Gly Val
            20                  25                  30

Ala Ala

<210> SEQ ID NO 45
<211> LENGTH: 23
<212> TYPE: PRT
<213> ORGANISM: Unknown
<220> FEATURE:
<223> OTHER INFORMATION: MAMMALIAN

<400> SEQUENCE: 45

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 46
<211> LENGTH: 21
<212> TYPE: PRT
<213> ORGANISM: Unknown
<220> FEATURE:
<223> OTHER INFORMATION: MAMMALIAN

<400> SEQUENCE: 46

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 47
<211> LENGTH: 23
<212> TYPE: PRT
<213> ORGANISM: Unknown
<220> FEATURE:
<223> OTHER INFORMATION: MAMMALIAN

<400> SEQUENCE: 47

Lys Ala Phe Ala Lys Leu Ala Ala Arg Leu Tyr Arg Ala Ala Leu Ala
1               5                   10                  15

Arg Gln Leu Gly Val Ala Ala
            20

<210> SEQ ID NO 48
<211> LENGTH: 22
<212> TYPE: PRT
<213> ORGANISM: Unknown
<220> FEATURE:
<223> OTHER INFORMATION: MAMMALIAN

<400> SEQUENCE: 48

Lys Ala Phe Ala Lys Leu Ala Ala Arg Leu Tyr Arg Ala Leu Ala Arg
1               5                   10                  15

-continued

Gln Leu Gly Val Ala Ala
            20

<210> SEQ ID NO 49
<211> LENGTH: 23
<212> TYPE: PRT
<213> ORGANISM: Unknown
<220> FEATURE:
<223> OTHER INFORMATION: MAMMALIAN

<400> SEQUENCE: 49

Lys Ala Phe Ala Ala Leu Ala Ala Arg Leu Tyr Arg Ala Ala Leu Ala
1               5                   10                  15

Arg Gln Leu Gly Val Ala Ala
            20

<210> SEQ ID NO 50
<211> LENGTH: 21
<212> TYPE: PRT
<213> ORGANISM: Unknown
<220> FEATURE:
<223> OTHER INFORMATION: MAMMALIAN

<400> SEQUENCE: 50

Phe Ala Lys Leu Ala Ala Arg Leu Tyr Arg Ala Ala Leu Ala Arg Gln
1               5                   10                  15

Leu Gly Val Ala Ala
            20

<210> SEQ ID NO 51
<211> LENGTH: 21
<212> TYPE: PRT
<213> ORGANISM: Unknown
<220> FEATURE:
<223> OTHER INFORMATION: MAMMALIAN

<400> SEQUENCE: 51

Tyr Ala Arg Ala Ala Arg Gln Ala Arg Ala Lys Ala Leu Asn Arg
1               5                   10                  15

Gln Leu Gly Val Ala
            20

<210> SEQ ID NO 52
<211> LENGTH: 23
<212> TYPE: PRT
<213> ORGANISM: Unknown
<220> FEATURE:
<223> OTHER INFORMATION: MAMMALIAN

<400> SEQUENCE: 52

Lys Ala Phe Ala Lys Leu Ala Ala Arg Leu Tyr Arg Lys Ala Leu Asn
1               5                   10                  15

Arg Gln Leu Ala Val Ala Ala
            20

<210> SEQ ID NO 53
<211> LENGTH: 21
<212> TYPE: PRT
<213> ORGANISM: Unknown
<220> FEATURE:
<223> OTHER INFORMATION: MAMMALIAN

<400> SEQUENCE: 53

Phe Ala Lys Leu Ala Ala Arg Leu Tyr Arg Lys Ala Leu Asn Arg Gln

```
1               5                   10                  15

Leu Ala Val Ala Ala
            20

<210> SEQ ID NO 54
<211> LENGTH: 10
<212> TYPE: PRT
<213> ORGANISM: Unknown
<220> FEATURE:
<223> OTHER INFORMATION: MAMMALIAN

<400> SEQUENCE: 54

Lys Ala Leu Asn Arg Gln Leu Gly Val Ala
1               5                   10

<210> SEQ ID NO 55
<211> LENGTH: 10
<212> TYPE: PRT
<213> ORGANISM: Unknown
<220> FEATURE:
<223> OTHER INFORMATION: MAMMALIAN

<400> SEQUENCE: 55

Lys Ala Leu Asn Arg Gln Leu Gly Val Ala
1               5                   10

<210> SEQ ID NO 56
<211> LENGTH: 21
<212> TYPE: PRT
<213> ORGANISM: Unknown
<220> FEATURE:
<223> OTHER INFORMATION: MAMMALIAN

<400> SEQUENCE: 56

Trp Leu Arg Arg Ile Lys Ala Trp Arg Ile Lys Ala Leu Asn Arg
1               5                   10                  15

Gln Leu Gly Val Ala
            20

<210> SEQ ID NO 57
<211> LENGTH: 22
<212> TYPE: PRT
<213> ORGANISM: Unknown
<220> FEATURE:
<223> OTHER INFORMATION: MAMMALIAN

<400> SEQUENCE: 57

Lys Ala Phe Ala Leu Lys Ala Ala Arg Leu Tyr Arg Lys Ala Leu Asn
1               5                   10                  15

Arg Gln Leu Gly Val Ala
            20

<210> SEQ ID NO 58
<211> LENGTH: 20
<212> TYPE: PRT
<213> ORGANISM: Unknown
<220> FEATURE:
<223> OTHER INFORMATION: MAMMALIAN

<400> SEQUENCE: 58

Phe Ala Lys Leu Ala Ala Arg Leu Tyr Arg Lys Ala Leu Asn Arg Gln
1               5                   10                  15

Leu Gly Val Ala
            20
```

```
<210> SEQ ID NO 59
<211> LENGTH: 22
<212> TYPE: PRT
<213> ORGANISM: Unknown
<220> FEATURE:
<223> OTHER INFORMATION: MAMMALIAN

<400> SEQUENCE: 59

Tyr Ala Arg Ala Ala Ala Arg Gln Ala Arg Ala Lys Ala Leu Asn Arg
1               5                   10                  15

Gln Leu Gly Val Ala Ala
            20

<210> SEQ ID NO 60
<211> LENGTH: 21
<212> TYPE: PRT
<213> ORGANISM: Unknown
<220> FEATURE:
<223> OTHER INFORMATION: MAMMALIAN

<400> SEQUENCE: 60

Phe Ala Lys Leu Ala Ala Arg Leu Tyr Arg Lys Leu Ala Leu Arg Gln
1               5                   10                  15

Leu Gly Val Ala Ala
            20
```

MK2 INHIBITOR COMPOSITIONS AND METHODS TO ENHANCE NEURITE OUTGROWTH, NEUROPROTECTION, AND NERVE REGENERATION

CROSS REFERENCE TO RELATED APPLICATIONS

This application claims the benefit of U.S. Provisional Application No. 61/228,738, filed Jul. 27, 2009, the contents of which are incorporated by reference in their entirety.

STATEMENT OF GOVERNMENT FUNDING

This invention was made with government support under Grant 00014975 awarded by the Indiana State Department of Health. The government has certain rights in the invention.

FIELD OF THE INVENTION

The invention relates to cell biology, peptides for enhancing neurite outgrowth, methods of use thereof, neuroprotection, and nerve regeneration.

BACKGROUND

Neurons

Neurons or nerve cells are excitable cells in the nervous system that respond to stimuli. They are the core components of the brain, the vertebrate spinal cord, the invertebrate ventral nerve cord, and the peripheral nerves. Neurons do not go through mitosis, and usually cannot be replaced after being destroyed.

Neurons are highly specialized for the processing and transmission of cellular signals. Their wide variety in shape, size and electrochemical properties is reflective of the diversity of functions they perform in different parts of the nervous system. A number of specialized types of neurons exist. For example, sensory neurons (afferent) respond to touch, sound, light and numerous other stimuli affecting cells of the sensory organs that then send signals to the spinal cord and brain, while motor neurons (efferent) receive signals from the brain and spinal cord, cause muscle contractions and affect glands.

The typical neuron has four morphologically defined regions: (1) the cell body (also called the soma or perikaryon), (2) the dendrites, (3) the axon and (4) the presynaptic terminals of the axon. Nerve cells generate active electrical signals, and each region has distinctive signaling functions.

The cell body is the metabolic center of the neuron. Three organelles are characteristic of the cell body: the nucleus, which in neurons often is quite large; the endoplasmic reticulum, upon which membrane and secretory proteins are synthesized; and the Golgi apparatus, which carries out the processing of secretory and membrane components. The cell body usually gives rise to several fine arborizing outgrowths or extensions called dendrites, which serve as the chief receptive apparatus for the neuron. The cell body also gives rise to the axon, a tubular process that can extend considerable distances (up to 1 m in humans).

The axon constitutes the conducting unit of the neuron. Axons lack ribosomes and therefore cannot synthesize proteins. Newly synthesized macromolecules are assembled into organelles within the cell body and are moved along the axon to the presynaptic terminals by a process called axoplasmic transport. When severed from the cell body, the axon usually degenerates and dies. Large axons are surrounded by a fatty insulating sheath called myelin, which is essential for high-speed conduction of action potentials. The myelin sheath is interrupted at very regular intervals. These points of interruption are called nodes of Ranvier.

Near its end, the axon divides into many fine branches, which have specialized endings called presynpatic terminals. The presynaptic terminals are the transmitting elements of the neuron. By means of its terminals, one neuron contacts and transmits information about its own activity to the receptive surfaces of another neuron, a muscle or other kinds of effector cells. The point of contact is the synapse. It is formed by the presynaptic terminal of one cell (the presynpatic cell), the receptive surface of the other (the postsynaptic cell), and the space separating them (the synaptic cleft). The terminals of the presynaptic neuron sometimes contact the postsynaptic neuron on its cell body, but more commonly the contacts occur on dendrites. Less often, synapses are located on the initial or on the terminal portions of axons.

On the basis of the number of processes that arise from the cell body, neurons are classified into three groups: unipolar, bipolar and multipolar.

Unipolar cells have one primary process that may give rise to many branches. Some branches serve as dendritic receiving structures, and other branches as axons and terminal structures. Unipolar cells predominate in the nervous systems of invertebrates in collections of nerve cells located near the spinal cord in the sensory ganglia of the dorsal roots.

Bipolar neurons have an ovoid soma that gives rise to one process at each end: a dendrite or peripheral process (which picks up information from the periphery), and an axon or central process (which carries information toward the central nervous system). The bipolar cells of the retina are examples of this class.

Multipolar neurons predominate in the vertebrate nervous system. These cells have one or more dendritic branches and a single axon. In a typical multipolar cell, dendrites emerge from all parts of the cell body; variants are the pyramidal cell of the cerebral cortex and the Purkinje cell, a class of GAGAergic neurons located in the cerebellar cortex.

Even within the category of multipolar neurons, the size and shape of different cells vary greatly. Different types of multipolar cells account for nearly all of the distinguishable neuronal cell types, which number between 1,000 and 10,000. The morphological differences among multipolar cells are due largely to variations in two features: the number and length of the dendrites, and the length of the axon. The number and extent of dendritic processes in a given cell correlate with the number of synaptic contacts that other neurons make on that cell. For example, a spinal motor cell, whose dendrites are moderate in both number and extent, receives roughly 10,000 contacts, while the large dendritic tree of the Purkinje cell of the cerebellum receives approximately 150,000 contacts.

The length of the axon reflects the signaling function of a neuron. Neurons with long axons ("Golgi type I cells") carry information from one brain region to another; they serve as projection or relay neurons. Neurons with short axons ("Golgi type II cells") primarily process information within a small, limited region of the brain. These nerve cells serve as local interneurons in various nuclei of the brain and in reflex pathways.

The movement of axons is determined by their growth cones, expansions of the tip of the growing axon that generate the mechanical force that pulls the axon forward.

The growth cone has a broad sheet-like extension (lamellipodia) which contain protrusions (filopodia). The motility of growth cones is punctuated by cycles of protrusion, adhesion, and contraction. Actin plays a major role in the mobility of this system.

The direction pursued by the growth cones of an outgrowing axon is influenced by a variety of cues that range from (1) simple differences in the texture and stickiness of the substrate, to (2) rather precise molecular cues from recognition molecules imbedded in the surface membrane of the cells over which the growth cone crawls, to (3) diffusible gradients set up by a distant source. Further, guidepost cells, which typically are other neurons, may assist in the guidance of neuronal axon growth.

It is likely that the physical substrate over which an axon grows out contributes cues that guide the growth cone to its target. Substrates vary in adhesiveness, and that selective adhesion can guide the direction of the outgrowing process. Variations in the texture and shape of the available surfaces on which processes grow may produce regional differences in the adhesion between the growth cone and the substrate that determine the direction of growth. Environments with high levels of cell adhesion molecules (CAM's) create an ideal environment for axonal growth. Generally, it is believed that this provides a "sticky" surface along which axons can grow. Examples of CAM's specific to neural systems include the immunoglobulins N-CAM, neuroglial CAM (NgCAM), TAG-1, MAG, and DCC. Extracellular matrix adhesion molecules (ECMs) also provide a sticky substrate along which axons can grow. Examples of ECMs include laminin, fibronectin, tenascin, and perlecan. Some ECMs are surface-bound to cells and thus act as short range attractants or repellents. Others are diffusible ligands and thus can have long range effects.

In addition to adhesiveness, growth cones also might also sense more specific recognition molecules. For example, specific receptors on the surface of outgrowing growth cones might recognize molecules on the surface of cells forming the substrate. Alternatively, a signal molecule might be secreted by a substrate cell and internalized by the outgrowing cell; the molecule then could act from within the second cell to influence the direction of neurite outgrowth.

Nervous System

The nervous system is divided into two parts: the central nervous system (CNS), which consists of the brain and spinal cord, and the peripheral nervous system (PNS), which consists of cranial and spinal nerves along with their associated ganglia.

Central Nervous System (CNS)

The CNS consists of six main regions: (1) the spinal cord; (2) the medulla; (3) the pons; (4) the midbrain; (5) the diencephalon; and (6) the cerebral hemispheres.

The spinal cord, the most caudal part of the CNS, receives information from the skin, joints, and muscles in the trunk and limbs, and it is the final way station for issuing commands for movement. In the spinal cord there is an orderly arrangement of motor and sensory nucleic controlling the limbs and trunk. In addition to nuclei, the spinal cord contains afferent pathways for sensory information to flow to the brain and efferent pathways for commands necessary for motor control to descend from the brain to the motor neurons. The spinal cord also receives sensory information from the internal organs and controls many autonomic functions.

The spinal cord continues rostrally as the brain stem, which comprises the medulla, the pons and the midbrain. The medulla is the most direct rostral extension of the spinal cord and resembles the spinal cord in aspects of its organization. The pons, which lies rostral to the medulla, contains a massive set of neurons that relay information from the cerebral hemispheres to the cerebellum. The cerebellum is not part of the brain stem, but because of its position dorsal to the pons, it is commonly grouped together with the pons. The midbrain lies rostral to the pons, and is important in the control of eye movement. The midbrain also contains an essential relay in the auditory pathway and several structures critically involved in motor control of skeletal muscles.

The diencephalon contains two key subdivisions: the thalamus and the hypothalamus. The thalamus processes and relays most of the information coming from the lower regions of the CNS en route to the cerebral cortex. The hypothalamus is important for integration in the autonomic nervous system and for regulating hormonal secretion by the pituitary gland.

The cerebral hemispheres consist of the cerebral cortex and the basal ganglia. Collectively termed the "cerebrum", these structures are concerned with perceptual, cognitive, and higher motor functions. The cerebral cortex is further subdivided into four lobes: frontal, parietal, temporal and occipital. Large regions of the cerebral cortex are committed to movement and sensation. Areas that are directly committed are called primary, secondary, and tertiary sensory or motor areas. Surrounding the primary areas are higher order (secondary and tertiary) sensory and motor areas. These areas process more complex aspects of a single sensory modality or motor function than primary areas. The purpose of the higher order sensory areas is to achieve greater analysis and integration of information coming from the primary sensory areas. In contrast, the flow of information from the motor areas is in the opposite direction. Higher order motor areas distill complex information about a potential motor act and relay it to the primary motor cortex, which is the site from which voluntary movement is initiated.

Peripheral Nervous System (PNS)

The peripheral nervous system (PNS) resides or extends outside the CNS. The main function of the PNS is to connect the CNS to the limbs and organs. The PNS is divided by function into the somatic nervous system, the autonomic nervous system and the enteric nervous system.

The somatic nervous system is responsible for coordinating the body movements, and also for receiving external stimuli. It regulates activities that are under conscious control.

The autonomic nervous system (or autonomic motor system) provides the innervation for the endocrine and exocrine glands, for the viscera, and for smooth muscles in all organs of the body. The autonomic nervous system has two major divisions: the sympathetic and parasympathetic. The sympathetic system often mediates the response of the body to stress; it speeds up heart rate, increase blood pressure, mobilizes the body's energy stores for emergency, and prepares for action. In contrast, the parasympathetic system acts to conserve the body's resources and restore homeostasis; it slows the heart, reduces blood pressure, and prepares the body for relaxation and rest. The two divisions are segregated anatomically. The cell bodies that give rise to the sympathetic division lie in the thoracic and lumbar regions of the spinal cord. The neurons that give rise to the parasympathetic division lie above this region of the spinal cord in several brain stem nuclei associated with cranial nerves, and below it in the sacral region of the spinal cord. The autonomic nuclei in the brain stem and spinal cord contain neurons (preganglionic cells) that send their axons to synapse on a second set of neurons (postganglionic cells)

that lie in peripheral collections of nerve cell bodies (autonomic ganglia). the postganglionic cells in turn innervate viscera, glands, and smooth muscle.

The main control center for the autonomic motor system is the hypothalamus, which also is critically involved in the regulation of feeding and drinking. The hypothalamus sends out descending fibers that regulate sympathetic and parasympathetic nuclei in the spinal cord and brain stem, axons that control the release of hormones by the anterior pituitary gland, and axons that release hormones directly into the posterior pituitary gland. The hypothalamus receives information from many other structures, including higher levels of the motivational systems: the cerebral cortex and the reticular formation.

The enteric nervous system controls the gastrointestinal system. The enteric nervous system is capable of autonomous functions, such as the coordination of reflexes, and may contain as many as 100,000,000 neurons. The neurons of the enteric nervous system are collected into two types of ganglia: myenteric (Auerbach's) and submucosal (Meissner's) plexuses. Myenteric plexuses are located between the inner and outer layers of the muscularis externa. Submucosal plexuses are located in the submucosa (the layer of dense irregular connective tissue that supports the mucosa). In vertebrates, the enteric nervous system includes efferent neurons, afferent neurons, and interneurons, all of which make the enteric nervous system capable of carrying reflexes and acting as an integrating center in the absence of CNS input.

Nerve Injury and Disorders

Damage to nervous tissue is particularly serious because most neurons in the adult mammalian CNS have withdrawn from the mitotic cycle and no longer are capable of cell division. Consequently, any physical injury that causes neurons to die will not be followed by regeneration of cells but will bring about a permanent change in the structure of the nervous system. This structural change usually is accompanied by long-lasting alterations in the functions of the affected areas.

The term "axotomy" refers to the cutting or severing of a neuron's axon. Cutting an axon interrupts both rapid axonal transport and slower axoplasmic flow, the two mechanisms that carry materials synthesized in the neuronal cell body to the axon terminals. The axon and the synaptic terminals degenerate when deprived of their normal metabolic interaction with the cell body. The term "anterograde" or "Wallerian" degeneration as used herein refers to degeneration of that part of the axon disconnected from the cell body which would be considered distal relative to the lesion. The term "retrograde" degeneration refers to changes proximal to the lesion site in the part of the axon that remains connected to the cell body. Retrograde changes are found quite frequently after axotomy; in some instances they are severe and can result in death of the neuron.

Synapses mediate not only electrical signals but also nutritive (trophic) interactions between neurons. Trophic factors are crucial for the normal maintenance of these cells. Like synaptic interactions, trophic interactions are thought to occur via a neuron's synaptic contacts. Deprived of its synaptic terminals, a neuron may shrink, atrophy or degenerate. Therefore, if a bundle of axons in the CNS is severed, degenerative changes may be found not only in the damaged neurons but also in neurons that receive synapses from the damaged neurons. In some injuries, the presynaptic neurons that synapse on the damaged cells also are affected (these reactions are referred to as "transsynpatic" or "transneuronal" meaning that they cross from one neuron to the next via the synapse). These influences may be mild, or they can be drastic and cause degeneration of the affected neurons. Transneuronal changes of various kinds are important in explaining why a lesion at one site in the CNS can have effects on sites distant to the lesion, sites that are distributed according to the connections that the lesion interrupts.

Glial Cells

In addition to neurons, nervous tissue contains glial cells (oligodendrocytes, astrocytes, ependymal cells, Schwann cells and microglia). Some of these cells play an important role in healing. Certain types of supporting cells absorb the cellular debris that results from neuronal injury by taking up and destroying (phagocytosing) toxic products of degeneration, while other supporting cells sometimes can interfere with healing if their proliferation blocks the restoration of severed synaptic connections within the brain and spinal cord. Therefore, the healing processes that are activated in the CNS by neuronal injury can be both helpful (e.g. phagocytosis) and troublesome (e.g. blocked regeneration).

Two types of glial cells, astrocytes and oligodendrocytes, vastly outnumber neurons. Astrocytes predominate in gray matter. They have small cell bodies (3-5 μm) that are packed with bundles of glial filaments about 100 nm in diameter. Numerous processes radiate from the cell body in various directions, and many of these come into close contact with blood vessels The term "sclerosis" often is used to describe disease states, such as multiple sclerosis, that affect populations of axons in the brain, and refers to the palpably hard scar of astrocytes that replaces phagocytosed debris resulting from the disease process.

Oligodendrocytes, which form myelin in the CNS, predominate in white matter. They have smaller cell bodies (1-3 μm in diameter) and give off fewer processes than astrocytes; each process appears to participate in forming myelin for a single axon. In the CNS, each oligodendrocyte contributes to the myelin sheath of several (as many as 20) axons by means of its different processes.

Glial cells proliferate around chromatolytic neurons and assume the appearance of phagocytes. The term "chromatolysis" (and its various grammatical forms) is used herein to refer to reorganizational changes in the cell body of a damaged neuron. Glial cells have been observed displacing presynaptic terminals along the proximal dendrites and cell bodies of axonotomized motor neurons. The pre- and post-synaptic elements of the synapse appear to be pushed apart by the invading glial cells. Damaged neurons receive reduced synaptic inputs, and the evoked excitatory postsynaptic potentials are smaller in amplitude, as if synapses on the cell body and proximal dendrites were removed by encroachment of glial cells. Even though somatic synapses are displaced, chromatolysing motor neurons still can be activated because remote synapses on their dendritic tree that normally are ineffective begin to excite the cell. After the normal input to the soma is removed, new trigger zones develop on the cell body and along the axon. A reorganization of this type may enable the cell to maintain normal number of synapses. If appropriate connections with muscles are established by the regenerating motor axons, then the normal input to the cell body of the motor neuron returns.

If a bundle of axons is cut, either by sectioning of a tract within the brain or by sectioning of a peripheral nerve, the site where the lesion is located is termed the "zone of trauma." The part of the axon still connected to the cell body is the "proximal segment," and the part isolated from the rest of the cell is the "distal segment." The cut ends of both parts of the axon lose axoplasm immediately after injury, but the ends soon become sealed off by fusion of the axon membrane, retract from one another, and begin to swell. The swollen reaction bulbs that result are formed largely by materials carried along the axon by axonal transport and axoplasmic flow. Mitochondria, vesicles, multivesicular bodies and much unidentified membranous material pile up in the sealed end of each axon segment. Although both the proximal and the distal segments swell (because fast axonal transport occurs in two directions), the proximal end swells more, because newly synthesized neurofilaments, microtubules, and microfilaments, traveling by slow axoplasmic flow, come from the cell body only.

Types of Nerve Injury

Nerve injury may be classified into three types: neurapraxia; axonotmesis; and neurtmesis.

In neurapraxia, the least severe form of nerve injury with complete recovery, the actual structure of the nerve remains intact, but there is an interruption in conduction of the impulse down the nerve fiber. Most commonly, this involves compression of the nerve or disruption to the blood supply (ischemia). There is a temporary loss of function which is reversible within hours to months of the injury (the average is 6-8 weeks). Wallerian degeneration (a process that results when a nerve fiber is cut or crushed in which the part of the axon separated from the neuron's cell nucleus degenerates) does not occur, so recovery does not involve actual regeneration. There frequently is greater involvement of motor than sensory function with autonomic function being retained.

Axonotmesis, a more severe nerve injury with disruption of the neuronal axon, but with maintenance of the myelin sheath, results in loss of the relative continuity of the axon and its covering of myelin, but preservation of the connective tissue framework of the nerve (i.e, the encapsulating tissue, the epineurium and perineurium, are preserved) leading to Wallerian degeneration. Loss in both motor and sensory spines is more complete with axonotmesis than with neurapraxia, and recovery occurs only through regenerations of the axons. There usually is an element of retrograde proximal degeneration of the axon, and for regeneration to occur, this loss first must be overcome. The regeneration fibers must cross the injury site, and regeneration through the proximal or retrograde area of degeneration may require several weeks; then the neuritic tip progresses down the distal site. The proximal lesion may grow distally as fast as 2 mm to 3 mm per day and the distal lesion as slowly as 1.5 mm per day. Regeneration may take several weeks or years.

Neurotmesis, the most severe lesion with potential of recovery, occurs on severe contusion, stretch, laceration or local anesthetic toxicity. Not only the axon but also the encapsulating connective tissue lose their connectivity. The last (extreme) degree of neurotmesis is transection. Most neurotmetic injuries do not produce gross loss of continuity of the nerve but rather internal disruption of the architecture of the nerve sufficient to involve the perineurium [one of the supporting structures of peripheral nerve trunks, consisting of layers off lattened cells and collagenous connective tissue, which surround the nerve fasciculi and form the major diffusion barrier within the nerve] and endoneurium [the innermost connective tissue supportive structure of nerve trunks that surrounds both myelinated and unmyelinated nerve fibers, consisting principally of ground substance, collagen, and fibroblasts] as well as axons and their covering. There is a complete loss of motor, sensory and autonomic function. If the nerve has been completely divided, axonal regeneration causes a neuroma (swelling or pseudoneuroma) to form in the proximal stump.

Neuroregeneration

The term "neuroregeneration" (or "nerve regeneration") refers to the growth or repair of nervous tissues, cells or cell products. Repair mechanisms may include, but are not limited to, remyelination and generation of new neurons, glia, axons, myelin and synapses.

While the PNS has an intrinsic ability for repair and regeneration, the CNS is, for the most part, incapable of self-repair and regeneration. Currently, there is no treatment for recovering human nerve function after injury to the CNS.

Neuroregeneration in the CNS

Unlike PNS injury, injury to the CNS is not followed by extensive regeneration. Several factors may contribute to this inactivity. The environment within the CNS, especially following trauma, hinders the repair of myelin and neurons, and, generally, growth factors are not expressed or re-expressed (for example, the extracellular matrix lacks laminins). Additionally, the axons themselves lose the potential for growth with age. Further, a distal segment in the CNS degenerates slower than in the PNS; the slower removal of myelin and axonal debris contributes to the inhibitory environment. All these factors contribute to the formation of what is known as a glial scar, across which axons cannot grow. Several families of molecules are released that promote and drive glial scar formation. Transforming growth factors $\beta$-1 and $\beta$-2, interleukins, and cytokines all are believed to play a role in the initiation of scar formation. The glia further produce factors that inhibit remyelination and axon repair, such as, for example, NOGO and NI-35.

At a zone of trauma in the CNS, the axon and myelin sheath undergo rapid local degeneration. Because blood vessels usually are interrupted by a lesion, macrophages from the general circulation can enter the area and phagocytose axonal debris. Glial cells (astrocytes and microglia) also proliferate and act as phagocytes. In the CNS, however, the proliferation of fibrous astrocytes leads to the formation of a glial scar around the zone of trauma. Scarring can block the course taken by regenerating axons and establish an effective barrier against the reformation of central connections.

Degeneration spreads in both directions along the axon from the zone of trauma, but only for a short distance in the proximal segment, usually up to the point of origin of the first axon collateral. After 2-3 days, a retrograde reaction is seen in the cell body. If the entire cell body dies, then degeneration spreads from the axon hillock (the conical area of origin of the axon from the nerve cell body) down along the remainder of the proximal segment. In the distal segment, outside the zone of trauma, degeneration first appears in the axon terminal about 1 day after the occurrence of the lesion. In approximately 2 weeks, the synapses formed by the distal segment degenerate completely (terminal degeneration). Degeneration of the distal axon itself takes place over a period of 1-2 months (Wallerian degeneration). Eventually, cells that are either pre- or postsynaptic to the injured neuron also may be affected ("transneuronal degeneration"). Thus, in anterograde transneuronal degradation, neurons deprived of major input from axons that have been destroyed may atrophy. In retrograde transneuronal degradation, similar changes may occur in neurons that have lost the main recipient of their outflow.

The axon terminal is very sensitive to interruption of contact with the parent cell body. If the axon of a motor neuron to a skeletal muscle is severed by cutting a peripheral nerve, within a matter of hours degenerative changes begin to occur at the presynaptic terminals of the motor axon because the maintenance of its integrity is critically dependent on fast axonal transport. Synaptic transmission fails soon after the axon is cut, even before the first morphological signs of degeneration become evident in the synaptic terminal. The onset of transmission failure is very rapid if the axon is cut close to the synaptic terminal region, and slower if the axon is cut close to the cell body. This indicates that axonal transport continues for some time in the distal segment until the entire axon is depleted of metabolic products required for synaptic transmission.

The degenerative changes that occur in the synaptic terminal itself are similar to the changes that take place in degenerating synapses in the CNS. Within one day after axotomy, the terminal and its mitochondria begin to swell. In some cases the terminal becomes filled with swirls of neurofilaments surrounding a central packet of disrupted mitochondria. Alternatively, the terminal may become filled with more homogeneous electron-dense products of degeneration. After 6 or 7 days the terminal is pushed away from its contacts with postsynaptic neurons by invading glial cells. At the neuromuscular synapse, eventually the Schwann cells around the synaptic terminal of the motor axon de-differentiate and proliferate to form phagocytes that absorb the degenerating terminal. Soon afterward, the whole distal axon breaks up into short, beaded segments that then are phagocytosed by Schwann cells.

About one week after the initial degenerative changes appear in the axon terminal, degeneration begins in the entire distal axon. The myelin sheath draws away from the axon and breaks apart. The axon swells and then becomes beaded. Neurofilaments and neurotubules (collectively neurofibrils) soon fill the axon. Fragments of the axon and the myelin sheath are absorbed by local phagocytes derived from the glial cell population in the CNS or from Schwann cells in the PNS. In the CNS, macrophages from the general circulation do not absorb the debris produced by Wallerian degeneration, as they do in the zone of trauma.

Neuroregeneration in the PNS

Neuroregeneration in the PNS occurs to a significant degree. Injury to the PNS immediately elicits the migration of phagocytic cells, Schwann cells, and macrophages to the lesion site in order to clear away debris, such as damaged tissue. After injury, the proximal end swells and experiences some retrograde degeneration, but once the debris is cleared, it begins to sprout axons and the presence of growth cones can be detected. The proximal axons are able to regrow as long as the cell body is intact, and they have made contact with the neurolemmocytes in the endoneurial channel. Human axon growth rates can reach 2 mm per day in small nerves and 5 mm per day in large nerves. The distal segment, however, experiences Wallerian degeneration within hours of the injury; the axons and myelin degenerate, but the endoneurium (a delicate connective tissue around individual nerve fibers in a nerve bundle) remains. In the later stages of regeneration, the remaining endoneurial tube directs axon growth back to the correct targets. During Wallerian degeneration, Schwann cells grow in ordered columns along the endoneurial tube, creating a band of Bungner (boB) that protects and preserves the endoneurial channel. Also, macrophages and Schwann cells release neurotrophic factors that enhance re-growth.

The sequence of axonal degeneration in the PNS differs from the sequences that occurs in the CNS. If the peripherally directed process of a dorsal root ganglion cell is cut, or if a motor axon is cut, then the distal segment of the severed axon will degenerate. However, the connective tissue sheath that surrounds the nerve in which the severed axon ran may remain intact. In many instances, depending upon the nature of the injury, the proximal segment of a severed axon can regenerate and reconnect to its previous synaptic sites as long as its cell body remains alive. The regenerating axons run along the connective tissue sheath, which acts as a conduit leading the growing axons back to the peripheral target. Conversely, if the centrally directed branches of dorsal root ganglion cells are cut, the glial scar that forms around the degenerating axons in the dorsal aspect of the spinal cord prevents any axons that might regenerate from reaching their central targets.

There are two major ways in which the cell bodies of different classes of neurons respond to axotomy. After an axon is severed, some neurons undergo distinctive regenerative changes as they prepare metabolically for the regrowth of a new axon. For example, cutting the peripheral axon of a dorsal root ganglion cell or a spinal motor neuron causes characteristic changes in the parent neuron within 2-3 days. The cell body first begins to swell (it may double in size). The nucleus moves to an eccentric position, usually opposite the axon hillock, and also begins to swell. Finally, the rough endoplasmic reticulum (ER) breaks apart and moves to the periphery of the swollen cell body. For 1-3 weeks, the number of free polysomes in the cell body, the total amount of protein, and RNA synthesis in the nucleus increases (chromatolysis), suggesting that a massive synthesis of proteins necessary for regenerating the severed parts of the axon occurs. If the proper connections are restored after regeneration of the axon, this buildup ceases and the cell body usually regains its normal appearance. If the proper connections are not restored, the cell will atrophy or degenerate totally. The age of the animal, the site of the lesion, and the nature of the injury are important considerations in judging the potential for functional recovery after nerve section.

Neuroprotection

Neuroprotection refers to the mechanisms and/or strategies used to guard or defend against neuronal injury or degeneration in the CNS following acute disorders (such as, for example, stroke, nervous system injury or trauma) or as a result of chronic neurodegenerative diseases (such as, for example, Parkinson's disease, Alzheimer's disease, Multiple Sclerosis). Neuroprotectives (products or compounds with neuroprotective effects) can be grouped into several categories including, but not limited to, the following: free radical scavengers; anti-excitotoxic agents; apoptosis inhibitors; anti-inflammatory agents; neurotrophic factors; metal ion chelators; and ion channel modulators.

Free Radical Scavengers

A free radical is a highly reactive and usually short-lived molecular fragment with one or more unpaired electrons. Free radicals are highly chemically reactive molecules. Because a free radical needs to extract a second electron from a neighboring molecule to pair its single electron, it often reacts with other molecules, which initiates the formation of many more free radical species in a self-propagating chain reaction. This ability to be self-propagating makes free radicals highly toxic to living organisms.

Reactive oxygen species ("ROS"), such as free radicals and peroxides, represent a class of molecules that are derived from the metabolism of oxygen and exist inherently in all aerobic organisms. The term "oxygen radicals" as used herein refers to any oxygen species that carries an unpaired electron (except free oxygen). The transfer of electrons to oxygen also may lead to the production of toxic free radical species. The best documented of these is the superoxide radical. Oxygen radicals, such as the hydroxyl radical (OH—) and the superoxide ion ($O_2$-) are very powerful oxidizing agents that cause structural damage to proteins, lipids and nucleic acids. The free radical superoxide anion, a product of normal cellular metabolism, is produced mainly in mitochondria because of incomplete reduction of oxygen. The superoxide radical, although unreactive compared with many other radicals, may be converted by biological systems into other more reactive species, such as peroxyl (ROO—), alkoxyl (RO—) and hydroxyl (OH—) radicals.

Oxidative injury may lead to widespread biochemical damage within the cell. The molecular mechanisms responsible for this damage are complex. For example, free radicals may damage intracellular macromolecules, such as nucleic acids (e.g., DNA and RNA), proteins, and lipids. Free radical damage to cellular proteins may lead to loss of enzymatic function and cell death. Free radical damage to DNA may cause problems in replication or transcription, leading to cell death or uncontrolled cell growth. Free radical damage to cell membrane lipids may cause the damaged membranes to lose their ability to transport oxygen, nutrients or water to cells.

Free radical scavengers with a neuroprotective effect include, but are not limited to, 3-methyl-1-phenyl-2-pyrazolin-5-one (edaravone), and α-phenyl-n-tert-butyl-nitrone (PBN), N-tert-butyl-(2-sulfophenyl)-nitrone (S-PBN).

Anti-Excitotoxic Agents

Excitatory acidic amino acids (EAAS) constitute the major group of exitatory neurotransmitters in the mammalian brain. They serve a multitude of defined physiological functions, which are the subject of several studies. It generally is believed that EAAS play a critical role in neuronal development, learning processes and motor control. Their actions are mediated by membrane receptors, which are classically divided into three pharmacologically distinct subtypes: N-methyl-D-aspartate (NMDA), quisqualate, and kainate receptors. Further, EAAS can produce selective "axon-sparing" neuronal lesions in the CNS. The term "excitotoxicity" refers to the pathological process by which nerve cells are damaged and killed by glutamate and similar substances. This occurs when receptors for the excitatory neurotransmitter glutamate (glutamate receptors (NMDA receptors, α-amino-3-hydroxy-5-methyl-4-isoxazolepropionic acid receptor (AMPA or quisqualate receptor))) are overactivated. Excitotoxins, such as, but not limited to, NMDA and kainic acid, which bind to these receptors, and pathologically high levels of glutamate, can cause excitotoxicity by allowing high levels of calcium ions ($Ca^{2+}$) to enter the cell. $Ca^{2+}$ influx into cells activates a number of enzymes, including, but not limited to, phospholipases, endonucleases, and proteases, such as, for example, calpain. These enzymes go on to damage cell structures including, but not limited to, components of the cytoskeleton, the cell membrane, and DNA. Anti-excitotoxic agents include, but are not limited to, NMDA antagonists, phencyclidine, ketamine, (±)-SKF 10,047, pentazocine, d-aminophosphonovalerate, d-aminophosphonoheptanoate, d-α-aminoadipate, OH-quinoxaline carboxylate, kynurenate, (±)-cis-2,3-piperidine dicarboxylate, secobarbital, amobarbital and pentobarbital.

Apoptosis Inhibitors

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

It generally is believed that apoptosis contributes to neuronal cell death in a variety of neurodegenerative contexts. Activation of cysteine protease caspase-3 appears to be a key event in the execution of apoptosis in the CNS. Caspase-3 activation has been observed in stroke, spinal cord trauma, head injury and Alzheimer's disease. Some studies have shown that peptide-based caspase inhibitors can prevent neuronal loss in animal models of head injury and stroke. Further, failed caspase inhibition may have a role in spinal muscular atrophy (SMA) (a hereditary neurodegenerative disorder). In severe SMA, the neuronal specific inhibitor of apoptosis (IAP) family member known as NAIP often is dysfunctional due to missense and truncation mutations. IAPs such as NAIP potently block the enzymatic activity of group II caspases (3 and 7); NAIP mutations may permit unopposed developmental apoptosis to occur in sensory and motor systems resulting in lethal muscular atrophy (see, for example, Robertson, G. S., et al., *Brain Pathology*. 2006. 10 (2):283-292). Neuroprotective apoptosis inhibitors include, but are not limited to, boc-aspartyl(Ome)-fluoromethylketone, erythropoietin, and (R,S)-({(2S)-2-[5-tert-butyl-3-{[(4-methyl-1,2,5-oxadiazol-3-yl)methyl]amino}-2-oxopyrazin-1(2H)-yl]butanoyl}amino)-5-[hexyl(methyl)amino]-4-oxopentanoic acid bis-hydrochloride (M826).

Anti-Inflammatory Agents

A sustained inflammatory reaction is present in acute neurodegenerative disorders (such as, for example, stroke) and chronic neurodegenerative disorders (such as, for example, Alzheimer's disease, Parkinson's disease and multiple sclerosis). Inflammation, which is fostered by both residential glial cells and blood-circulating cells that infiltrate the diseased brain, probably starts as a time- and site-specific defense mechanism that could later evolve into a destructive and uncontrolled reaction. An acute neuroinflammatory response includes activation of microglia, resident tissue macrophages in the CNS and the principle mediators of neuroinflammation, resulting in phagocytosis and the release of inflammatory mediators such as cytokines and chemokines. Chronic neuroinflammation includes long-standing activation of microglia and subsequent sustained release of inflammatory mediators, which perpetuate the inflammatory cycle, activating additional microglia, promoting their proliferation, and resulting in further release of inflammatory factors. Several anti-inflammatory agents are generally believed to provide a neuroprotective effect including, but not limited to, non-steroidal anti-inflammatory drugs (NSAIDS), such as, but not limited to, aspirin, ibuprofen, indomethacin, sulindac, and flurbiprofen; estrogen; and peroxisome proliferator-activated receptor-γ (PPARs) agonists, such as, but not limited to, thiazolidinediones (TZDs).

Neurotrophic Factors

Neurotrophic factors are important regulators of the development and maintenance of vertebrate nervous systems. Neurotrophins are a unique family of polypeptide growth factors that influence the proliferation, differentiation, survival, and death of neuronal and nonneuronal cells. The effects of neurotrophins depend upon their level of availability, their binding affinity to transmembrane receptors, and the downstream signaling cascades that are stimulated after receptor activation. Neurotrophins have multiple roles in the adult nervous system including, but not limited to, regulating synaptic connections and synapse structure, neurotransmitter release and potentiation, mechanosensation, and pain and synaptic plasticity.

Many growth factors and neurotrophins can promote neuronal survival. These factors can activate several intracellular signaling transduction systems including, but not limited to, the extracellular signal-regulated kinase (ERK) and the phosphatidyl-inositol-3-OH kinase (PI 3-kinase) pathways. Studies have reported that activation of the PI 3-kinase pathway is required for (1) NGF-mediated survival of (a) the rat pheochromocytoma cell line PC12 (Greene and Tischler, 1976) (an in vitro cell culture system for studying the mechanism of NGF action) and (b) rat superiorcervical ganglion (SCG) neurons; (2) insulin-like growth factor-1-mediated survival of (a) cerebellar granule neurons, (b) oligodendrocytes, and (c) PC12 cells; and (3) for membrane depolarization-mediated survival of cerebellar granule neurons. Neuroprotective neurotrophic factors include, but are not limited to, brain-derived neurotrophic factor (BDNF), nerve-growth factor (NGF), neurotrophins 3 and 4/5, glial-derived neurotrophic factor (GDNF), and ciliary neurotrophic factor (CNTF).

Metal Ion Chelators

Metal ions are associated with metabolic processes (such as, for example, protein aggregation and oxidative stress) that are involved in several neurodegenerative disorders. Several chelators have been studied for their potential in the treatment of neurodegenerative diseases including, but not limited to, (1) hexadentate chelators, such as, for example, desferrioxamine, and a synthetic amino-carboxylate ligand (DP-109); (2) tridentate chelators, such as, for example, isonicotinoyl picolinoyl hydrazine; and (3) bidentate chelators, such as, for example, bathocuproine, feralex, and 8-hydroxyquinoline analogues.

One of the dominant properties of any therapeutic chelator is metal selectivity, typically a high selectivity being required (as with, for example, the treatment of iron overload associated with β-thalassaemia, where ligands with a high selectivity for iron over copper and zinc are essential, since chelation therapy is maintained for life). Unfortunately, the identity of the putative toxic metal is not always firmly established with many proposed treatments of neurodegenerative diseases by chelation therapy. For example, in Alzheimer's Disease, for instance, iron, copper and zinc all have been associated with the progression of the disease. Although there are clear guidelines for the design of iron-selective chelating agents (Liu & Hider, 2002), no clear guidelines exist for the design of copper and zinc selective chelating agents. Furthermore, because of the need for ready permeation of the blood-brain barrier (BBB), the size of useful chelators generally is limited to less than 300 Da, thereby excluding hexadentate ligands and seriously limiting the potential for the design of selective copper(II) and zinc(II) chelators. Any agent that binds copper(II) tightly also will bind iron(II), zinc(II), nickel(II), cobalt(II) and manganese(II), thereby causing a potential toxic insult to most cell types (Liu & Hider, 2002). This limitation is a major issue for the design of chelators potentially useful for treating neurodegeneration.

Ion Channel Modulators

Ion channels are pore-forming proteins that regulate the cell potential across the plasma membrane of all living cells; ion channels allow a flow of ions down their electrochemical gradient, i.e., from high concentration to low concentration. Ion channels are prominent components of the nervous system since "voltage-activated" channels underlie the nerve impulse, and "transmitter-activated" channels mediate conduction across the synapses. There are numerous types of ion channels that can be classified by gating (meaning by what opens and closes the channel) including (1) voltage-gated (ion channels that are reactive to membrane potential); (2) ligand-gated (ionotropic receptors that are reactive to specific ligand molecules); (3) ion gated (those channels reactive to ions such as $Cl^-$, $K^+$, $Na^+$, $Ca^{2+}$) and (4) other gating (those reactive to, for example, second messengers). Several ion channel modulators with neuroprotective effects include, but not limited to, arachidonic acid, dantrolene, tetrodotoxin, polyamines, and estradiol.

Nerve Damage and Neuropathies

Neuron injury may result in several types of neuropathy.

Diabetic Neuropathies

Diabetic neuropathies are a family of nerve disorders caused by diabetes. Patients with diabetes may, over time, develop nerve damage throughout the body, while others may present no symptoms. Symptoms include pain, tingling, or numbness, in the hands, arms, feet, and legs. Nerve problems can occur in every organ system, including the digestive tract, heart, and sex organs. Proximal neuropathy results in pain in the thighs, hips, or buttocks and leads to weakness in the legs, and focal neuropathy results in the sudden weakness of one nerve or a group of nerves, causing muscle weakness or pain.

About 60%-70% of patients with diabetes have some form of neuropathy. The risk rises with age and longer duration of diabetes. The highest rates of neuropathy are among patients who have had diabetes for at least 25 years. Diabetic neuropathies also appear to be more common in patients who have problems controlling their blood glucose, those with high levels of blood fat and blood pressure, and those who are overweight.

Peripheral Neuropathy

Peripheral neuropathy, the most common type of diabetic neuropathy, also can result from traumatic injuries, infections, metabolic disorders and exposure to toxins. In its most common form, it causes pain and numbness in a subject's hands and feet. The pain typically is described as tingling or burning, while the loss of sensation often is compared to the feeling of wearing a thin stocking or glove. In many cases, peripheral neuropathy symptoms, when caused by a treatable underlying condition, improve with time. Medications initially designed to treat other conditions, such as epilepsy and depression, often are used to reduce the painful symptoms of peripheral neuropathy.

Autonomic Peripheral Neuropathy

Autonomic neuropathy is a form of peripheral neuropathy that involves damage to the nerves that run through a part of the PNS. It is a group of symptoms, not a specific disease, and has many causes. Symptoms occur when there is damage to nerves that regulate vital functions, including heart muscle, smooth muscles, those that regulate blood pressure, heart rate, bowel and bladder emptying, digestion, and other body functions. Autonomic neuropathy causes changes in digestion, bowel and bladder function, sexual response, perspiration, can affect nerves in the lungs and eyes, and may cause hypoglycemia unawareness, a condition in which patients no longer experience the warning symptoms of low blood glucose levels. Damage to the autonomic nerves also affects the function of areas connected to the problem nerve. For example, damage to the nerves of the gastrointestinal tract makes it harder to move food during digestion (decreased gastric motility).

CNS Nerve Degeneration

Damage to neurons of CNS may lead to progressive degenerative diseases.

For example, Alzheimer's disease (AD), a progressive, degenerative brain disease that affects memory, thinking, and behavior, is characterized by loss of neurons and synapses in the cerebral cortex and certain subcortical regions, which results in gross atrophy of the affected regions, including degeneration in the temporal lobe and parietal lobe, and parts of the frontal cortex and cingulate gyms. Both amyloid plaques and neurofibrillary tangles, which are aggregates of the microtubule-associated protein tau, which has become hyperphosphorylated and accumulates inside the cells, are apparent. Although many older individuals develop some plaques and tangles as a consequence of aging, the brains of AD patients have a greater number of them in specific brain regions, such as the temporal lobe.

Amyotrophic Lateral Sclerosis

Amyotrophic lateral sclerosis (ALS) belongs to a class of disorders known as motor neuron disorders in which the motor neurons located in the brain, brainstem and spinal cord that serve as the controlling units and are vital for communication links between the nervous system and the voluntary muscles of the body are affected. The loss of these cells causes the muscles under their control to weaken and waste away, leading to paralysis. It usually is fatal within five years of diagnosis. There is no cure for ALS, nor is there a proven therapy that will prevent or reverse its course. ALS affects 30,000 U.S. residents with about 5,000 new cases occurring in the U.S. each year. In about 10% of cases, ALS is caused by a genetic defect. In other cases, the cause of the nerve degeneration is unknown.

Parkinson's Disease

Parkinson's disease is a progressive disorder of the brain in which the nerve cells in the part of the brain that controls muscle movement gradually are destroyed. Symptoms include tremor and difficulty with walking, movement, and coordination. The exact reason that the cells of the brain waste away is unknown. The disorder may affect one or both sides of the body, with varying degrees of loss of function. The disease affects approximately 2 of every 1,000 people, both men and women, and most often develops after age 50. It may occur in younger adults, but is seen rarely in children.

Spinal Cord Injury

Spinal cord injury (SCI) involves damage to the nerves within the spinal canal; most SCIs are caused by trauma to the vertebral column, thereby affecting the spinal cord's ability to send and receive messages from the brain to the body's systems that control sensory, motor and autonomic function below the level of injury. Causes of paralysis include stroke, post-polio syndrome, cerebral palsy, neurofibromatosis, traumatic brain injury, spinal cord injury, multiple sclerosis, and unspecified birth defect. Various types of accidents accounted for the great majority of SCI.

The cost of living with spinal cord injury, which can be considerable, varies greatly depending on the severity of the injury. Average yearly expenses can range from $228,566 to $775,567 in the first year. The estimated lifetime costs due to SCI can range from $691,843 to over $3 million for a 25 year old. Further, 87.9% of all SCI individuals are discharged from hospitals to private homes.

Generally, clinical treatments for nerve injury are lacking, with any nerve regeneration being modest at best. Nerve autografting (or autologous nerve grafting) has been used to treat large lesion gaps in the PNS. The procedure involves transplanting nerve segments from a donor site within a subject to another (injured) site such that endoneurial tubes for axonal regeneration across the gap are provided. However, this treatment often provides only a limited functional recovery. Additionally, partial deinnervation frequently is experienced at the donor site and multiple surgeries are required to harvest the tissue and implant it.

Several variations of nerve autografting have been attempted. These include allografts (utilizing tissue from a donor that is implanted in the subject) and xenografts (utilizing tissue from a different species). Allografts and xenografts, in addition to having the disadvantages of autografts, often require simultaneous immunosuppressive therapies to mediate the recipient subject's immunological acceptance of the foreign tissue. Further, disease transmission must be considered when introducing tissue from another person or animal.

Additional efforts to effect nerve regeneration include the fabrication and use of nerve guidance conduits to guide axonal regrowth (where the artificial nerve conduits are introduced into the lesion) and immunization. However, these treatments also are lacking in effectiveness and may be costly.

While the efforts towards regenerating nerves of the PNS have yielded sparse, if any, results, there are no effective treatments for nerve injury or methods to facilitate nerve regeneration within the CNS.

The described invention addresses this problem. It provides and EPRO compositions comprising at least one peptide of formula I for improving or enhancing neurite outgrowth, neuroprotection, and nerve regeneration, and methods of use thereof.

SUMMARY

According to one aspect, the described invention provides an EPRO composition comprising a therapeutically effective amount of a polypeptide having the amino acid sequence according to Formula I: Z1-X1-X2-X3-X4-X5-X6-X7-X8-X9-X10-Z2, wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; wherein the composition enhances neurite outgrowth; is neuroprotective, or enhances neuroregeneration following neural injury. According to one embodiment, X2, X3, X6 and X7 is any aliphatic amino acid. According to another embodiment, X4 is R, X5 is Q and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G. According to another embodiment, at least one of Z1 and Z2 is a transduction domain. According to another embodiment, the Z1 and Z2 are each independently selected from the group consisting of: (R)4-9 [SEQ ID NO: 1]; GRKKRRQR-RRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGRSAASRPTERPRAPARSASR-PRRPVE [SEQ ID NO: 6]; GWTLNSAGYLLGLINLKA-LAALAKKIL [SEQ ID NO: 7]; PLSSIFSRIGDP [SEQ ID NO: 8]; AAVALLPAVLLALLAP [SEQ ID NO: 9]; AAV-LLPVLLAAP [SEQ ID NO: 10]; VTVLALGALAGVGVG [SEQ ID NO: 11; GALFLGWLGAAGSTMGAWSQP [SEQ ID NO: 12]; GWTLNSAGYLLGLINLKALAALAK-KIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAF-AKLAARLYRAA [SEQ ID NO: 16]; AAFAKLAAAR-LYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAK-LAARLYRKAGC [SEQ ID NO: 22]; KAFAALAAR-LYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRK-KRRQRRR [SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAF-AALAARLYRKA [SEQ ID NO: 18]; KAFAKLAAR-LYRAA [SEQ ID NO: 16]; KAFAKLAARLYRA [SEQ ID NO: 19]; FAKLAARLYRAA [SEQ ID NO: 31]; and FAK-LAARLYRA [SEQ ID NO: 32]. According to another embodiment, at least one of Z1 and Z2 are selected from the group consisting of WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRK-KRRQR [SEQ ID NO: 4]; KAFAKLAARLYRKA [SEQ ID NO: 15]; FAKLAARLYRKA [SEQ ID NO: 30]; KAF-AALAARLYRKA [SEQ ID NO: 18]; KAFAKLAAR-LYRAA [SEQ ID NO: 16]; KAFAKLAARLYRA [SEQ ID NO: 19]; FAKLAARLYRAA [SEQ ID NO: 31]; and FAK-LAARLYRA [SEQ ID NO: 32]. According to another embodiment, the at least one polypeptide of formula I comprises an amino acid sequence selected from the group consisting of YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKA-LNRQLGVAA [SEQ ID NO: 56]; YARAAARQARAKALNRQLGVAA [SEQ ID NO: 51]; KAFAKLAARLYRKALNRQLAVAA [SEQ ID NO: 52]; FAKLAARLYRKALNRQLAVAA [SEQ ID NO: 53]; KAFALKAARLYRKA-LNRQLGVAA [SEQ ID NO: 57]; and FAKLAARLYRKA-LNRQLGVAA [SEQ ID NO: 58]. According to another embodiment, the at least one polypeptide of formula I of the EPRO composition is a peptide of amino sequence YARAAARQARAKALARQLGVAA ([SEQ ID NO: 33]). According to another embodiment, the at least one polypeptide of formula I of the EPRO composition is a peptide of amino acid sequence YARAAARQARAKALNRQLGVAA [SEQ ID NO: 51]. According to another embodiment, the at least one polypeptide of formula I of the EPRO composition is a peptide of amino acid sequence FAKLAARLYRKALALRQLGVAA [SEQ ID NO: 46]. According to another embodiment, the composition is a pharmaceutical composition. According to another embodiment, the composition further comprises at least one additional active agent. According to another embodiment, the composition inhibits production of at least one inflammatory cytokine following the nerve injury. According to another embodiment, the at least one inflammatory cytokine is at least one of IL-1 beta, IL-6, and TNF-alpha. According to another embodiment, the inflammatory cytokines are produced by activated microglia and astrocytes following nerve injury. According to another embodiment, the concentration of MK2i in the therapeutic composition is from 0.001 nM to less than 3 mM.

According to another aspect, the described invention provides a biomedical device comprising an EPRO composition comprising at least one polypeptide having an amino acid sequence according to Formula I: Z1-X1-X2-X3-X4-X5-X6-X7-X8-X9-X10-Z2, wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; wherein the polypeptide when disposed on or in the device enhances neurite outgrowth; is neuroprotective, or enhances neuroregeneration following neural injury. According to one embodiment, the biomedical device is selected from the group consisting of a stent, a graft, a shunt, a stent graft, a fistula, an angioplasty device, a balloon catheter, a venous catheter, an implantable drug delivery device, an adhesion barrier, a wound dressing, a hydrocolloid, a hydrogel, a foam, a hydrophilic foam, a hydrophobic foam, a calcium alginate, a cellophane, a pluronic, a biological polymer, a microelectrode, a probe, and a tissue scaffold. According to another embodiment, X2, X3, X6 and X7 is any aliphatic amino acid. According to another embodiment, X2, X3, X6 and X7 can be any aliphatic amino acid. According to another embodiment, X4 is R, X5 is Q and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G. According to another embodiment, at least one of Z1 and Z2 is a transduction domain. According to another embodiment, the Z1 and Z2 are each independently selected from the group consisting of: (R)4-9 [SEQ ID NO: 1]; GRKKRRQRRRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGRSAASRPTERPRAPARSASRPRRPVE [SEQ ID NO: 6]; GWTLNSAGYLLGLINLKALAALAK-KIL [SEQ ID NO: 7]; PLSSIFSRIGDP [SEQ ID NO: 8]; AAVALLPAVLLALLAP [SEQ ID NO: 9]; AAVLLPVL-LAAP [SEQ ID NO: 10]; VTVLALGALAGVGVG [SEQ ID NO: 11]; GALFLGWLGAAGSTMGAWSQP [SEQ ID NO: 12]; GWTLNSAGYLLGLINLKALAALAKKIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAFAK-LAARLYRAA [SEQ ID NO: 16]; AAFAKLAAARLYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAKLAAR-LYRKAGC [SEQ ID NO: 22]; KAFAALAARLYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRKKRRQRRR [SEQ ID NO: 27]; WLRRIKAWLRRIKA [SEQ ID NO: 28]; WLRRIKAWLRRIKAWLRRIKA [SEQ ID NO: 29]; FAK-LAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAAR-LYRAA [SEQ ID NO: 31]; and FAKLAARLYRA [SEQ ID NO: 32]. According to another embodiment, at least one of Z1 and Z2 are selected from the group consisting of WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRKKRRQR [SEQ ID NO: 4]; KAFAKLAARLYRKA [SEQ ID NO: 15]; FAKLAAR-LYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, the at least one polypeptide of formula I comprises an amino acid sequence selected from the group consisting of YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKALNRQLGVA [SEQ ID NO: 56]WLRRIKAWRRIKA-LNRQLGVAA; YARAAARQARAKAL-NRQLGVA [SEQ ID NO: 51]; KAFAKLAARLYRKALNRQLAVAA [SEQ ID NO: 52]; FAKLAARLYRKALNRQLAVAA [SEQ ID NO: 53]; KAFALKAARLYRKALNRQLGVA [SEQ ID NO: 57]KAFALKAARLYRKA-LNRQLGVAA; and FAKLAARLYRKALNRQLGVA [SEQ ID NO: 58]FAKLAARLYRKA-LNRQLGVAA. According to another embodiment, the EPRO composition comprising at least one polypeptide having an amino acid sequence according to Formula I is directly disposed onto the inner surface of the biomedical device. According to another embodiment, the EPRO composition comprising at least one polypeptide having an amino acid sequence according to Formula I is directly disposed onto the outer surface of the biomedical device. According to another embodiment, the EPRO composition comprising at least one polypeptide having an amino acid sequence according to Formula I is directly disposed into the biomedical device such that the at least one polypeptide is embedded into the inner surface of the biomedical device. According to another embodiment, the EPRO composition comprising at least one polypeptide having an amino acid sequence according to Formula I is directly disposed into the biomedical device such that the at least one polypeptide is embedded into the outer surface of the biomedical device. According to another embodiment, the EPRO composition comprising the at least one polypeptide having an amino acid sequence according to Formula I is disposed in a matrix. According to another embodiment, the EPRO composition comprising at least one polypeptide having an amino acid sequence according to Formula I, is indirectly dispersed onto or into the biomedical device, and enhances outgrowth of at least one neurite process from a neuron cell body. According to another embodiment, the at least one polypeptide having an amino acid sequence according to Formula I inhibits production of at least one inflammatory cytokine following the nerve injury. According to another embodiment, the at least one inflammatory cytokine is at least one of IL-1 beta, IL-6, and TNF-alpha. According to another embodiment, the inflammatory cytokines are produced by activated microglia and astrocytes following nerve injury. According to another embodiment, the concentration of MK2i in the therapeutic composition is from 0.001 nM to less than 3 mM.

According to another aspect, the described invention provides a method for improving or enhancing neurite outgrowth, the method comprising: (a) providing a therapeutically effective amount of an EPRO composition, the EPRO composition comprising: (i) at least one polypeptide having an amino acid sequence according to Formula I: Z1-X1-X2-X3-X4-X5-X6-X7-X8-X9-X10-Z2, wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; wherein the polypeptide enhances or improves outgrowth of at least one neurite process from a neuron cell body; and (ii) a carrier; (b) administering the EPRO composition to a subject in need thereof; and (c) increasing neurite outgrowth relative to neurite outgrowth of a neuron that has not been treated with the EPRO composition. According to one embodiment, X2, X3, X6 and X7 is any aliphatic amino acid. According to another embodiment, X4 is R, X5 is Q and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G. According to another embodiment, at least one of Z1 and Z2 is a transduction domain. According to another embodiment, the Z1 and Z2 are each independently selected from the group consisting of: (R)4-9 [SEQ ID NO: 1]; GRKKRRQRRRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGR-SAASRPTERPRAPARSASRPRRPVE [SEQ ID NO: 6]; GWTLNSAGYLLGLINLKALAALAKKIL [SEQ ID NO: 7]; PLSSIFSRIGDP [SEQ ID NO: 8]; AAVALLPAVLLAL-LAP [SEQ ID NO: 9]; AAVLLPVLLAAP [SEQ ID NO: 10]; VTVLALGALAGVGVG [SEQ ID NO: 11; GALFL-GWLGAAGSTMGAWSQP [SEQ ID NO: 12]; GWTLN-SAGYLLGLINLKALAALAKKIL [SEQ ID NO: 7]; KLA-LKLALKALKAALKLA [SEQ ID NO: 13]; KETWWETWWTEWSQPKKKRKV [SEQ ID NO: 14]; KAFAKLAARLYRKA [SEQ ID NO: 15]; KAFAKLAARLYRAA [SEQ ID NO: 16]; AAFAKLAAARLYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAKLAARLYRKAGC [SEQ ID NO: 22]; KAFAALAARLYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRKKRRQRRR [SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAFAALAARLYRKA [SEQ ID NO: 18]; KAFAKLAARLYRAA [SEQ ID NO:

16]; KAFAKLAARLYRA [SEQ ID NO: 19]; FAKLAAR-LYRAA [SEQ ID NO: 31]; and FAKLAARLYRA [SEQ ID NO: 32]. According to another embodiment, at least one of Z1 and Z2 are selected from the group consisting of WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRKKRRQR [SEQ ID NO: 4]; KAFAKLAARLYRKA [SEQ ID NO: 15]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32]. According to another embodiment, the at least one polypeptide of formula I comprises an amino acid sequence selected from the group consisting of YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKALNRQLGVA [SEQ ID NO: 56] WLRRIKAWRRIKA-LNRQLGVAA; YARAAARQARAKALNRQLGVA [SEQ ID NO: 51]; KAFAKLAARLYRKALNRQLAVAA [SEQ ID NO: 52]; FAKLAARLYRKALNRQLAVAA [SEQ ID NO: 53]; KAFALKAARLYRKALNRQLGVA [SEQ ID NO: 57]KAFALKAARLYRKA-LNRQLGVAA; and FAKLAARLYRKALNRQLGVA [SEQ ID NO: 58]FAKLAARLYRKA-LNRQLGVAA. According to another embodiment, the composition is a pharmaceutical composition. According to another embodiment, the composition further comprises at least one additional active agent. According to another embodiment, the at least one polypeptide has an amino acid sequence of 70% substantial identity to a polypeptide having an amino acid sequence according to Formula I, wherein the polypeptide having an amino acid sequence according to Formula I enhances outgrowth of at least one neurite process from a neuron cell body. According to another embodiment, the neurite process is an axon. According to another embodiment, the neurite process is a dendrite. According to another embodiment, outgrowth of the neurite process is increased at least 10% in length relative to at least one dendrite of the neurite process that has not been treated with the EPRO composition. According to another embodiment, the composition further comprises at least one additional active agent. According to another embodiment, the carrier is a pharmaceutically acceptable carrier. According to another embodiment, the EPRO composition comprising at least one polypeptide having an amino acid sequence according to Formula I inhibits production of at least one inflammatory cytokine following the nerve injury. According to another embodiment, the at least one inflammatory cytokine is at least one of IL-1 beta, IL-6, and TNF-alpha. According to another embodiment, the inflammatory cytokines are produced by activated microglia and astrocytes following nerve injury. According to another embodiment, the concentration of MK2i in the therapeutic composition is from 0.001 nM to less than 3 mM.

According to another aspect, the described invention provides a method for improving or enhancing nerve regeneration, the method comprising: (a) providing a therapeutically effective amount of an EPRO composition, the composition comprising: (i) at least one polypeptide having an amino acid sequence according to Formula I: $Z1-X1-X2-X3-X4-X5-X6-X7-X8-X9-X10-Z2$, wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; and (ii) a carrier; (b) administering the EPRO composition to a subject in need thereof; and (c) increasing neurite regrowth relative to regrowth of a neurite process of a neuron that has not been treated with the EPRO composition. According to one embodiment, X2, X3, X6 and X7 is an aliphatic amino acid. According to another embodiment, X4 is R, X5 is Q and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G. According to another embodiment, at least one of Z1 and Z2 is a transduction domain. According to another embodiment, the Z1 and Z2 are each independently selected from the group consisting of: (R)4-9 [SEQ ID NO: 1]; GRKKRRQRRRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGRSAASRPTERPRAPARSASRPRRPVE [SEQ ID NO: 6]; GWTLNSAGYLLGLINLKALAALAKKIL [SEQ ID NO: 7]; PLSSIFSRIGDP [SEQ ID NO: 8]; AAVALLPAVLLALLAP [SEQ ID NO: 9]; AAVLLPVLLAAP [SEQ ID NO: 10]; VTVLALGALAGVGVG [SEQ ID NO: 11]; GALFLGWLGAAGSTMGAWSQP [SEQ ID NO: 12]; GWTLNSAGYLLGLINLKALAALAKKIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAFAKLAARLYRAA [SEQ ID NO: 16]; AAFAKLAAARLYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAKLAARLYRKAGC [SEQ ID NO: 22]; KAFAALAARLYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRKKRRQRRR

[SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32]. According to another embodiment, at least one of Z1 and Z2 are selected from the group consisting of WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRKKRRQR [SEQ ID NO: 4]; KAFAKLAARLYRKA [SEQ ID NO: 15]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32]. According to another embodiment, the at least one polypeptide of formula I comprises an amino acid sequence selected from the group consisting of YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKALNRQLGVA [SEQ ID NO: 56]; YARAAARQARAKALNRQLGVA [SEQ ID NO: 51]; KAFAKLAARLYRKALNRQLAVAA [SEQ ID NO: 52]; FAKLAARLYRKALNRQLAVAA [SEQ ID NO: 53]; KAFALKAARLYRKALNRQLGVA [SEQ ID NO: 57]; and FAKLAARLYRKALNRQLGVA [SEQ ID NO: 58]. According to another embodiment, the at least one polypeptide has an amino acid sequence of at least 70% sequence identity to an amino acid sequence according to Formula I, wherein the at least one polypeptide having an amino acid sequence according to Formula I enhances regrowth of at least one neurite process from a neuron cell body. According to another embodiment, the at least one polypeptide is a polypeptide having amino acid sequence YARAAARQARAKALARQLGVAA [SEQ ID NO: 33]. According to another embodiment, the regrowth of the neurite process is increased at least 10% in length relative to at least one dendrite of the neurite process that has not been treated with the EPRO composition. According to another embodiment, the EPRO composition increases neurite regrowth by inhibiting expression of at least one inflammatory cytokine from activated microglia. According to another embodiment, the at least one inflammatory cytokine is at least one of IL-1 beta, IL-6, and TNF-alpha. According to another embodiment, the at least one inflammatory cytokine is produced by activated microglia and astrocytes following nerve injury.

According to another embodiment, the concentration of MK2i in the therapeutic composition is from 0.001 nM to less than 3 mM.

According to another aspect, the described invention provides a method for protecting against progression of a neuronal injury, the method comprising: (a) providing a therapeutically effective amount of a EPRO composition, the composition comprising: (i) at least one polypeptide having an amino acid sequence according to Formula I: Z1-X1-X2-X3-X4-X5-X6-X7-X8-X9-X10-Z2, wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; and (ii) a carrier; (b) administering the composition to a subject in need thereof; and (c) reducing or inhibiting at least one manifestation of progression of the neuronal injury in at least one neuronal cell population affected by the neuronal injury; and (d) increasing survival of the at least one neuronal cell population affected by the neuronal injury. According to one embodiment, the neuronal injury is a neurapraxia type injury. According to another embodiment, the injury is a axonotmesis type injury. According to another embodiment, the injury is a neurtmesis type injury. According to another embodiment, the injury results from an acute disorder. According to another embodiment, the acute disorder is a stroke, a spinal cord injury, or a traumatic brain injury. According to another embodiment, the injury results from a chronic neurodegenerative disease. According to another embodiment, the chronic neurodegenerative disease is Parkinson's disease, Alzheimer's disease, Multiple Sclerosis, Amyotrophic lateral sclerosis. or a neuropathy. According to another embodiment, the neuropathy is a diabetic neuropathy. According to another embodiment, the at least one manifestation of progression of the neuronal injury in at least one neuronal cell population is apoptotic cell death. According to another embodiment, the at least one manifestation of progression of the neuronal injury in at least one neuronal cell population is microglial activation. According to another embodiment, the at least one manifestation of progression of the neuronal injury in at least one neuronal cell population is inflammation. According to another embodiment, the at least one manifestation of progression of the neuronal injury in at least one neuronal cell population is formation of a scar. According to another embodiment, the neuronal cell population is a cortical cell population. According to another embodiment, the neuronal cell population is a mixed cortical cell population. According to another embodiment, the mixed cortical cell population comprises neurons, microglia, and astrocytes. According to another embodiment, X2, X3, X6 and X7 is an aliphatic amino acid. According to another embodiment, X4 is R; X5 is Q, and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G. According to another embodiment, at least one of Z1 and Z2 is a transduction domain selected from the group consisting of: (R)4-9 [SEQ ID NO: 1]; GRKKRRQRRRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGRSAASRPTERPRAPARSASRPRRPVE [SEQ ID NO: 6]; GWTLNSAGYLLGLINLKALAALAKKIL [SEQ ID NO: 7]; PLSSIFSRIGDP [SEQ ID NO: 8]; AAVALLPAVLLALLAP [SEQ ID NO: 9]; AAVLLPVLLAAP [SEQ ID NO: 10]; VTVLALGALAGVGVG [SEQ ID NO: 11; GALFLGWLGAAGSTMGAWSQP [SEQ ID NO: 12]; GWTLNSAGYLLGLINLKALAALAKKIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAFAKLAARLYRAA [SEQ ID NO: 16]; AAFAKLAAARLYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAKLAARLYRKAGC [SEQ ID NO: 22]; KAFAALAARLYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRKKRRQRRR [SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32]. According to another embodiment, one or both of Z1 and Z2 are selected from the group consisting of: WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRKKRRQR [SEQ ID NO: 4]; KAFAKLAARLYRKA [SEQ ID NO: 15]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32]. According to another embodiment, the at least one polypeptide of formula I comprises YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKALNRQLGVA [SEQ ID NO: 56]; YARAAARQARAKALNRQLGVA [SEQ ID NO: 51]; KAFAKLAARLYRKALNRQLAVAA [SEQ ID NO: 52]; FAKLAARLYRKALNRQLAVAA [SEQ ID NO: 53]; KAFALKAARLYRKALNRQLGVA [SEQ ID NO: 57]; and FAKLAARLYRKALNRQLGVA [SEQ ID NO: 58]. According to another embodiment, the at least one polypeptide of formula I of the EPRO composition is a peptide of amino sequence YARAAARQARAKALARQLGVAA [SEQ ID NO: 33]. According to another embodiment, the at least one polypeptide of formula I of the EPRO composition is a peptide of amino acid sequence YARAAARQARAKALNRQLGVA [SEQ ID NO: 51]. According to another embodiment, the at least one polypeptide of formula I of the EPRO composition is a peptide of amino acid sequence FAKLAARLYRKALARQLGVAA [SEQ ID NO: 46]. According to another embodiment, the at least one polypeptide has at least about 70% sequence identity to amino acid sequence YARAAARQARAKALARQLGVAA [SEQ ID NO: 33]. According to another embodiment, the at least one polypeptide has at least about 70% sequence identity to amino acid sequence YARAAARQARAKALNRQLGVA [SEQ ID NO: 51]. According to another embodiment, the at least one polypeptide has at least about 70% sequence identity to amino acid sequence FAKLAARLYRKALARQLGVAA [SEQ ID NO: 46]. According to another embodiment, the EPRO composition protects at least one neuron from progression of a neuronal injury by inhibiting expression of at least one inflammatory cytokine from activated microglia. According to another embodiment, the at least one inflammatory cytokine is at least one of IL-1 beta, IL-6, and TNF-alpha.

BRIEF DESCRIPTION OF THE DRAWINGS

FIG. 1 shows a graph of mean neurite length (μm) of control neurites (cultured 24 hours then exposed for 5 hours regular media) and exposed neurites (cultured for 24 hours then exposed to 100 mM MK2i).

FIG. 10 shows a graph of myeloperoxidase enzyme (MPO) activity (units/protein) from 0.9% NaCl, MK2i 500 μM, MK2i 50 μM, MK2i 5 μM, and control.

DETAILED DESCRIPTION

Glossary

Figure 2A:
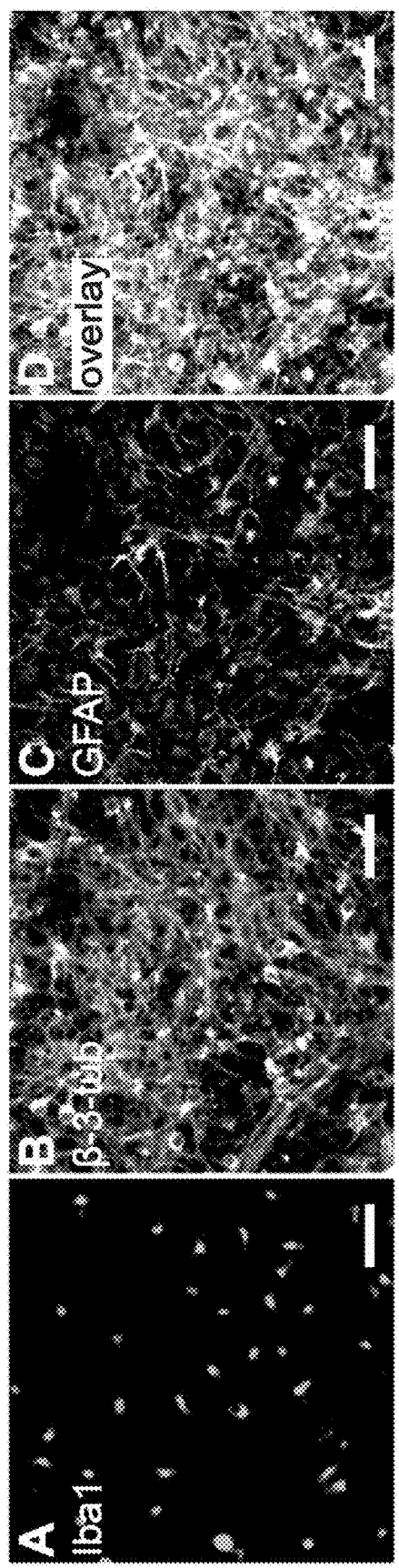
FIGS. 2A and 2B shows micrographs of neurons, astrocytes, and microglia stained with antibodies against cell-type specific proteins corresponding to neuron (β-3-tub), microglia (Iba1), and astrocyte (GFAP) in the mixed cortical culture. Cell nuclei and brightfield transmission light images (Trans) also were taken, with nuclei labeled using the DNA dye Hoechst 33342. Cultures were imaged under laser confocal using a wide aperture (400 μm). Scale bar 50 μm for FIG. 2A and 100 μm for FIG. 2B.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Gutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The phrase "additional active agent" refers to an agent, other than a compound of the inventive composition, that exerts a pharmacological, or any other beneficial activity. Such additional active agents include, but are not limited to, an antifungal agent, an antibiotic, an antiviral agent, an antiprotozoal agent, an anesthetic agent, a chemotherapeutic agent, a vitamin, a hormone and a steroid.

The terms "administering" or "administration" as used herein are used interchangeably to mean the giving or applying of a substance and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally. The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

Additional administration may be performed, for example, intravenously, pericardially, orally, via implant, transmucosally, transdermally, intramuscularly, subcutaneously, intraperitoneally, intrathecally, intralymphatically, intralesionally, or epidurally. Administering can be performed, for example, once, a plurality of times, and/or over one or more extended periods.

The meanings for anatomical positions as used herein are as follows. When referring to animals that typically have one end with a head and mouth, with the opposite end often having the anus and tail, the head end is referred to as the "cranial end," while the tail end is referred to as the "caudal end." Within the head itself, "rostral" refers to the direction toward the end of the nose, and "caudal" is used to refer to the tail direction. The surface or side of an animal's body that is normally oriented upwards, away from the pull of gravity, is the "dorsal" side; the opposite side, typically the one closest to the ground when walking on all legs, swimming or flying, is the "ventral" side. On the limbs or other appendages, a point closer to the main body is "proximal"; a point farther away is "distal." Three basic reference planes are used in zoological anatomy: (1) a "sagittal" plane divides the body into left and right portions, (2) the "midsagittal" plane is in the midline, i.e. it would pass through midline structures such as the spine, and all other sagittal planes are parallel to it, and (3) a "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called "medial" and those near the sides of animals are called "lateral." Therefore, medial structures are closer to the midsagittal plane, lateral structures are further from the midsagittal plane. Structures in the midline of the body are median. For example, the tip of a human subject's nose is in the median line. "Ipsilateral" means on the same side, "contralateral" means on the other side and bilateral means on both sides. Structures that are close to the center of the body are proximal or central, while ones more distant are distal or peripheral. For example, the hands are at the distal end of the arms, while the shoulders are at the proximal ends.

The term "anesthetic agents" as used herein refers to agents that resulting in a reduction or loss of sensation. Non-limiting examples of anesthetic drugs that are suitable for use in the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

The term "anti-fungal agent" as used herein means any of a group of chemical substances having the capacity to inhibit the growth of or to destroy fungi. Anti-fungal agents include, but are not limited to, Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconazole, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

The term "anti-protozoal agent" as used herein means any of a group of chemical substances having the capacity to inhibit the growth of or to destroy protozoans used chiefly in the treatment of protozoal diseases. Examples of antiprotozoal agents, without limitation, include pyrimethamine (Daraprim®) sulfadiazine, and Leucovorin.

The term "anti-viral agent" as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscarnet, Indinavir, Interferons (e.g., IFN-alpha), Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid.

The term "associate" or any of its grammatical forms as used herein refers to joining, connecting, or combining to, either directly, indirectly, actively, inactively, inertly, non-inertly, completely or incompletely.

The term "axon" as used herein refers to the usually long process of a nerve fiber that generally conducts impulses away from the body of the nerve cell.

The term "biomedical device" as used herein refers to an instrumentality to be implanted into or onto a subject in order to bring about a desired result. Examples of biomedical devices, include, but are not limited to, stents, grafts, shunts, stent grafts, fistulas, angioplasty devices, balloon catheters, venous catheters, implantable drug delivery devices, adhesion barriers, wound dressings, hydrocolloids, hydrogels, foams, hydrophilic foams, hydrophobic foams, calcium alginates, cellophane, pluronics, biological polymers, microelectrodes, probes, and tissue scaffolds.

The terms "carrier" and "pharmaceutical carrier" as used herein refer to a pharmaceutically acceptable inert agent or vehicle for delivering one or more active agents to a mammal, and often is referred to as "excipient."

The term "cell body" as used herein refers to the metabolic center of a neuron. Three organelles are characteristic of the cell body: the nucleus, the endoplasmic reticulum, and the Golgi apparatus. The cell body usually gives rise to several fine arborizing outgrowths or extensions called dendrites. The cell body also gives rise to the axon.

The term "chemotherapeutic agent" refers to chemicals useful in the treatment or control of a disease. Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

The term "condition" as used herein refers to a variety of health states and is meant to include disorders or diseases caused by any underlying mechanism or disorder, injury, and the promotion of healthy tissues and organs.

The term "contact" as used herein refers to a state or condition of touching or of being in immediate or local proximity. The term "contacting" as used herein refers to bringing or putting in contact, or to being in or coming into contact. Contacting a composition to a target destination, such as, but not limited to, an organ, tissue, cell, or tumor, may occur by any means of administration known to the skilled artisan.

The term "controlled release" is intended to refer to any drug-containing formulation in which the manner and profile of drug release from the formulation are regulated.

The term "controllable regulatory element" as used herein refers to nucleic acid sequences capable of effecting the expression of the nucleic acids, or the peptide or protein product thereof. Controllable regulatory elements may be operably linked to the nucleic acids, peptides, or proteins of the present invention. The controllable regulatory elements, such as, but not limited to, control sequences, need not be contiguous with the nucleic acids, peptides, or proteins whose expression they control as long as they function to direct the expression thereof. Thus, for example, intervening untranslated yet transcribed sequences may be present between a promoter sequence and a nucleic acid of the present invention and the promoter sequence may still be considered "operably linked" to the coding sequence. Other such control sequences include, but are not limited to, polyadenylation signals, termination signals, and ribosome binding sites.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "dendrite" as used herein refers to a branched protoplasmic outgrowth or extension of a nerve cell that conducts impulses from adjacent cells inward toward the cell body. A single nerve may possess many dendrites.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release." For example, delayed absorption of a parenterally administered drug form may be accomplished by dissolving or suspending the drug in an oil vehicle.

The term "disease" or "disorder" as used herein refers to an impairment of health or a condition of abnormal functioning.

The term "disposed" as used herein means to place, set or arrange in a particular order.

The term "drug" as used herein refers to a therapeutic agent or any substance, other than food, used in the prevention, diagnosis, alleviation, treatment, or cure of disease.

The term "EPRO composition" as used herein refers to a composition of the described invention, which, when used in a therapeutically effective amount, provides at least one of the following long term effects: enhanced neurite outgrowth; neuroprotection, or enhanced neural regeneration. For example, an EPRO composition can be a neurite outgrowth enhancing composition, a neuroprotective composition, or a nerve regeneration enhancing composition. The phrase "nerve regeneration enhancing composition" as used herein refers to a composition that enhances nerve regeneration of at least nerve process from a neuron cell body. The term "neurite outgrowth enhancing composition" as used herein refers to a composition that enhances outgrowth of at least one neurite process from a neuron cell body. The term "neuroprotective composition" as used herein refers to a composition that protects at least one neuron from progression of a neuronal injury.

The term "enhance" as used herein refers to an increase or intensify in quality or quantity; to make better or augment.

The term "graft" as used herein means a transplantation of a portion of living or artificial tissue from one part of a subject to another, or from one subject to another, and refers to both natural and prosthetic grafts and implants. Grafts include, but are not limited to, vascular grafts and stent grafts.

The term "growth" as used herein refers to a process of becoming larger, longer or more numerous, or an increase in size, number, or volume of cells in a cell population.

The term "hormone" as used herein refers to natural substances produced by organs of the body that travel by blood to trigger activity in other locations or their synthetic analogs. Suitable hormones for use in the context of the present invention include, but are not limited to, calciferol (Vitamin D3) and its products, androgens, estrogens and progesterones.

The term "hybridization" refers to the binding of two single stranded nucleic acid molecules to each other through base pairing. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. The effects of base incompatibility may be measured by quantifying the rate at which two strands anneal; this may provide information as to the similarity in base sequence between the two strands being annealed.

The term "hydrate" as used herein refers to a compound formed by the addition of water or its elements to another molecule. The water usually is split off by heat, yielding the anhydrous compound.

The term "implant" refers to any device or material inserted or placed, permanently or temporarily, into or onto a subject and used for the administration or delivery of a therapeutic agent(s) or substance.

The term "increase" and its various grammatical forms as used herein refers to adding to, augmenting, making or becoming greater, as in number, size, strength, or quality.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity.

The terms "inhibiting", "inhibit" or "inhibition" as used herein are used to refer to reducing the amount or rate of a process, to stopping the process entirely, or to decreasing, limiting, or blocking the action or function thereof. Inhibition may include a reduction or decrease of the amount, rate, action function, or process by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99% when compared to a reference substance, wherein the reference substance is a substance that is not inhibited.

The term "injury" as used herein refers to damage or harm to a structure or function of the body caused by an outside agent or force, which may be physical or chemical.

The term "isolated" refers to a material, such as a nucleic acid, a peptide, or a protein, which is: (1) substantially or essentially free from components that normally accompany or interact with it as found in its naturally occurring environment. The terms "substantially or essentially free" are used to refer to a material, which is at least 80% free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (for example, a promoter) becomes isolated if it is introduced by non-naturally occurring means to a locus of the genome not native to that nucleic acid. Nucleic acids that are "isolated" as defined herein are inclusive of those termed "heterologous" nucleic acids.

The term "long-term" release, as used herein, means that an implant is constructed and arranged to deliver therapeutic levels of the active ingredient for at least 7 days, or for about 30 to about 60 days.

The term "macrophage" as used herein refers to a mononuclear, actively phagocytic cell arising from monocystic stem cells in the bone marrow. These cells are widely distributed in the body and vary in morphology and motility. Phagocytic activity is typically mediated by serum recognition factors, including certain immunoglobulins and components of the complement system, but also may be non-specific. Macrophages also are involved in both the production of antibodies and in cell-mediated immune responses, particularly in presenting antigens to lymphocytes. They secrete a variety of immunoregulatory molecules.

The term "mammalian cell" as used herein refers to a cell derived from an animal of the class Mammalia. As used herein, mammalian cells may include normal, abnormal and transformed cells. Examples of mammalian cells utilized within the present invention, include, but are not limited to, neurons, epithelial cells, muscle cells, blood cells, immune cells, stem cells, osteocytes, endothelial cells and blast cells. Cells may be utilized in vivo or in vitro.

The term "manifestation" as used herein refers to a perceivable or evident materialization of a disease, disorder, condition or injury.

The term "microglia" as used herein refers to the smallest of the glial cells that can act as phagocytic cells, cleaning up CNS debris. They are considered to be a type of immune cell found in the brain. Microglia are close cousins of other phagocytic cells including macrophages and dendritic cells. Like macrophages, microglia are derived from myeloid progenitor cells from the bone marrow. During embryonic development, these cells migrate to the CNS where they differentiate into microglia.

The term "modulate" as used herein means to regulate, alter, adapt, or adjust to a certain measure or proportion.

The term "neurite" as used herein refers to any projection or process from the cell body of a neuron.

The term "neuron" as used herein refers to a specialized, impulse-conducting cell that is the functional unit of the nervous system, comprising the cell body and its processes, the axon and dendrites.

The term "neuropathy" as used herein refers to a diseased condition of the nervous system.

The term "non-steroidal anti-inflammatory agents" refers to a large group of agents that are aspirin-like in their action, including, but not limited to, ibuprofen, naproxen sodium, and acetaminophen. Additional examples of non-steroidal anti-inflammatory agents that are usable in the context of the present invention include, without limitation, oxicams, such as piroxicam, isoxicam, tenoxicam, sudoxicam, and CP-14, 304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents.

The term "nucleic acid" as used herein refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" as used herein refers to a chemical compound that consists of a heterocyclic base, a sugar, and one or more phosphate groups. In the most common nucleotides the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. The purines include adenine (A), and guanine (G); the pyrimidines include cytosine (C), thymine (T), and uracil (U).

The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, are contiguous and in the same reading frame.

The term "outgrowth" as used herein refers to an extension or projection from a neuron cell body.

The term "particles" as used herein refers to nanoparticles or microparticles (or in some instances larger) that may contain in whole or in part the EPRO composition.

The term "peptide" as used herein refers to a polymer formed from the linking together, in a defined order, of amino acids. The link between one amino acid residue and the next is known as an amide or peptide bond. By some conventions, for example, a peptide is a short polymer, of at least 2 amino acids, a "polypeptide" is a single chain of amino acids, and a "protein" contains one or more polypeptides. The term peptide as used herein is inclusive of a polypeptide, a protein or a peptidomimetic. These terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms polypeptide, peptide and protein also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The term "peptidomimetic" as used herein refers to a small protein-like chain designed to mimic a peptide. A peptidomimetic typically arises from modification of an existing peptide in order to alter the molecule's properties.

The term "pharmaceutical composition" as used herein refers to a composition that is employed to prevent, reduce in intensity, cure or otherwise treat a target condition, syndrome, disorder or disease.

The term "pharmaceutically acceptable carrier" as used herein refers to one or more compatible solid or liquid filler, diluents or encapsulating substances which are suitable for administration to a human or other vertebrate animal.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio.

The term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The term "process" as used herein refers to a prolongation or projection from a nerve's cell body, and includes axons and dendrites.

The term "progression" as used herein refers to moving forward or increasing in severity, intensity, or growth.

The term "reduce" or "reducing" as used herein refers to a decrease in size; a slowing of the growth or proliferative rate; a lowering in degree, or intensity; or to limiting the occurrence of a disorder in individuals at risk of developing the disorder.

The term "regenerate" or "regeneration" means regrowth of a lost or damaged part so that the original function is restored.

The term "regulatory sequence" (also referred to as a "regulatory region" or "regulatory element") refers to a promoter, enhancer or other segment of DNA where regulatory proteins, such as transcription factors, bind preferentially to control gene expression and thus protein expression.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information (http://www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters may be employed alone or in combination.

As used herein, "sequence identity" or "identity" in the context of two nucleic acid or polypeptide sequences refers to the residues in the two sequences which are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) relative to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The term "steroidal anti-inflammatory agent", as used herein, refers to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

The term "solvate" as used herein refers to a complex formed by the attachment of solvent molecules to that of a solute.

The term "solvent" refers to a substance capable of dissolving another substance (termed a "solute") to form a uniformly dispersed mixture (solution).

The term "specifically hybridizes" as used herein refers to the process whereby a nucleic acid distinctively or definitively forms base pairs with complementary regions of at least one strand of DNA that was not originally paired to the nucleic acid. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 85% sequence identity, at least 90% sequence identity, at least 95% sequence identity, or at least 100% sequence identity (i.e., complementary) with each other.

The term "stent" as used herein refers to a slender thread, rod or catheter inserted into a tubular structure to provide support. Stents may be used to provide support to a blood vessel, or to immobilize or hold in place a surgical graft.

The term "subject" or "individual" or "patient" are used interchangeably to refer to a member of an animal species of mammalian origin, including but not limited to, a mouse, a rat, a cat, a goat, sheep, horse, hamster, ferret, pig, a dog, a guinea pig, a platypus, a rabbit and a primate, such as, for example, a monkey, ape, or human.

The term "survival" as used herein refers to a state of remaining alive and biologically functional in spite of some threat, hardship, adversity or occurrence.

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period.

The term "syndrome" as used herein refers to a pattern of symptoms indicative of some disease or condition.

The terms "topical administration" and "topically applying" as used herein are used interchangeably to refer to delivering a peptide, a nucleic acid, or a vector comprising the peptide or the nucleic acid onto one or more surfaces of a tissue or cell, including epithelial surfaces. Although topical administration, in contrast to transdermal administration, generally provides a local rather than a systemic effect, the terms "topical administration" and "transdermal administration" as used herein, unless otherwise stated or implied, are used interchangeably.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein. An active agent includes, but is not limited to, a nerve regeneration enhancing composition, neurite outgrowth enhancing composition, or a neuroprotective composition.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$ which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The term "therapeutically effective amount" or an "amount effective" of one or more of the active agents of the present invention is an amount that is sufficient to provide a therapeutic effect. Generally, an effective amount of the active agents that can be employed ranges from about 0.000001 mg/kg body weight to about 100 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods.

The terms "transduction," or "transduce" as used herein are used interchangeably to refer to the process of crossing biological membranes. The crossing of biological membranes may be from one cell to another, from the extracellular environment to the intracellular environment, or across a cell membrane or nuclear membrane. Materials that may undergo transduction include, but are not limited to, proteins, fusion proteins, peptides, polypeptides, amino acids, viral DNA, and bacterial DNA.

As used herein, the term "transduction domain" means one or more polypeptide or any other molecule that can carry the active domain across cell membranes. These domains can be linked to other polypeptides to direct movement of the linked polypeptide across cell membranes. In some cases the transducing molecules do not need to be covalently linked to the active polypeptide.

The term "treat" or "treating" as used herein refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and (e) limiting recurrence of symptoms in patients that were previously symptomatic for the disorder. The term "treat" or "treating" also includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms.

The term "vitamin" as used herein, refers to any of various organic substances essential in minute quantities to the nutrition of most animals act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

1. Peptides

The described invention provides EPRO compositions. According to one aspect, an EPRO composition comprises a therapeutically effective amount of a polypeptide having an amino acid sequence according to Formula I:

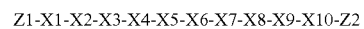

$$Z1-X1-X2-X3-X4-X5-X6-X7-X8-X9-X10-Z2$$

wherein Z1 and Z2 are independently absent or are transduction domains; X1 is selected from the group consisting of A, KA, KKA, KKKA and RA, or is absent;

X2 is selected from the group consisting of G, L, A, V, I, M, Y, W and F, or is an aliphatic amino acid;

X3 is selected from the group consisting of V, L, I, A, G, Q, N, S, T and C, or is an aliphatic amino acid;

X4 is selected from the group consisting of Q, N, H, R and K;

X5 is selected from the group consisting of Q and N;

X6 is selected from the group consisting of C, A, G, L, V, I, M, Y, W and F or is an aliphatic amino acid;

X7 is selected from the group consisting of S, A, C, T and G or is an aliphatic amino acid;

X8 is selected from the group consisting of V, L, I and M;

X9 is absent or is any amino acid;

X10 is absent or is any amino acid;

wherein at least one of the following is true:
(a) X3 is N and X7 is not G;
(b) X7 is G and X3 is not N;
(c) X2 is not L;
(d) X4 is not R;
(e) X5 is not Q;
(f) X6 is not L;
(g) X8 is not V;
(h) X10 is absent;
(i) X9 and X10 are absent;

wherein the polypeptide provides a long term beneficial neuronal effect.

According to one embodiment, the long term beneficial neuronal effect is improved or enhanced neurite outgrowth.

According to another embodiment, the long term beneficial neuronal effect is neuroprotection.

According to another embodiment, the long term beneficial neuronal effect is improved or enhanced neural regeneration.

According to another embodiment, in addition to the recited amino acids, X2, X3, X6 and X7 can be any aliphatic amino acid (whether naturally occurring or not), including, but not limited to, beta-alanine and 2-aminocyclohexane-1-carboxylic acid.

According to another embodiment, X4 is R; X5 is Q, and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G.

According to another embodiment, at least one of Z1 and Z2 is a transduction domain.

According to another embodiment, the transduction domain is linked to the rest of the polypeptide via peptide bonding. (See, for example, Cell 55: 1179-1188, 1988; Cell 55: 1189-1193, 1988; Proc Natl Acad Sci USA 91: 664-668, 1994; Science 285: 1569-1572, 1999; J Biol Chem 276: 3254-3261, 2001; and Cancer Res 61: 474-477, 2001, each of which is incorporated in their entirety herein by reference).

According to another embodiment, the transduction domain(s) is/are selected from the group consisting of:

| | |
|---|---|
| (R)4-9; | [SEQ ID NO: 1] |
| GRKKRRQRRRPPQ; | [SEQ ID NO: 2] |
| RQRRKKRG; | [SEQ ID NO: 3] |
| GRKKRRQR; | [SEQ ID NO: 4] |
| AYARAAARQARA; | [SEQ ID NO: 5] |
| DAATATRGRSAASRPTERPRAPARSASRPRRPVE; | [SEQ ID NO: 6] |
| GWTLNSAGYLLGLINLKALAALAKKIL; | [SEQ ID NO: 7] |
| PLSSIFSRIGDP; | [SEQ ID NO: 8] |
| AAVALLPAVLLALLAP; | [SEQ ID NO: 9] |
| AAVLLPVLLAAP; | [SEQ ID NO: 10] |
| VTVLALGALAGVGVG; | [SEQ ID NO: 11] |
| GALFLGWLGAAGSTMGAWSQP; | [SEQ ID NO: 12] |
| GWTLNSAGYLLGLINLKALAALAKKIL; | [SEQ ID NO: 7] |
| KLALKLALKALKAALKLA; | [SEQ ID NO: 13] |
| KETWWETWWTEWSQPKKKRKV; | [SEQ ID NO: 14] |
| KAFAKLAARLYRKA; | [SEQ ID NO: 15] |
| KAFAKLAARLYRAA; | [SEQ ID NO: 16] |
| AAFAKLAAARLYRKA; | [SEQ ID NO: 17] |
| KAFAALAARLYRKA; | [SEQ ID NO: 18] |
| KAFAKLAARLYRKAGC; | [SEQ ID NO: 20] |
| KAFAKLAARLYRAAGC; | [SEQ ID NO: 21] |
| AAFAKLAARLYRKAGC; | [SEQ ID NO: 22] |
| KAFAALAARLYRKAGC; | [SEQ ID NO: 23] |
| KAFAKLAAQLYRKAGC; | [SEQ ID NO: 24] |
| AGGGGYGRKKRRQRRR; | [SEQ ID NO: 25] |
| YARAAARQARA; | [SEQ ID NO: 26] |
| YGRKKRRQRRR; | [SEQ ID NO: 27] |
| WLRRIKAWLRRIKA; | [SEQ ID NO: 28] |
| WLRRIKAWLRRIKAWLRRIKA; | [SEQ ID NO: 29] |
| FAKLAARLYRKA; | [SEQ ID NO: 30] |
| KAFAALAARLYRKA; | [SEQ ID NO: 18] |
| KAFAKLAARLYRAA; | [SEQ ID NO: 16] |
| KAFAKLAARLYRA; | [SEQ ID NO: 19] |
| FAKLAARLYRAA; and | [SEQ ID NO: 31] |
| FAKLAARLYRA. | [SEQ ID NO: 32] |

Further exemplary polypeptides according to the invention include, but are not limited to any of those listed above, wherein one or both of Z1 and Z2 are selected from the group consisting of:

| | |
|---|---|
| WLRRIKAWLRRIKA; | [SEQ ID NO: 28] |
| WLRRIKAWLRRIKAWLRRIKA; | [SEQ ID NO: 29] |
| YGRKKRRQRRR; | [SEQ ID NO: 27] |
| YARAAARQARA; | [SEQ ID NO: 26] |
| RQRRKKRG; | [SEQ ID NO: 3] |
| GRKKRRQR; | [SEQ ID NO: 4] |
| KAFAKLAARLYRKA; | [SEQ ID NO: 15] |
| FAKLAARLYRKA; | [SEQ ID NO: 30] |
| KAFAALAARLYRKA; | [SEQ ID NO: 18] |
| KAFAKLAARLYRAA; | [SEQ ID NO: 16] |
| KAFAKLAARLYRA; | [SEQ ID NO: 19] |
| FAKLAARLYRAA; and | [SEQ ID NO: 31] |
| FAKLAARLYRA. | [SEQ ID NO: 32] |

Further exemplary polypeptides according to the invention include, but are not limited to, those comprising or consisting of:

| | |
|---|---|
| YARAAARQARAKALARQLGVAA; | [SEQ ID NO: 33] |
| YGRKKRRQRRRKALARQLGVAA; | [SEQ ID NO: 34] |
| RQRRKKRGKALARQLGVAA; | [SEQ ID NO: 35] |
| GRKKRRQRKALARQLGVAA; | [SEQ ID NO: 36] |
| WLRRIKAWLRRIKAKALARQLGVAA; | [SEQ ID NO: 37] |
| WLRRIKAWLRIKAWLRRIKAKALARQLGVAA; | [SEQ ID NO: 38] |
| YARAAARQARAKKKALARQLGVAA; | [SEQ ID NO: 39] |

-continued

| | |
|---|---|
| YGRKKRRQRRRKKKALARQLGVAA; | [SEQ ID NO: 40] |
| RQRRKKRGKKKALARQLGVAA; | [SEQ ID NO: 41] |
| GRKKRRQRKKKALARQLGVAA; | [SEQ ID NO: 42] |
| WLRRIKAWLRRIKAKKKALARQLGVAA; | [SEQ ID NO: 43] |
| WLRRIKAWLRRIKAWLRRIKAKKKALARQLGVAA; | [SEQ ID NO: 44] |
| KAFAKLAARLYRKALARQLGVAA; | [SEQ ID NO: 45] |
| FAKLAARLYRKALARQLGVAA; | [SEQ ID NO: 46] |
| KAFAKLAARLYRAALARQLGVAA; | [SEQ ID NO: 47] |
| KAFAKLAARLYRALARQLGVAA; | [SEQ ID NO: 48] |
| KAFAALAARLYRAALARQLGVAA; | [SEQ ID NO: 49] |
| FAKLAARLYRAALARQLGVAA; | [SEQ ID NO: 50] |
| WLRRIKAWRRIKA-LNRQLGVAA; | |
| YARAAARQARAKALNRQLGVA; | [SEQ ID NO: 51] |
| KAFAKLAARLYRKALNRQLAVAA; | [SEQ ID NO: 52] |
| FAKLAARLYRKALNRQLAVAA; | [SEQ ID NO: 53] |
| KAFALKAARLYRKA-LNRQLGVAA; and | |
| FAKLAARLYRKA-LNRQLGVAA. | |

Further exemplary peptides include WLRRIKAWR-RIKALNRQLGVA [SEQ ID NO: 56], KAFALKAAR-LYRKALNRQLGVA [SEQ ID NO: 57], and FAKLAAR-LYRKALNRQLGVA [SEQ ID NO: 58].

Further exemplary peptides include YARAAAR-QARAKALNRQLGVAA [SEQ ID NO: 59].

Further exemplary polypeptides according to the invention include, but are not limited to, those comprising or consisting of: KALNRQLGVA [SEQ ID NO: 54], and KALNRQLGVA [SEQ ID NO: 55].

The polypeptides of the described invention may be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N_\alpha$-amino protected $N_\alpha$-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile $N_\alpha$-amino protected 9-fluorenyl-methoxycarbonyl (Fmoc) amino acids first described by Carpino and Han (1972, J. Org. Chem. 37:3403-3409). Both Fmoc and Boc Nα-amino protected amino acids can be obtained from Sigma, Cambridge Research Biochemical, or other chemical companies familiar to those skilled in the art. In addition, the polypeptides can be synthesized with other $N_\alpha$-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, C.alpha.-methyl amino acids, and $N_\alpha$-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-life in vivo.

According to another embodiment, the EPRO composition is a pharmaceutical composition.

According to another embodiment, the EPRO composition further comprises at least one additional active agent.

According to another embodiment, the additional active agent is an antifungal agent. According to another embodiment, the additional active agent is an antiviral agent. According to another embodiment, the additional active agent is an antiprotozoal agent. According to another embodiment, the additional active agent is an anesthetic agent. According to another embodiment, the additional active agent is a chemotherapeutic agent. According to another embodiment, the additional active agent is a vitamin. According to another embodiment, the additional active agent is a hormone. According to another embodiment, the additional active agent is a steroid.

The pharmaceutical compositions described herein contain a therapeutically effective amount of an EPRO composition and optionally at least one other therapeutic agent included in a pharmaceutically-acceptable carrier.

According to another embodiment, the EPRO composition may be formulated for parenteral administration by injection, for example, by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain suitable stabilizers or agents which increase the solubility of the compounds to allow for the preparation of highly concentrated solutions. Alternatively, the active compounds may be in powder form for constitution with a suitable vehicle, for example, sterile pyrogen-free water, before use.

The EPRO compositions also may comprise suitable solid or gel phase carriers or excipients. The (pharmaceutical) carrier must be of sufficiently high purity and of sufficiently low toxicity to render it suitable for administration to the mammal being treated. The (pharmaceutical) carrier further should maintain the stability and bioavailability of an active agent. The (pharmaceutical) carrier can be liquid or solid and is selected, with the planned manner of administration in mind, to provide for the desired bulk, consistency, etc., when combined with an active agent and other components of a given composition. The (pharmaceutical) carrier can be, without limitation, a binding agent (e.g., pregelatinised maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulphate, etc.). Other suitable (pharmaceutical) carriers for the compositions of the described invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Compositions of the described invention that are for cutaneous administration, such as topical (i.e., local), can include (pharmaceutical) carriers such as sterile and non-sterile aqueous solutions, non-aqueous solutions in common solvents such as alcohols, or solutions in liquid or solid oil bases. Such (pharmaceutical) carrier solutions also can contain buffers, diluents and other suitable additives. Compositions of the described invention that are for parenteral administration, such as intramuscular or subcutaneously, can include (pharmaceutical) carriers such as sterile aqueous solutions, non-aqueous solutions in common solvents such as alcohols, or solutions in a liquid oil base. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The EPRO composition, and optionally at least one other therapeutic, may be administered per se (neat) or in the form of a pharmaceutically acceptable salt, solvate or hydrate thereof. When used in medicine, the salts should be pharmaceutically acceptable, but non-pharmaceutically acceptable salts may conveniently be used to prepare pharmaceutically acceptable salts thereof.

Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids also may be made.

The formulations may be presented conveniently in unit dosage form and may be prepared by any of the methods well known in the art of pharmacy. All methods include the step of bringing into association an EPRO composition, or a pharmaceutically acceptable salt or solvate thereof ("active compound"), with the carrier, which constitutes one or more accessory agents. In general, the formulations are prepared by uniformly and intimately bringing into association the active agent with liquid carriers or finely divided solid carriers or both, and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers, such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations are also prepared by entrapping the drug in liposomes or microemulsions which are compatible with body tissues.

Injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions, may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 also may be used. The polymer is conjugated via an ester linkage to one or more hydroxyls of an inventive peptide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The therapeutic agent(s), including the EPRO composition, may be provided in particles. The particles may contain the therapeutic agent(s) in a core surrounded by a coating. The therapeutic agent(s) also may be dispersed throughout the particles. The therapeutic agent(s) also may be adsorbed on at least one surface of the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the EPRO composition in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the contents of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. This refers to controlled release, immediate as well as non-immediate release formulations, with non-immediate release formulations including, but not limited to, sustained release and delayed release formulations.

Use of a long-term sustained release implant may be particularly suitable for treatment of chronic conditions. Long-term sustained release implants are well-known to those of ordinary skill in the art and include some of the release systems described above.

2. Isolated Nucleic Acids

According to another aspect, the described invention provides an isolated nucleic acid that encodes a polypeptide having at least 85% amino acid sequence identity to a peptide having an amino acid sequence according to Formula I, wherein the polypeptide enhances outgrowth of at least one neurite process from a neuron cell body. In some embodiments, the isolated nucleic acid encodes a polypeptide with 90% amino acid sequence identity to a peptide having an amino acid sequence according to Formula I, wherein the polypeptide enhances outgrowth of at least one neurite process from a neuron cell body. In some embodiments, the isolated nucleic acid encodes a polypeptide with 95% amino acid sequence identity to a peptide having an amino acid sequence according to Formula I, wherein the polypeptide enhances outgrowth of at least one neurite process from a neuron cell body. In some embodiments, the isolated nucleic acid encodes a polypeptide with 100% amino acid sequence identity to a peptide having an amino acid sequence according to Formula I, wherein the polypeptide enhances outgrowth of at least one neurite process from a neuron cell body. In some embodiments, the isolated nucleic acid is operably linked to a controllable regulatory element.

According to another embodiment, the described invention provides an isolated nucleic acid that encodes a polypeptide having at least 85% amino acid sequence identity to a peptide having an amino acid sequence YARAAARQARAKALARQLGVAA [SEQ ID NO: 33], wherein the polypeptide enhances outgrowth of at least one neurite process from a neuron cell body.

According to another embodiment, the described invention provides an isolated nucleic acid that specifically hybridizes to mRNA encoding a peptide comprising an amino acid sequence according to Formula I. For example, a nucleic acid that may bind or hybridize to at least a portion of an mRNA of a cell encoding a peptide comprising an amino acid sequence according to Formula I may be considered a nucleic acid that specifically hybridizes.

According to another embodiment, the described invention provides an isolated nucleic acid that specifically hybridizes to mRNA encoding a peptide comprising an amino acid sequence according to Formula I, wherein the polypeptide enhances outgrowth of at least one neurite process from a neuron cell body. According to another embodiment, the described invention provides an isolated nucleic acid that encodes a polypeptide having at least 85% amino acid sequence identity to a peptide having an amino acid sequence YARAAARQARAKALARQLGVAA [SEQ ID NO: 33], wherein the polypeptide enhances outgrowth of at least one neurite process from a neuron cell body.

Methods of extraction of RNA are well-known in the art and are described, for example, in J. Sambrook et al., "Molecular Cloning: A Laboratory Manual" (Cold Spring Harbor Laboratory Press, Cold Spring Harbor, N.Y., 1989), vol. 1, ch. 7, "Extraction, Purification, and Analysis of Messenger RNA from Eukaryotic Cells," incorporated herein by this reference. Other isolation and extraction methods also are well-known, for example in F. Ausubel et al., "Current Protocols in Molecular Biology", John Wiley & Sons, 2007). Typically, isolation is performed in the presence of chaotropic agents, such as guanidinium chloride or guanidinium thiocyanate, although other detergents and extraction agents alternatively may be used. Typically, the mRNA is isolated from the total extracted RNA by chromatography over oligo(dT)-cellulose or other chromatographic media that have the capacity to bind the polyadenylated 3'-portion of mRNA molecules. Alternatively, but less preferably, total RNA can be used. However, it generally is preferred to isolate poly(A)+RNA from mammalian sources.

According to another embodiment, the described invention provides an antibody or an antibody fragment that specifically binds to an amino acid sequence of a peptide having an amino acid sequence according to Formula I, wherein the polypeptide enhances outgrowth of at least one neurite process from a neuron cell body. In some such embodiments, the antibody is used in purification of such peptides. In some such embodiments, the antibody is used in inhibition of such peptides. In some such embodiments, the antibody is used in diagnostic detection of such peptides.

According to another embodiment, the described invention provides an antibody or an antibody fragment that specifically binds to an amino acid sequence of a peptide of amino acid sequence YARAAARQARAKALARQLGVAA [SEQ ID NO: 33]. According to another embodiment, the described invention provides an antibody or an antibody fragment that specifically binds to an amino acid sequence of a peptide of amino acid sequence YARAAARQARAKALNRQLGVA [SEQ ID NO: 51]. According to another embodiment, the described invention provides an antibody or an antibody fragment that specifically binds to an amino acid sequence of a peptide of amino acid sequence FAKLAARLYRKALARQLGVAA [SEQ ID NO: 46].

According to another embodiment, the isolated nucleic acids encoding a peptide having an amino acid sequence according to Formula I, wherein the polypeptide enhances outgrowth of at least one neurite process from a neuron cell body, are incorporated into an expression vector. According to some such embodiments, the expression vector is for an eukaryotic cell. According to some such embodiments, the eukaryotic cell is a CHO cell. According to some such embodiments, the eukaryotic cell is a BHK cell. According to some such embodiments, the eukaryotic cell is an NIH 3T3 cell. According to some such embodiments, the eukaryotic cell is a Cos-7 cell. According to another embodiment, the isolated nucleic acid is an isolated nucleic acid encoding a polypeptide of amino acid sequence YARAAARQARAKALARQLGVAA [SEQ ID NO: 33]. According to another embodiment, the isolated nucleic acid is an isolated nucleic acid encoding a polypeptide of amino acid sequence YARAAARQARAKALNRQLGVA (SEQ ID NO: 51). According to another embodiment, the isolated nucleic acid is an isolated nucleic acid encoding a polypeptide of amino acid sequence FAKLAARLYRKALARQLGVAA [SEQ ID NO: 46].

3. Biomedical Devices

According to another aspect, the described invention provides a biomedical device comprising an EPRO composition comprising at least one polypeptide of an amino acid sequence according to Formula I:

Z1-X1-X2-X3-X4-X5-X6-X7-X8-X9-X10-Z2 wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; wherein the composition enhances outgrowth of at least one neurite process from a neuron cell body; is neuroprotective, or enhances neuroregeneration following neural injury, when disposed on or in the device.

According to another embodiment, in addition to the recited amino acids, X2, X3, X6 and X7 can be any aliphatic amino acid (whether naturally occurring or not), including, but not limited to, beta-alanine and 2-aminocyclohexane-1-carboxylic acid.

According to another embodiment, X4 is R; X5 is Q, and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G.

According to another embodiment, the at least one polypeptide of formula I is a peptide of amino sequence YARAAARQARAKALARQLGVAA [SEQ ID NO: 33]. According to another embodiment, the at least one polypeptide of formula I is a peptide of amino acid sequence YARAAARQARAKALNRQLGVA [SEQ ID NO: 51]. According to another embodiment, the at least one polypeptide of formula I is a peptide of amino acid sequence FAKLAARLYRKALARQLGVAA [SEQ ID NO: 46]. According to another embodiment, the at least one polypeptide of formula I is a peptide of amino acid sequence YARAAARQARAKALNRQLGVAA [SEQ ID NO: 59]. According to another embodiment, the at least one polypeptide of formula I is a peptide of amino acid sequence FAKLAARLYRKLALRQLGVAA [SEQ ID NO: 60].

According to another embodiment, at least one of Z1 and Z2 is a transduction domain. According to another embodiment, the transduction domain(s) is/are selected from the group consisting of: (R)$_{4-9}$ [SEQ ID NO: 1]; GRKKRRQR-RRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGRSAASRPTERPRAPARSASR-PRRPVE [SEQ ID NO: 6]; GWTLNSAGYLLGLINLKA-LAALAKKIL [SEQ ID NO: 7]; PLSSIFSRIGDP [SEQ ID NO: 8]; AAVALLPAVLLALLAP [SEQ ID NO: 9]; AAV-LLPVLLAAP [SEQ ID NO: 10]; VTVLALGALAGVGVG [SEQ ID NO: 11]; GALFLGWLGAAGSTMGAWSQP [SEQ ID NO: 12]; GWTLNSAGYLLGLINLKALAALAK-KIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAF-AKLAARLYRAA [SEQ ID NO: 16]; AAFAKLAAAR-LYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAK-LAARLYRKAGC [SEQ ID NO: 22]; KAFAALAAR-LYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRK-KRRQRRR [SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAF-AALAARLYRKA [SEQ ID NO: 18]; KAFAKLAAR-LYRAA [SEQ ID NO: 16]; KAFAKLAARLYRA [SEQ ID NO: 19]; FAKLAARLYRAA [SEQ ID NO: 31]; and FAK-LAARLYRA [SEQ ID NO: 32].

According to another embodiment, polypeptides according to the invention include, but are not limited to any of those listed above, wherein one or both of Z1 and Z2 are selected from the group consisting of: WLRRIKAWLR-RIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRKKRRQR [SEQ ID NO: 4]; KAFAKLAAR-LYRKA [SEQ ID NO: 15]; FAKLAARLYRKA [SEQ ID NO: 30]; KAFAALAARLYRKA [SEQ ID NO: 18]; KAF-AKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, the at least one polypeptide of formula I comprises YARAAARQARAKALAR-QLGVAA [SEQ ID NO: 33]; YGRKKRRQRRRKALAR-QLGVAA [SEQ ID NO: 34]; RQRRKKRGKALARQLGVAA [SEQ ID NO: 35]; GRK-KRRQRKALARQLGVAA [SEQ ID NO: 36]; WLR-RIKAWLRRIKAKALARQLGVAA [SEQ ID NO: 37]; WLRRIKAWLRRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALAR-QLGVAA [SEQ ID NO: 44]; KAFAKLAARLYRKALAR-QLGVAA [SEQ ID NO: 45]; FAKLAARLYRKALARQL-GVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKA-LNRQLGVAA; YARAAAR-QARAKALNRQLGVA [SEQ ID NO: 51]; KAFAKLAAR-LYRKALNRQLAVAA [SEQ ID NO: 52]; FAKLAAR-LYRKLNRQLAVAA [SEQ ID NO: 53]; KAFALKAARLYRKA-LNRQLGVAA; and FAKLAAR-LYRKA-LNRQLGVAA.

Further exemplary peptides include WLRRIKAWR-RIKALNRQLGVA [SEQ ID NO: 56], KAFALKAAR- LYRKALNRQLGVA [SEQ ID NO: 57], and FAKLAAR-
LYRKALNRQLGVA [SEQ ID NO: 58].

Further exemplary polypeptides according to the invention include, but are not limited to, those comprising or consisting of: KALNRQLGVA [SEQ ID NO: 54], and KALNRQLGVA [SEQ ID NO: 55].

According to another embodiment, the EPRO composition is a pharmaceutical composition.

According to another embodiment, the EPRO composition further comprises at least one additional active agent.

According to another embodiment, at least one axon regenerates through an EPRO composition treated tissue more effectively than through untreated tissues. According to some such embodiments, the at least one axon regenerated extend at least twice as far through the EPRO composition treated tissue as do axons regenerating through untreated tissues.

According to another embodiment, at least one axon treated with the EPRO composition regenerates more effectively than an untreated axon. According to some such embodiments, the at least one axon treated with the EPRO composition extends at least twice as far as an untreated axon.

According to another embodiment, at least one dendrite regenerates through EPRO composition treated tissue more effectively than through untreated tissues. According to some such embodiments, the at least one dendrite regenerated extends at least twice as far through EPRO composition treated tissue than at least one dendrite regenerating through untreated tissues.

According to another embodiment, the at least one dendrite treated with the EPRO composition regenerates more effectively than at least one untreated dendrite. According to some such embodiments, the at least one dendrite treated with EPRO composition extends at least twice as far as at least one untreated dendrite.

According to another embodiment, the biomedical device is a stent. According to another embodiment, the biomedical device is a graft. According to another embodiment, the biomedical device is a shunt. According to another embodiment, the biomedical device is a stent graft. According to another embodiment, the biomedical device is a fistula. According to another embodiment, the biomedical device is an angioplasty device. According to another embodiment, the biomedical device is a balloon catheter. According to another embodiment, the biomedical device is a venous catheter. According to another embodiment, the biomedical device is an implantable drug delivery device. According to another embodiment, the biomedical device is an adhesion barrier. According to another embodiment, the biomedical device is a wound dressing. According to another embodiment, the biomedical device is a hydrocolloid. According to another embodiment, the biomedical device is a hydrogel. According to another embodiment, the biomedical device is a foam. According to another embodiment, the biomedical device is a hydrophilic foam. According to another embodiment, the biomedical device is a hydrophobic foam. According to another embodiment, the biomedical device is a calcium alginate. According to another embodiment, the biomedical device is a cellophane. According to another embodiment, the biomedical device is a pluronic. According to another embodiment, the biomedical device is a biological polymer. According to another embodiment, the biomedical device is a microelectrode. According to another embodiment, the biomedical device is a probe. According to another embodiment, the biomedical device is a suture. According to another embodiment, the biomedical device is a tissue scaffold.

In some embodiments, the EPRO composition comprising at least one polypeptide having an amino acid sequence according to Formula I, wherein the polypeptide enhances nerve regeneration, is directly disposed onto or into a biomedical device. According to some such embodiments, the EPRO composition comprising at least one polypeptide is directly disposed onto the outer surface of the biomedical device. According to some such embodiments, the EPRO composition comprising at least one polypeptide is directly disposed onto the inner surface of the biomedical device. According to some such embodiments, the EPRO composition comprising at least one polypeptide is directly disposed into the biomedical device such that the at least one polypeptide is embedded into the outer surface of the biomedical device. According to some such embodiments, EPRO composition comprising the at least one polypeptide is directly disposed into the biomedical device such that the at least one polypeptide is embedded into the inner surface of the biomedical device.

Direct disposition of the EPRO composition comprising at least one polypeptide having an amino acid sequence according to Formula I, wherein the polypeptide enhances outgrowth of at least one neurite process from a neuron cell body, includes, but is not limited to, a biomedical device in a solution containing the EPRO composition comprising at least one polypeptide, spin coating or spraying a solution containing the EPRO composition comprising at least one polypeptide onto the device, implanting any device that would deliver the at least one polypeptide, and administering the EPRO composition comprising at least one polypeptide through a catheter directly onto a surface or into any organ.

In some embodiments, the EPRO composition comprising at least one polypeptide having an amino acid sequence according to Formula I, wherein the polypeptide enhances outgrowth of at least one neurite process from a neuron cell body, is indirectly dispersed onto or into the biomedical device. Indirect disposition results in the EPRO composition comprising at least one polypeptide being not directly in contact with the biomedical device.

According to another embodiment, the EPRO composition comprising at least one polypeptide is disposed in a matrix. According to some such embodiments, the matrix is a gel matrix or a viscous fluid. According to another embodiment, the gel matrix is disposed onto the biomedical device. According some such embodiments, the gel matrix is a heparin coating. As used herein "heparin coating" includes heparin adsorbed to a surface, heparin bonded to a surface, and heparin embedded in a PTFE polymer surface. Heparin coatings may be in a gel form, such as a hydrogel, or a non-gel form. According to some embodiments, the matrix is a thin-film, silica sol-gel coating.

Such matrices may be prepared to modify the binding and release properties of the at least one polypeptide as required. According to another embodiment, the at least one polypeptide is layered between heparin coatings onto a biomedical device. In a non-limiting example, the release of the at least one polypeptide from interstitial surfaces of a biomedical device, such as, for example, a poly(tetrafluoroethylene) (PTFE) vascular device or sheet, may be controlled by first adsorbing or bonding heparin to the surface and/or interstices of the device followed by adsorption of the at least one polypeptide. Alternating layers of heparin and the at least one polypeptide may be used to increase the at least one polypeptide dose and/or time of release. Under physiological conditions within the body, the kinetics of the association and dissociation of the polypeptides disclosed herein to and from heparin will lead to a delayed release profile relative to release of the polypeptide from a bare device. In addition, the release profile may be further altered through changes in local temperature, pH or ionic strength.

According to another embodiment, the at least one polypeptide is a peptide having an amino acid sequence YARAAARQARAKALARQLGVAA [SEQ ID NO: 33]. According to another embodiment, the at least one polypeptide is a peptide having an amino acid sequence YARAAARQARAKALNRQLGVA [SEQ ID NO: 51]. According to another embodiment, the at least one polypeptide is a peptide having an amino acid sequence FAKLAARLYRKALARQLGVAA [SEQ ID NO: 46]. According to some embodiments, the at least one polypeptide has at least about 70% sequence identity to a polypeptide having an amino acid sequence according to Formula I. According to some embodiments, the at least one polypeptide has at least about 75% sequence identity to a polypeptide having an amino acid sequence according to Formula I. According to some embodiments, the at least one polypeptide has at least about 80% sequence identity to a polypeptide having an amino acid sequence according to Formula I. According to some embodiments, the at least one polypeptide has at least about 85% sequence identity to a polypeptide having an amino acid sequence according to Formula I.

According to another embodiment, the at least one polypeptide is a peptide having an amino acid sequence YARAAARQARAKALNRQLGVAA [SEQ ID NO: 59]. According to another embodiment, the at least one polypeptide is a peptide having an amino acid sequence FAKLAARLYRKLALRQLGVAA [SEQ ID NO: 60].

According to some embodiments, the at least one polypeptide has at least about 70% sequence identity to amino acid sequence YARAAARQARAKALARQLGVAA [SEQ ID NO: 33]. According to some embodiments, the at least one polypeptide has at least about 75% sequence identity to amino acid sequence YARAAARQARAKALARQLGVAA [SEQ ID NO: 33]. According to some embodiments, the at least one polypeptide has at least about 80% sequence identity to amino acid sequence YARAAARQARAKALARQLGVAA [SEQ ID NO: 33]. According to some embodiments, the at least one polypeptide has at least about 85% sequence identity to amino acid sequence YARAAARQARAKALARQLGVAA [SEQ ID NO: 33].

According to some embodiments, the at least one polypeptide has at least about 70% sequence identity to amino acid sequence YARAAARQARAKALNRQLGVA [SEQ ID NO: 51]. According to some embodiments, the at least one polypeptide has at least about 75% sequence identity to amino acid sequence YARAAARQARAKALNRQLGVA [SEQ ID NO: 51]. According to some embodiments, the at least one polypeptide has at least about 80% sequence identity to amino acid sequence YARAAARQARAKALNRQLGVA [SEQ ID NO: 51]. According to some embodiments, the at least one polypeptide has at least about 85% sequence identity to amino acid sequence YARAAARQARAKALNRQLGVA [SEQ ID NO: 51].

According to some embodiments, the at least one polypeptide has at least about 70% sequence identity to amino acid sequence YARAAARQARAKALNRQLGVAA [SEQ ID NO: 59]. According to some embodiments, the at least one polypeptide has at least about 75% sequence identity to amino acid sequence YARAAARQARAKALNRQLGVAA [SEQ ID NO: 59]. According to some embodiments, the at least one polypeptide has at least about 80% sequence identity to amino acid sequence YARAAARQARAKALNRQLGVAA [SEQ ID NO: 59]. According to some embodiments, the at least one polypeptide has at least about 85% sequence identity to amino acid sequence YARAAARQARAKALNRQLGVAA [SEQ ID NO: 59].

According to some embodiments, the at least one polypeptide has at least about 70% sequence identity to amino acid sequence FAKLAARLYRKALARQLGVAA [SEQ ID NO: 46]. According to some embodiments, the at least one polypeptide has at least about 75% sequence identity to amino acid sequence FAKLAARLYRKALARQLGVAA [SEQ ID NO: 46]. According to some embodiments, the at least one polypeptide has at least about 80% sequence identity to amino acid sequence FAKLAARLYRKALARQLGVAA [SEQ ID NO: 46]. According to some embodiments, the at least one polypeptide has at least about 85% sequence identity to amino acid sequence FAKLAARLYRKALARQLGVAA [SEQ ID NO: 46].

According to some embodiments, the at least one polypeptide has at least about 70% sequence identity to amino acid sequence FAKLAARLYRKLALRQLGVAA [SEQ ID NO: 60]. According to some embodiments, the at least one polypeptide has at least about 75% sequence identity to amino acid sequence FAKLAARLYRKLALRQLGVAA [SEQ ID NO: 60]. According to some embodiments, the at least one polypeptide has at least about 80% sequence identity to amino acid sequence FAKLAARLYRKLALRQLGVAA [SEQ ID NO: 60]. According to some embodiments, the at least one polypeptide has at least about 85% sequence identity to amino acid sequence FAKLAARLYRKLALRQLGVAA [SEQ ID NO: 60].

As will be understood by those of skill in the art, any sulfated polysaccharide or negatively charged polymer can be used in like manner to heparin to provide desired release characteristics.

4. Methods for Improving or Enhancing Neurite Outgrowth

According to another aspect, the described invention provides a method for improving or enhancing neurite outgrowth, the method comprising: (a) providing a therapeutically effective amount of an EPRO composition, the EPRO composition comprising: (i) at least one polypeptide having an amino acid sequence according to Formula I:

Z1-X1-X2-X3-X4-X5-X6-X7-X8-X9-X10-Z2 wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; wherein the polypeptide enhances or improves outgrowth of at least one neurite process from a neuron cell body; and (ii) a carrier; (b) administering the EPRO composition to a subject in need thereof; and (c) increasing neurite outgrowth relative to neurite outgrowth of a neuron that has not been treated with the EPRO composition.

According to another embodiment, in addition to the recited amino acids, X2, X3, X6 and X7 can be any aliphatic amino acid (whether naturally occurring or not), including, but not limited to, beta-alanine and 2-aminocyclohexane-1-carboxylic acid.

According to another embodiment, X4 is R; X5 is Q, and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G.

According to another embodiment, at least one of Z1 and Z2 is a transduction domain. According to another embodiment, the transduction domain(s) is/are selected from the group consisting of: (R)$_{4-9}$ [SEQ ID NO: 1]; GRKKRRQRRRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATGRSAASRPTERPRAPARSASRPRRPVE [SEQ ID NO: 6]; GWTLNSAGYLLGLINLKALAALAKKIL [SEQ ID NO: 7]; PLSSIFSRIGDP [SEQ ID NO: 8]; AAVALLPAVLLALLAP [SEQ ID NO: 9]; AAVLLPVLLAAP [SEQ ID NO: 10]; VTVLALGALAGVGVG [SEQ ID NO: 11]; GALFLGWLGAAGSTMGAWSQP [SEQ ID NO: 12]; GWTLNSAGYLLGLINLKALAALAKKIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAFAKLAARLYRAA [SEQ ID NO: 16]; AAFAKLAARLYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAKLAARLYRKAGC [SEQ ID NO: 22]; KAFAALAARLYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRKKRRQRRR [SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, the at least one polypeptide of Formula I includes, but are not limited to any of those listed above, wherein one or both of Z1 and Z2 are selected from the group consisting of: WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRKKRRQR [SEQ ID NO: 4]; KAFAKLAARLYRKA [SEQ ID NO: 15]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, the at least one polypeptide of Formula I comprises YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKA-LNRQLGVAA; YARAAARQARAKALNRQLGVA [SEQ ID NO: 51]; KAFAKLAARLYRKALNRQLAVAA [SEQ ID NO: 52]; FAKLAARLYRKALNRQLAVAA [SEQ ID NO: 53]; KAFALKAARLYRKA-LNRQLGVAA; and FAKLAARLYRKA-LNRQLGVAA.

Further exemplary peptides include WLRRIKAWRRIKALNRQLGVA [SEQ ID NO: 56], KAFALKAARLYRKALNRQLGVA [SEQ ID NO: 57], and FAKLAARLYRKALNRQLGVA [SEQ ID NO: 58].

Further exemplary polypeptides according to the invention include, but are not limited to, those comprising or consisting of: KALNRQLGVA [SEQ ID NO: 54], and KALNRQLGVA [SEQ ID NO: 55].

According to one embodiment, the at least one polypeptide has an amino acid sequence of at least 70% sequence identity to an amino acid sequence according to Formula I, wherein the polypeptide having an amino acid sequence according to Formula I enhances outgrowth of at least one neurite process from a neuron cell body. According to one embodiment, the at least one polypeptide has an amino acid sequence of at least 75% sequence identity to an amino acid sequence according to Formula I, wherein the polypeptide having an amino acid sequence according to Formula I enhances outgrowth of at least one neurite process from a neuron cell body. According to one embodiment, the at least one polypeptide has an amino acid sequence of at least 80% sequence identity to an amino acid sequence according to Formula I, wherein the polypeptide having an amino acid sequence according to Formula I enhances outgrowth of at least one neurite process from a neuron cell body. According to one embodiment, the at least one polypeptide has an amino acid sequence of at least 85% sequence identity to an amino acid sequence according to Formula I, wherein the polypeptide having an amino acid sequence according to Formula I enhances outgrowth of at least one neurite process from a neuron cell body. According to some embodiments, the at least one polypeptide has at least about 70% sequence identity to amino acid sequence YARAAARQARAKALARQLGVAA [SEQ ID NO: 33]. According to some embodiments, the at least one polypeptide has at least about 75% sequence identity to amino acid sequence YARAAARQARAKALARQLGVAA [SEQ ID NO: 33]. According to some embodiments, the at least one polypeptide has at least about 80% sequence identity to amino acid sequence YARAAARQARAKALARQLGVAA [SEQ ID NO: 33]. According to some embodiments, the at least one polypeptide has at least about 85% sequence identity to amino acid sequence YARAAARQARAKALARQLGVAA [SEQ ID NO: 33].

According to some embodiments, the at least one polypeptide has at least about 70% sequence identity to amino acid sequence YARAAARQARAKALNRQLGVA [SEQ ID NO: 51]. According to some embodiments, the at least one polypeptide has at least about 75% sequence identity to amino acid sequence YARAAARQARAKALNRQLGVA [SEQ ID NO: 51]. According to some embodiments, the at least one polypeptide has at least about 80% sequence identity to amino acid sequence YARAAARQARAKALNRQLGVA [SEQ ID NO: 51]. According to some embodiments, the at least one polypeptide has at least about 85% sequence identity to amino acid sequence YARAAARQARAKALNRQLGVA [SEQ ID NO: 51].

According to some embodiments, the at least one polypeptide has at least about 70% sequence identity to amino acid sequence YARAAARQARAKALNRQLGVAA [SEQ ID NO: 59]. According to some embodiments, the at least one polypeptide has at least about 75% sequence identity to amino acid sequence YARAAARQARAKALNRQLGVAA [SEQ ID NO: 59]. According to some embodiments, the at least one polypeptide has at least about 80% sequence identity to amino acid sequence YARAAARQARAKALNRQLGVAA [SEQ ID NO: 59]. According to some embodiments, the at least one polypeptide has at least about 85% sequence identity to amino acid sequence YARAAARQARAKALNRQLGVAA [SEQ ID NO: 59].

According to some embodiments, the at least one polypeptide has at least about 70% sequence identity to amino acid sequence FAKLAARLYRKALARQLGVAA [SEQ ID NO: 46]. According to some embodiments, the at least one polypeptide has at least about 75% sequence identity to amino acid sequence FAKLAARLYRKALARQLGVAA [SEQ ID NO: 46]. According to some embodiments, the at least one polypeptide has at least about 80% sequence identity to amino acid sequence FAKLAARLYRKALARQLGVAA [SEQ ID NO: 46]. According to some embodiments, the at least one polypeptide has at least about 85% sequence identity to amino acid sequence FAKLAARLYRKALARQLGVAA [SEQ ID NO: 46].

According to some embodiments, the at least one polypeptide has at least about 70% sequence identity to amino acid sequence FAKLAARLYRKLALRQLGVAA [SEQ ID NO: 60]. According to some embodiments, the at least one polypeptide has at least about 75% sequence identity to amino acid sequence FAKLAARLYRKLALRQLGVAA [SEQ ID NO: 60]. According to some embodiments, the at least one polypeptide has at least about 80% sequence identity to amino acid sequence FAKLAARLYRKLALRQLGVAA [SEQ ID NO: 60]. According to some embodiments, the at least one polypeptide has at least about 85% sequence identity to amino acid sequence FAKLAARLYRKLALRQLGVAA [SEQ ID NO: 60].

According to another embodiment, the neurite process is an axon. According to some embodiments, the extension of the neurite process is increased at least 10% in length relative to the extension of the neurite process of a neuron that has not been treated with the EPRO composition. According to some embodiments, the extension of the neurite process is increased at least 20% in length relative to the extension of the neurite process of a neuron that has not been treated with the EPRO composition. According to some embodiments, the extension of the neurite process is increased at least 30% in length relative to the extension of the neurite process of a neuron that has not been treated with the EPRO composition. According to some embodiments, the extension of the neurite process is increased at least 40% in length relative to the extension of the neurite process of a neuron that has not been treated with the EPRO composition. According to some embodiments, the extension of the neurite process is increased at least 50% in length relative to the extension of the neurite process of a neuron that has not been treated with the EPRO composition. According to some embodiments, the extension of the neurite process is increased at least 60% in length relative to the extension of the neurite process of a neuron that has not been treated with the EPRO composition. According to some embodiments, the extension of the neurite process is increased at least 70% in length relative to the extension of the neurite process of a neuron that has not been treated with the EPRO composition. According to some embodiments, the extension of the neurite process is increased at least 80% in length relative to the extension of the neurite process of a neuron that has not been treated with the EPRO composition. According to some embodiments, the extension of the neurite process is increased at least 90% in length relative to the outgrowth of the neurite process of a neuron that has not been treated with the EPRO composition.

According to another embodiment, the EPRO composition enhances neurite outgrowth by inhibiting expression of at least one inflammatory cytokine from activated microglia. According to another embodiment, the at least one inflammatory cytokine is at least one of IL-1 beta, IL-6, and TNF-alpha.

According to another embodiment, at least one axon regenerates through a EPRO composition treated tissue more effectively than through at least one untreated tissue. According to some such embodiments, the at least one axon regenerated extends at least twice as far through a EPRO composition treated tissue as do those axons regenerating through untreated tissues.

According to another embodiment, the at least one polypeptide of formula I regenerates at least one axon treated with the at least one polypeptide of formula I more effectively than an untreated axon. According to some such embodiments, the at least one axon treated with the at least one polypeptide of formula I extends at least twice as far as an untreated axon.

According to another embodiment, the neurite process is at least one dendrite. According to some such embodiments, the outgrowth of the neurite process is increased at least 10% in length relative to at least one dendrite of the neurite process that has not been treated with the EPRO composition. According to some such embodiments, the outgrowth of the neurite process is increased at least 20% in length relative to at least one dendrite of the neurite process that has not been treated with the EPRO composition. According to some such embodiments, the outgrowth of the neurite process is increased at least 30% in length relative to at least one dendrite of the neurite process that has not been treated with the EPRO composition. According to some such embodiments, the outgrowth of the neurite process is increased at least 40 in length relative to at least one dendrite of the neurite process that has not been treated with the EPRO composition. According to some such embodiments, the outgrowth of the neurite process is increased at least 50% in length relative to at least one dendrite of the neurite process that has not been treated with the EPRO composition. According to some such embodiments, the outgrowth of the neurite process is increased at least 60% in length relative to at least one dendrite of the neurite process that has not been treated with the EPRO composition. According to some such embodiments, the outgrowth of the neurite process is increased at least 70% in length relative to at least one dendrite of the neurite process that has not been treated with the EPRO composition. According to some such embodiments, the outgrowth of the neurite process is increased at least 80% in length relative to at least one dendrite of the neurite process that has not been treated with the EPRO composition. According to some such embodiments, the outgrowth of the neurite process is increased at least 90% in length relative to at least one dendrite of the neurite process that has not been treated with the EPRO composition.

According to another embodiment, at least one dendrite regenerates through an EPRO composition treated tissue more effectively than through untreated tissues. According to some such embodiments, the at least one dendrite regenerated extends at least twice as far through an EPRO composition treated tissue as at least one dendrite regenerating through untreated tissues.

According to another embodiment, the at least one polypeptide of formula I regenerates at least one dendrite treated with the at least one polypeptide of formula I more effectively than at least one untreated dendrite. According to some such embodiments, the at least one dendrite treated with the at least one polypeptide of formula I extends at least twice as far as at least one untreated dendrite.

According to another embodiment, the EPRO composition is a pharmaceutical composition.

According to another embodiment, the composition further comprises at least one additional active agent.

5. Methods for Improving or Enhancing Nerve Regeneration

According to another aspect, the described invention provides a method for improving or enhancing nerve regeneration, the method comprising: (a) providing a therapeutically effective amount of an EPRO composition, the composition comprising: (i) at least one polypeptide having an amino acid sequence according to Formula I:

Z1-X1-X2-X3-X4-X5-X6-X7-X8-X9-X10-Z2 wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent; and (ii) a carrier; (b) administering the composition to a subject in need thereof; and (c) increasing neurite regrowth relative to the regrowth of a neurite process of a neuron that has not been treated with the EPRO composition.

According to another embodiment, the method further comprises step (d) effecting nerve regeneration by increasing the number of neurite projections.

According to another embodiment, in addition to the recited amino acids, X2, X3, X6 and X7 can be any aliphatic amino acid (whether naturally occurring or not), including, but not limited to, beta-alanine and 2-aminocyclohexane-1-carboxylic acid.

According to another embodiment, X4 is R; X5 is Q, and/or X8 is V. According to another embodiment, X3 is selected from the group consisting of V, L, I, A, G, Q and N. According to another embodiment, X6 is selected from the group consisting of C, A, G, L, V, I, M, Y, W and F.

According to another embodiment, X7 is selected from the group consisting of S, A, C, T and G.

According to another embodiment, at least one of Z1 and Z2 is a transduction domain. According to another embodiment, the transduction domain(s) is/are selected from the group consisting of: $(R)_{4-9}$ [SEQ ID NO: 1]; GRKKRRQRRRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGRSAASRPTERPRAPARSASRPRRPVE [SEQ ID NO: 6]; GWTLNSAGYLLGLINLKAAALAKKIL [SEQ ID NO: 7]; PLSSIFSRIGDP [SEQ ID NO: 8]; AAVALLPAVLLALLAP [SEQ ID NO: 9]; AAVLLPVLLAAP [SEQ ID NO: 10]; VTVLALGALAGVGVG [SEQ ID NO: 11]; GALFLGWLGAAGSTMGAWSQP [SEQ ID NO: 12]; GWTLNSAGYLLGLINLKALAALAKKIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAFAKLAARLYRAA [SEQ ID NO: 16]; AAFAKLAAARLYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAKLAARLYRKAGC [SEQ ID NO: 22]; KAFAALAARLYRKAGC [SEQ ID NO: 23]; KAFAKLAAQLYRKAGC [SEQ ID NO: 24]; AGGGGYGRKKRRQRRR [SEQ ID NO: 25]; YARAAARQARA [SEQ ID NO: 26]; YGRKKRRQRRR [SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, exemplary polypeptides according to the invention include, but are not limited to any of those listed above, wherein one or both of Z1 and Z2 are selected from the group consisting of: WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAARQARA [SEQ ID NO: 26]; RQRRKKRG [SEQ ID NO: 3]; GRKKRRQR [SEQ ID NO: 4]; KAFAKLAARLYRKA [SEQ ID NO: 15]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, the at least one polypeptide of formula I comprises YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50];

WLRRIKAWRRIKA-LNRQLGVAA; YARAAAR-QARAKALNRQLGVA [SEQ ID NO: 51]; KAFAKLAAR-LYRKALNRQLAVAA [SEQ ID NO: 52]; FAKLAAR-LYRKALNRQLAVAA [SEQ ID NO: 53]; KAFALKAARLYRKA-LNRQLGVAA; and FAKLAAR-LYRKA-LNRQLGVAA.

Further exemplary peptides include WLRRIKAWR-RIKALNRQLGVA [SEQ ID NO: 56], KAFALKAAR-LYRKALNRQLGVA [SEQ ID NO: 57], and FAKLAAR-LYRKALNRQLGVA [SEQ ID NO: 58].

Further exemplary polypeptides according to the invention include, but are not limited to, those comprising or consisting of: KALNRQLGVA [SEQ ID NO: 54], and KALNRQLGVA [SEQ ID NO: 55].

According to another embodiment, the at least one polypeptide of formula I of the EPRO composition is a peptide of amino sequence YARAAARQARAKALARQLGVAA (SEQ ID NO: 33). According to another embodiment, the at least one polypeptide of formula I of the EPRO composition is a peptide of amino acid sequence YARAAAR-QARAKALNRQLGVA [SEQ ID NO: 51]. According to another embodiment, the at least one polypeptide of formula I of the EPRO composition is a peptide of amino acid sequence FAKLAARLYRKALARQLGVAA [SEQ ID NO: 46].

According to another embodiment, the at least one polypeptide of formula I of the EPRO composition is a peptide of amino acid sequence YARAAARQARAKALNRQL-GVAA [SEQ ID NO: 59]. According to another embodiment, the at least one polypeptide of formula I of the EPRO composition is a peptide of amino acid sequence FAK-LAARLYRKLALRQLGVAA [SEQ ID NO: 60].

According to one embodiment, the at least one polypeptide has an amino acid sequence of at least 70% sequence identity to an amino acid sequence according to Formula I, wherein the polypeptide having an amino acid sequence according to Formula I enhances regrowth of at least one neurite process from a neuron cell body. According to one embodiment, the at least one polypeptide has an amino acid sequence of at least 75% sequence identity to an amino acid sequence according to Formula I, wherein the polypeptide having an amino acid sequence according to Formula I enhances regrowth of at least one neurite process from a neuron cell body. According to one embodiment, the at least one polypeptide has an amino acid sequence of at least 80% sequence identity to an amino acid sequence according to Formula I, wherein the polypeptide having an amino acid sequence according to Formula I enhances regrowth of at least one neurite process from a neuron cell body. According to one embodiment, the at least one polypeptide has an amino acid sequence of at least 85% sequence identity to an amino acid sequence according to Formula I, wherein the polypeptide having an amino acid sequence according to Formula I enhances regrowth of at least one neurite process from a neuron cell body.

According to some embodiments, the at least one polypeptide has at least about 70% sequence identity to amino acid sequence YARAAARQARAKALARQLGVAA [SEQ ID NO: 33]. According to some embodiments, the at least one polypeptide has at least about 75% sequence identity to amino acid sequence YARAAARQARAKALARQLGVAA [SEQ ID NO: 33]. According to some embodiments, the at least one polypeptide has at least about 80% sequence identity to amino acid sequence YARAAARQARAKA-LARQLGVAA [SEQ ID NO: 33]. According to some embodiments, the at least one polypeptide has at least about 85% sequence identity to amino acid sequence YARAAAR-QARAKALARQLGVAA [SEQ ID NO: 33].

According to some embodiments, the at least one polypeptide has at least about 70% sequence identity to amino acid sequence YARAAARQARAKALNRQLGVA [SEQ ID NO: 51]. According to some embodiments, the at least one polypeptide has at least about 75% sequence identity to amino acid sequence YARAAARQARAKALNRQLGVA [SEQ ID NO: 51]. According to some embodiments, the at least one polypeptide has at least about 80% sequence identity to amino acid sequence YARAAARQARAKALN-RQLGVA [SEQ ID NO: 51]. According to some embodiments, the at least one polypeptide has at least about 85% sequence identity to amino acid sequence YARAAAR-QARAKALNRQLGVA [SEQ ID NO: 51].

According to some embodiments, the at least one polypeptide has at least about 70% sequence identity to amino acid sequence YARAAARQARAKALNRQLGVAA [SEQ ID NO: 59]. According to some embodiments, the at least one polypeptide has at least about 75% sequence identity to amino acid sequence YARAAARQARAKALNRQLGVAA [SEQ ID NO: 59]. According to some embodiments, the at least one polypeptide has at least about 80% sequence identity to amino acid sequence YARAAARQARAKALN-RQLGVAA [SEQ ID NO: 59]. According to some embodiments, the at least one polypeptide has at least about 85% sequence identity to amino acid sequence YARAAAR-QARAKALNRQLGVAA [SEQ ID NO: 59].

According to some embodiments, the at least one polypeptide has at least about 70% sequence identity to amino acid sequence FAKLAARLYRKALARQLGVAA [SEQ ID NO: 46]. According to some embodiments, the at least one polypeptide has at least about 75% sequence identity to amino acid sequence FAKLAARLYRKALARQLGVAA [SEQ ID NO: 46]. According to some embodiments, the at least one polypeptide has at least about 80% sequence identity to amino acid sequence FAKLAARLYRKALAR-QLGVAA [SEQ ID NO: 46]. According to some embodiments, the at least one polypeptide has at least about 85% sequence identity to amino acid sequence FAKLAAR-LYRKALARQLGVAA [SEQ ID NO: 46].

According to some embodiments, the at least one polypeptide has at least about 70% sequence identity to amino acid sequence FAKLAARLYRKLALRQLGVAA [SEQ ID NO: 60]. According to some embodiments, the at least one polypeptide has at least about 75% sequence identity to amino acid sequence FAKLAARLYRKLALRQLGVAA [SEQ ID NO: 60]. According to some embodiments, the at least one polypeptide has at least about 80% sequence identity to amino acid sequence FAKLAARLYRKLAL-RQLGVAA [SEQ ID NO: 60]. According to some embodiments, the at least one polypeptide has at least about 85% sequence identity to amino acid sequence FAKLAAR-LYRKLALRQLGVAA [SEQ ID NO: 60].

According to another embodiment, the neurite process is an axon. According to some embodiments, the regrowth of the neurite process is increased at least 10% in length relative to the regrowth of a neurite process of a neuron that has not been treated with the EPRO composition. According to some embodiments, the regrowth of the neurite process is increased at least 20% in length relative to the regrowth of a neurite process of a neuron that has not been treated with the EPRO composition. According to some embodiments, the regrowth of the neurite process is increased at least 30% in length relative to the regrowth of a neurite process of a neuron that has not been treated with the EPRO composition. According to some embodiments, the regrowth of the neurite process is increased at least 40% in length relative to the regrowth of a neurite process of a neuron that has not been treated with the EPRO composition. According to some embodiments, the regrowth of the neurite process is increased at least 50% in length relative to the regrowth of a neurite process of a neuron that has not been treated with the EPRO composition. According to some embodiments, the regrowth of the neurite process is increased at least 60% in length relative to the regrowth of a neurite process of a neuron that has not been treated with the EPRO composition. According to some embodiments, the regrowth of the neurite process is increased at least 70% in length relative to the regrowth of a neurite process of a neuron that has not been treated with the EPRO composition. According to some embodiments, the regrowth of the neurite process is increased at least 80% in length relative to the regrowth of a neurite process of a neuron that has not been treated with the EPRO composition. According to some embodiments, the regrowth of the neurite process is increased at least 90% in length relative to the regrowth of a neurite process of a neuron that has not been treated with the EPRO composition.

According to another embodiment, the EPRO composition increases neurite regrowth by inhibiting expression of at least one inflammatory cytokine from activated microglia. According to another embodiment, the at least one inflammatory cytokine is at least one of IL-1 beta, IL-6, and TNF-alpha.

According to another embodiment, axons regenerate through EPRO composition treated tissue more effectively than through untreated tissues. According to some such embodiments, the axons regenerated extend at least twice as far through EPRO composition treated tissue than those axons regenerating through untreated tissues.

According to another embodiment, the at least one polypeptide of formula I regenerates at least one axon treated with the at least one polypeptide of formula I more effectively than an untreated axon. According to some such embodiments, the at least one axon treated with the at least one polypeptide of formula I extends at least twice as far as an untreated axon.

According to another embodiment, the neurite process is at least one dendrite. According to some such embodiments, the regrowth of the neurite process is increased at least 10% in length relative to at least one dendrite of the neurite process that has not been treated with the EPRO composition. According to some such embodiments, the regrowth of the neurite process is increased at least 20% in length relative to at least one dendrite of the neurite process that has not been treated with the EPRO composition. According to some such embodiments, the regrowth of the neurite process is increased at least 30% in length relative to at least one dendrite of the neurite process that has not been treated with the EPRO composition. According to some such embodiments, the regrowth of the neurite process is increased at least 40 in length relative to at least one dendrite of the neurite process that has not been treated with the EPRO composition. According to some such embodiments, the regrowth of the neurite process is increased at least 50% in length relative to at least one dendrite of the neurite process that has not been treated with the EPRO composition. According to some such embodiments, the regrowth of the neurite process is increased at least 60% in length relative to at least one dendrite of the neurite process that has not been treated with the EPRO composition. According to some such embodiments, the regrowth of the neurite process is increased at least 70% in length relative to at least one dendrite of the neurite process that has not been treated with the EPRO composition. According to some such embodiments, the regrowth of the neurite process is increased at least 80% in length relative to at least one dendrite of the neurite process that has not been treated with the EPRO composition. According to some such embodiments, the regrowth of the neurite process is increased at least 90% in length relative to at least one dendrite of the neurite process that has not been treated with the EPRO composition.

According to another embodiment, at least one dendrite regenerates through EPRO composition treated tissue more effectively than through untreated tissues. According to some such embodiments, the at least one dendrite regenerated extends at least twice as far through EPRO composition treated tissue than at least one dendrite regenerating through untreated tissues.

According to another embodiment, the at least one polypeptide of formula I regenerates at least one dendrite treated with the at least one polypeptide of formula I more effectively than at least one untreated dendrite. According to some such embodiments, the at least one dendrite treated with the at least one polypeptide of formula I extends at least twice as far as at least one untreated dendrite.

According to another embodiment, the EPRO composition is a pharmaceutical composition.

According to another embodiment, the EPRO composition further comprises at least one additional active agent.

6. Methods for Protecting Against Progression of a Neuronal Injury or Neuronal Degeneration According to another aspect, the described invention provides a method for protecting at least one neuron from progression of a neuronal injury, the method comprising: (a) providing a therapeutically effective amount of an EPRO composition, the composition comprising: (i) at least one polypeptide having an amino acid sequence according to Formula I:

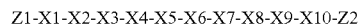

Z1-X1-X2-X3-X4-X5-X6-X7-X8-X9-X10-Z2 wherein Z1 and Z2 are independently absent or are transduction domains; X1 is selected from the group consisting of A, KA, KKA, KKKA and RA, or is absent; X2 is selected from the group consisting of G, L, A, V, I, M, Y, W and F, or is an aliphatic amino acid; X3 is selected from the group consisting of V, L, I, A, G, Q, N, S, T and C, or is an aliphatic amino acid; X4 is selected from the group consisting of Q, N, H, R and K; X5 is selected from the group consisting of Q and N; X6 is selected from the group consisting of C, A, G, L, V, I, M, Y, W and F or is an aliphatic amino acid; X7 is selected from the group consisting of S, A, C, T and G or is an aliphatic amino acid; X8 is selected from the group consisting of V, L, I and M; X9 is absent or is any amino acid; X10 is absent or is any amino acid; wherein at least one of the following is true: (a) X3 is N and X7 is not G; (b) X7 is G and X3 is not N; (c) X2 is not L; (d) X4 is not R; (e) X5 is not Q; (f) X6 is not L; (g) X8 is not V; (h) X10 is absent; (i) X9 and X10 are absent;

and
(ii) a carrier;
(b) administering the composition to a subject in need thereof; and
(c) reducing or inhibiting at least one manifestation of progression of the neuronal injury in at least one neuronal cell population affected by the neuronal injury; and
(d) increasing survival of the at least one neuronal cell population affected by the neuronal injury.

According to one embodiment, the injury is a neurapraxia type injury. According to another embodiment, the injury is a axonotmesis type injury. According to another embodiment, the injury is a neurtmesis type injury. According to another embodiment, the injury results from an acute disorder. According to another embodiment, the acute disorder is a stroke, a spinal cord injury, or a traumatic brain injury. According to another embodiment, the injury results from a chronic neurodegenerative disease. According to another embodiment, the chronic neurodegenerative disease is Parkinson's disease, Alzheimer's disease, Multiple Sclerosis, Amyotrophic lateral sclerosis. or a neuropathy. According to another such embodiment, the neuropathy is a diabetic neuropathy. According to another embodiment, the at least one manifestation of progression of the neuronal injury to at least one neuronal cell population is apoptotic cell death. According to another embodiment, the at least one manifestation of progression of the neuronal injury to at least one neuronal cell population is microglial activation. According to another embodiment, the at least one manifestation of progression of the neuronal injury to at least one neuronal cell population is inflammation. According to another embodiment, the at least one manifestation of progression of the neuronal injury to at least one neuronal cell population is formation of a scar. According to another embodiment, the scar is a glial scar. According to another embodiment, the neuronal cell population is a cortical cell population. According to another embodiment, the neuronal cell population is a motor neuron cell population. According to another embodiment, the neuronal cell population is a sensory neuron cell population. According to some embodiments, the neuronal cell population is a mixed cortical cell population. According to some such embodiments, the mixed cortical cell population comprises neurons, microglia, and astrocytes. According to another embodiment, the at least one neuropathy is a peripheral neuropathy. According to another embodiment, the at least one neuropathy is a autonomic peripheral neuropathy.

According to another embodiment, in addition to the recited amino acids, X2, X3, X6 and X7 can be any aliphatic amino acid (whether naturally occurring or not), including, but not limited to, beta-alanine and 2-aminocyclohexane-1-carboxylic acid.

According to another embodiment, X4 is R; X5 is Q, and/or X8 is V. According to another embodiment, X3 is selected from the group consisting of V, L, I, A, G, Q and N. According to another embodiment, X6 is selected from the group consisting of C, A, G, L, V, I, M, Y, W and F. According to another embodiment, X7 is selected from the group consisting of S, A, C, T and G.

According to another embodiment, at least one of Z1 and Z2 is a transduction domain. According to another embodiment, the transduction domain(s) is/are selected from the group consisting of: (R)4-9 [SEQ ID NO: 1]; GRKKRRQRRRPPQ [SEQ ID NO: 2]; RQRRKKRG [SEQ ID NO: 3]; GRKKRRQR [SEQ ID NO: 4]; AYARAAARQARA [SEQ ID NO: 5]; DAATATRGRSAASRPTERPRAPARSASRPRRPVE [SEQ ID NO: 6]; GWTLNSAGYLLGLINLKALAALAKKIL [SEQ ID NO: 7]; PLSSIFSRIGDP [SEQ ID NO: 8]; AAVALLPAVLLALLAP [SEQ ID NO: 9]; AAVLLPVLLAAP [SEQ ID NO: 10]; VTVLALGALAGVGVG [SEQ ID NO: 11; GALFLGWLGAAGSTMGAWSQP [SEQ ID NO: 12]; GWTLNSAGYLLGLINLKALAALAKKIL [SEQ ID NO: 7]; KLALKLALKALKAALKLA [SEQ ID NO: 13]; KETWWETWWTEWSQPKKKRKV [SEQ ID NO: 14]; KAFAKLAARLYRKA [SEQ ID NO: 15]; KAFAKLAARLYRAA [SEQ ID NO: 16]; AAFAKLAARLYRKA [SEQ ID NO: 17]; KAFAALAARLYRKA [SEQ ID NO: 18]; KAFAKLAARLYRKAGC [SEQ ID NO: 20]; KAFAKLAARLYRAAGC [SEQ ID NO: 21]; AAFAKLAARLYRKAGC [SEQ ID NO: 22]; KAFAALAARLYRKAGC [SEQ ID NO: 23]; KAFAKLAAQLYRKAGC [SEQ ID NO: 24]; AGGGGYGRKKRRQRRR [SEQ ID NO: 25]; YARAAAARQARA [SEQ ID NO: 26]; YGRKKRRQRRR [SEQ ID NO: 27]; WLRRIKAWLRRIKA [SEQ ID NO: 28]; WLRRIKAWLRRIKAWLRRIKA [SEQ ID NO: 29]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, exemplary polypeptides according to the invention include, but are not limited to any of those listed above, wherein one or both of Z1 and Z2 are selected from the group consisting of: WLRRIKAWLRRIKA [SEQ ID NO: 28]; WLRRIKAWLRRIKAWLRRIKA [SEQ ID NO: 29]; YGRKKRRQRRR [SEQ ID NO: 27]; YARAAAARQARA [SEQ ID NO: 26]; RQRRKKRG [SEQ ID NO: 3]; GRKKRRQR [SEQ ID NO: 4]; KAFAKLAARLYRKA [SEQ ID NO: 15]; FAKLAARLYRKA [SEQ ID NO: 30]; KAFAALAARLYRKA [SEQ ID NO: 18]; KAFAKLAARLYRAA [SEQ ID NO: 16]; KAFAKLAARLYRA [SEQ ID NO: 19]; FAKLAARLYRAA [SEQ ID NO: 31]; and FAKLAARLYRA [SEQ ID NO: 32].

According to another embodiment, the at least one polypeptide of formula I comprises YARAAARQARAKALARQLGVAA [SEQ ID NO: 33]; YGRKKRRQRRRKALARQLGVAA [SEQ ID NO: 34]; RQRRKKRGKALARQLGVAA [SEQ ID NO: 35]; GRKKRRQRKALARQLGVAA [SEQ ID NO: 36]; WLRRIKAWLRRIKAKALARQLGVAA [SEQ ID NO: 37]; WLRRIKAWLRIKAWLRRIKAKALARQLGVAA [SEQ ID NO: 38]; YARAAARQARAKKKALARQLGVAA [SEQ ID NO: 39]; YGRKKRRQRRRKKKALARQLGVAA [SEQ ID NO: 40]; RQRRKKRGKKKALARQLGVAA [SEQ ID NO: 41]; GRKKRRQRKKKALARQLGVAA [SEQ ID NO: 42]; WLRRIKAWLRRIKAKKKALARQLGVAA [SEQ ID NO: 43]; WLRRIKAWLRRIKAWLRRIKAKKKALARQLGVAA [SEQ ID NO: 44]; KAFAKLAARLYRKALARQLGVAA [SEQ ID NO: 45]; FAKLAARLYRKALARQLGVAA [SEQ ID NO: 46]; KAFAKLAARLYRAALARQLGVAA [SEQ ID NO: 47]; KAFAKLAARLYRALARQLGVAA [SEQ ID NO: 48]; KAFAALAARLYRAALARQLGVAA [SEQ ID NO: 49]; FAKLAARLYRAALARQLGVAA [SEQ ID NO: 50]; WLRRIKAWRRIKA-LNRQLGVAA; YARAAARQARAKALNRQLGVA [SEQ ID NO: 51]; KAFAKLAARLYRKALNRQLAVAA [SEQ ID NO: 52]; FAKLAARLYRKALNRQLAVAA [SEQ ID NO: 53]; KAFALKAARLYRKA-LNRQLGVAA; and FAKLAARLYRKA-LNRQLGVAA.

Further exemplary peptides include WLRRIKAWRRIKALNRQLGVA [SEQ ID NO: 56], KAFALKAARLYRKALNRQLGVA [SEQ ID NO: 57], and FAKLAARLYRKALNRQLGVA [SEQ ID NO: 58].

Further exemplary polypeptides according to the invention include, but are not limited to, those comprising or consisting of: KALNRQLGVA [SEQ ID NO: 54], and KALNRQLGVA [SEQ ID NO: 55].

According to another embodiment, the at least one polypeptide of formula I of the EPRO composition is a peptide of amino sequence YARAAARQARAKALARQLGVAA [SEQ ID NO: 33]. According to another embodiment, the at least one polypeptide of formula I of the EPRO composition is a peptide of amino acid sequence YARAAARQARAKALNRQLGVA [SEQ ID NO: 51]. According to another embodiment, the at least one polypeptide of formula I of the EPRO composition is a peptide of amino acid sequence FAKLAARLYRKALARQLGVAA [SEQ ID NO: 46].

According to another embodiment, the at least one polypeptide of formula I of the EPRO composition is a peptide of amino acid sequence YARAAARQARAKALNRQLGVAA [SEQ ID NO: 59]. According to another embodiment, the at least one polypeptide of formula I of the EPRO composition is a peptide of amino acid sequence FAKLAARLYRKLALRQLGVAA [SEQ ID NO: 60].

According to one embodiment, the at least one polypeptide has an amino acid sequence of at least 70% sequence identity to an amino acid sequence according to Formula I. According to one embodiment, the at least one polypeptide has an amino acid sequence of at least 75% sequence identity to an amino acid sequence according to Formula I. According to one embodiment, the at least one polypeptide has an amino acid sequence of at least 80% sequence identity to an amino acid sequence according to Formula I. According to one embodiment, the at least one polypeptide has an amino acid sequence of at least 85% sequence identity to an amino acid sequence according to Formula I.

According to some embodiments, the at least one polypeptide has at least about 70% sequence identity to amino acid sequence YARAAARQARAKALARQLGVAA [SEQ ID NO: 33]. According to some embodiments, the at least one polypeptide has at least about 75% sequence identity to amino acid sequence YARAAARQARAKALARQLGVAA [SEQ ID NO: 33]. According to some embodiments, the at least one polypeptide has at least about 80% sequence identity to amino acid sequence YARAAARQARAKALARQLGVAA [SEQ ID NO: 33]. According to some embodiments, the at least one polypeptide has at least about 85% sequence identity to amino acid sequence YARAAARQARAKALARQLGVAA [SEQ ID NO: 33].

According to some embodiments, the at least one polypeptide has at least about 70% sequence identity to amino acid sequence YARAAARQARAKALNRQLGVA [SEQ ID NO: 51]. According to some embodiments, the at least one polypeptide has at least about 75% sequence identity to amino acid sequence YARAAARQARAKALNRQLGVA [SEQ ID NO: 51]. According to some embodiments, the at least one polypeptide has at least about 80% sequence identity to amino acid sequence YARAAARQARAKALNRQLGVA [SEQ ID NO: 51]. According to some embodiments, the at least one polypeptide has at least about 85% sequence identity to amino acid sequence YARAAARQARAKALNRQLGVA [SEQ ID NO: 51].

According to some embodiments, the at least one polypeptide has at least about 70% sequence identity to amino acid sequence YARAAARQARAKALNRQLGVAA [SEQ ID NO: 59]. According to some embodiments, the at least one polypeptide has at least about 75% sequence identity to amino acid sequence YARAAARQARAKALNRQLGVAA [SEQ ID NO: 59]. According to some embodiments, the at least one polypeptide has at least about 80% sequence identity to amino acid sequence YARAAARQARAKALNRQLGVAA [SEQ ID NO: 59]. According to some embodiments, the at least one polypeptide has at least about 85% sequence identity to amino acid sequence YARAAARQARAKALNRQLGVAA [SEQ ID NO: 59].

According to some embodiments, the at least one polypeptide has at least about 70% sequence identity to amino acid sequence FAKLAARLYRKALARQLGVAA [SEQ ID NO: 46]. According to some embodiments, the at least one polypeptide has at least about 75% sequence identity to amino acid sequence FAKLAARLYRKALARQLGVAA [SEQ ID NO: 46]. According to some embodiments, the at least one polypeptide has at least about 80% sequence identity to amino acid sequence FAKLAARLYRKALARQLGVAA [SEQ ID NO: 46]. According to some embodiments, the at least one polypeptide has at least about 85% sequence identity to amino acid sequence FAKLAARLYRKALARQLGVAA [SEQ ID NO: 46].

According to some embodiments, the at least one polypeptide has at least about 70% sequence identity to amino acid sequence FAKLAARLYRKLALRQLGVAA [SEQ ID NO: 60]. According to some embodiments, the at least one polypeptide has at least about 75% sequence identity to amino acid sequence FAKLAARLYRKLALRQLGVAA [SEQ ID NO: 60]. According to some embodiments, the at least one polypeptide has at least about 80% sequence identity to amino acid sequence FAKLAARLYRKLALRQLGVAA [SEQ ID NO: 60]. According to some embodiments, the at least one polypeptide has at least about 85% sequence identity to amino acid sequence FAKLAARLYRKLALRQLGVAA [SEQ ID NO: 60].

According to another embodiment, the reducing or inhibiting of the at least one manifestation of progression of the neuronal injury is by at least 10% relative to the manifestation of progression of the neuronal injury within at least one neuronal cell population that has not been treated with the EPRO composition. According to another embodiment, the reducing or inhibiting of the at least one manifestation of progression of the neuronal injury is by at least 20% relative to the manifestation of progression of the neuronal injury within at least one neuronal cell population that has not been treated with the EPRO composition. According to another embodiment, the reducing or inhibiting of the at least one manifestation of progression of the neuronal injury is by at least 30% relative to the manifestation of progression of the neuronal injury within at least one neuronal cell population that has not been treated with the EPRO composition. According to another embodiment, the reducing or inhibiting of the at least one manifestation of progression of the neuronal injury is by at least 40% relative to the manifestation of progression of the neuronal injury within at least one neuronal cell population that has not been treated with the EPRO composition. According to another embodiment, the reducing or inhibiting of the at least one manifestation of progression of the neuronal injury is by at least 50% relative to the manifestation of progression of the neuronal injury within at least one neuronal cell population that has not been treated with the EPRO composition. According to another embodiment, the reducing or inhibiting of the at least one manifestation of progression of the neuronal injury is by at least 60% relative to the manifestation of progression of the neuronal injury within at least one neuronal cell population that has not been treated with the EPRO composition. According to another embodiment, the reducing or inhibiting of the at least one manifestation of progression of the neuronal injury is by at least 70% relative to the manifestation of progression of the neuronal injury within at least one neuronal cell population that has not been treated with the EPRO composition. According to another embodiment, the reducing or inhibiting of the at least one manifestation of progression of the neuronal injury is by at least 80% relative to the manifestation of progression of the neuronal injury within at least one neuronal cell population that has not been treated with the EPRO composition. According to another embodiment, the reducing or inhibiting of the at least one manifestation of progression of the neuronal injury is by at least 90% relative to the manifestation of progression of the neuronal injury within at least one neuronal cell population that has not been treated with the EPRO composition. According to another embodiment, the reducing or inhibiting of the at least one manifestation of progression of the neuronal injury is by at least 95% relative to the manifestation of progression of the neuronal injury within at least one neuronal cell population that has not been treated with the EPRO composition.

According to another embodiment, the EPRO composition protects at least one neuron from progression of a neuronal injury by inhibiting expression of at least one inflammatory cytokine from activated microglia. According to another embodiment, the at least one inflammatory cytokine is at least one of IL-1 beta, IL-6, and TNF-alpha.

According to another embodiment, the EPRO composition is a pharmaceutical composition.

General methods in molecular genetics and genetic engineering useful in the present invention are described in the current editions of *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), and *Gene Transfer and Expression Protocols*, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any method and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be considered as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Peptide Synthesis and Purification

The MAPKAP kinase 2 inhibitor (MK2i) peptide having sequence [SEQ ID NO: 33] was synthesized on Rink-amide resin using standard fluorenyl methyloxy carboxyl (FMOC) chemistry on a Protein Technologies Symphony Peptide Synthesizer (Protein Technologies, Inc., Tucson, Ariz.). Following synthesis, the peptide was cleaved from the resin with a trifluoroacetic acid (TFA)-based cocktail, precipitated in ether, and recovered by centrifugation. The recovered peptide was dried overnight in vacuum, re-suspended in MilliQ-purified water, then purified using an fast protein liquid chromatography (FPLC) system (AKTA Explorer, GE Healthcare) equipped with a 22/250 C18 prep-scale column (Grace Davidson, Deerfield, Ill.). An acetonitrile gradient was used to achieve separation. A small sample of peptide was solubilized in TFA (0.1%), water (50%) and acetonitrile (about 50%) and the molecular weight confirmed by time-of-flight matrix-assisted laser desorption/ionization (MALDI) mass spectrometry. Synthesis and concentration of the peptides were confirmed using quantitative amino acid analysis.

Example 2. Effect of MAPKAP Kinase 2 Inhibition (MK2i) on Neurite Outgrowth

The effect of an MAPKAP Kinase 2 inhibitor (MK2i) on neurite outgrowth was studied using mixed cortical cells (neurons, microglia, astrocytes) isolated from E18 Sprague Dawley rat cortices. Briefly, the tissue was dissociated and the isolated cortical cells were cultured in polylysine-coated 96-well plates. After culture for 24 hours, the cortical cells were exposed to 100 mM MK2i peptide YARAAAR-QARAKALARQLGVAA [SEQ ID NO: 33] or to regular media (control) for 5 hours. Phase contrast images of individual neurons were acquired and neurite length was quantified by tracing individual neurons using ImageJ software (Collins, T J (July 2007); "ImageJ for microscopy", *Biotechniques.* 43 (1 Suppl):25-30).

FIG. 1 shows a graph of the mean neurite length ($\mu$m) of the control neurons (n=160 neurites) and of the MK2i peptide YARAAARQARAKALARQLGVAA [SEQ ID NO: 33] exposed neurons (n=113 neurites). Statistical evaluation included a Kolmogorov-Smirnov test to confirm the distribution was normal, as well as a t-test with an alpha value of 0.01. The statistical evaluation shows that the mean of the neurite lengths of MK2i-treated neurites was significantly larger than that of the control. (p≤0.01)

Example 3. Effect of MAPKAP Kinase 2 Inhibition (MK2i) on Neuronal Cell Death and Microglial Activation The effect of MK2i on neuronal cell death and microglical activation was investigated by treating 1-week old mixed cortical cultures comprising neurons, astrocytes, and microglia with the MK2i peptide YARAAARQARAKALARQL-GVAA [SEQ ID NO: 33]. Primary Cortical Cell Culture Embryonic rat cortical tissue was obtained immediately following removal of embryos from the rat's abdomen. E17 Sprague-Dawley rat cortical tissue was placed in a 50 ml conical tube containing 5 ml of Solution 1 (NaCl 7.24 g/L; KCl 0.4 g/L; NaH$_2$PO$_4$ 0.14 g/L; Glucose 2.61 g/L; Hepes 5.96 g/L; MgSO$_4$ 0.295 g/L; Bovine Serum Albumin 3 g/L). Under sterile conditions, 18 µl of trypsin solution (7.5 mg/ml in 0.9% saline) was added and tissue was passed through a 5-ml pipet several times to disassociate tissue. After the conical tube was placed in a 37° C. water bath for 20 minutes, 100 µl of trypsin inhibitor/DNAse solution (2.5 mg/ml trypsin inhibitor, 400 µg/ml DNase in 0.9% saline) was added to the tube and tissue was pipetted several times with a 5-ml pipet. Tissue was centrifuged at 1,000 rpm for 5 minutes at room temperature and supernatant was poured off. Cells were re-suspended in 16 ml of Hibernate E (BrainBits, Springfield, Ill.) and 100 µl of trypsin inhibitor/ DNAse solution and pipetted up and down several times. Cells were filtered through a cell strainer and centrifuged at 1,400 rpm for 5 minutes at room temperature. Supernatant was poured off and cells were re-suspended in media. Primary cells were then plated in poly-D-lysine coated 96-well plates at a seeding density of 625,000 cells/cm$^2$ and incubated for 7-9 days at 37° C. After 7-9 days, cortical cells were treated with 5 ng/ml or 10 ng/ml of TNF-α to activate microglia. Cells then were treated with 0, 0.5, 1, or 3 mM MK2i peptide YARAAARQARAKALARQLGVAA [SEQ ID NO: 33] for 4 hours, 8 hours, and 24 hours. After treatment, media was removed and stored at −20° C.

Immunocytochemistry

In preparation for staining mixed cortical cells, cell media was replaced with phosphate-buffered 4% formaldehyde solution for 5 minutes, followed by three washes using HBHS solution (HEPES-buffered Hank's saline containing 10 mg/L sodium azide, pH 7.4). Blocking solution, consisting of 10% normal goat serum in HBHS, then was applied for 30 minutes, followed by three washes with HBHS. Microglia, astrocytes, and neurons were labeled using antibodies against ionized calcium binding adaptor molecule 1 (Iba1, Wako), glial fibrillary acidic protein (GFAP, Millipore), and β-3-tubulin (β3tub, Covance), respectively. Antibodies were applied for 2 hours, at a dilution of 1:400 in HBHS. After two 10 minute washes and one 30 minute wash, secondary antibodies were applied. Alexafluor 488 goat-anti-mouse, Alexafluor 555 goat-anti-chicken, and Alexafluor 635 goat anti-rabbit (all from Invitrogen, Carlsbad, Calif.) were applied at 1:400 along with Hoescht 33342 at approximately 1:10000 (Invitrogen, Carlsbad, Calif.) in HBHS for 2 hours. All immunocytochemistry procedures were performed at room temperature, and stored at 4° C. in HBHS+sodiumazide prior to imaging.

Cell Imaging

Cell imaging was accomplished using an Olympus IX81 microscope equipped with an Olympus FV1000 laser confocal system through Olympus 10x/0.40x/0.80 water emersion objectives. Image channels were collected sequentially using 488 nm, 543 nm, and 633 nm laser lines, along with a tunable MaiTai laser (Spectra Physics) set to 740 nm. Two-photon excitation of Hoescht 33342 was driven by this 740 nm excitation, and the emission was collected by an external PMT (R3896, Hamamatsu) equipped with a 405/40 nm filter (Chroma)). Internal detectors collected all other channels. A wide aperture setting (400 µm) was used to capture representative images from the labeled 2D cultures; laser power and PMT voltage settings were held constant. Related image channels levels were set equal, allowing visual comparison of fluorescent intensity, using Olympus Fluoview V1.7 software. Scale bars were added and figures were designed using Photoshop CS2 (Adobe).

Live-Dead Assay

Live-dead assays were conducted using Molecular Probe's LIVE/DEAD® Viability/Cytotoxicity Kit for Mammalian Cells to quantify the change in toxicity in cortical cell cultures following the MK2i peptide YARAAAR-QARAKALARQLGVAA [SEQ ID NO: 33] treatment. Prior to experiments, optimal concentration of the live cell dye, Calcein-AM (CA), and the dead cell dye (Ethidium-1) was determined to be 6 mM. Also, optimal time for dye incubation was 30 minutes.

One-half hour before the 24-hour time point, untreated cultures were killed with a 30-minute 70% ethanol treatment. One group of control dead cells received 100 µl of the 6 mM CA solution to determine the background fluorescence of CA. A second group of control dead cells received 100 µl of the 6 mM EthD-1 solution to determine the maximum fluorescence for EthD-1. Conversely, one group of control live cells received 100 µl of the 6 mM EthD-1 solution to determine the background fluorescence of EthD-1, while a second group of control live cells received 100 µl of the 6 mM CA solution to determine the maximum fluorescence for CA.

At the 24 hour time point, cultures were washed twice with 250 µl 1×PBS. Then, 100 µl of a 6 mM EthD-1/6 mM CA working solution was added to each treated well. Fluorescence was measured then using a Spectramax M5 Microplate Reader (Molecular Devices). EthD-1 required an excitation wavelength of 530 nm and an emission wavelength of 645 nm. CA required an excitation wavelength of 485 nm and an emission wavelength of 530 nm.

Figure 2B:
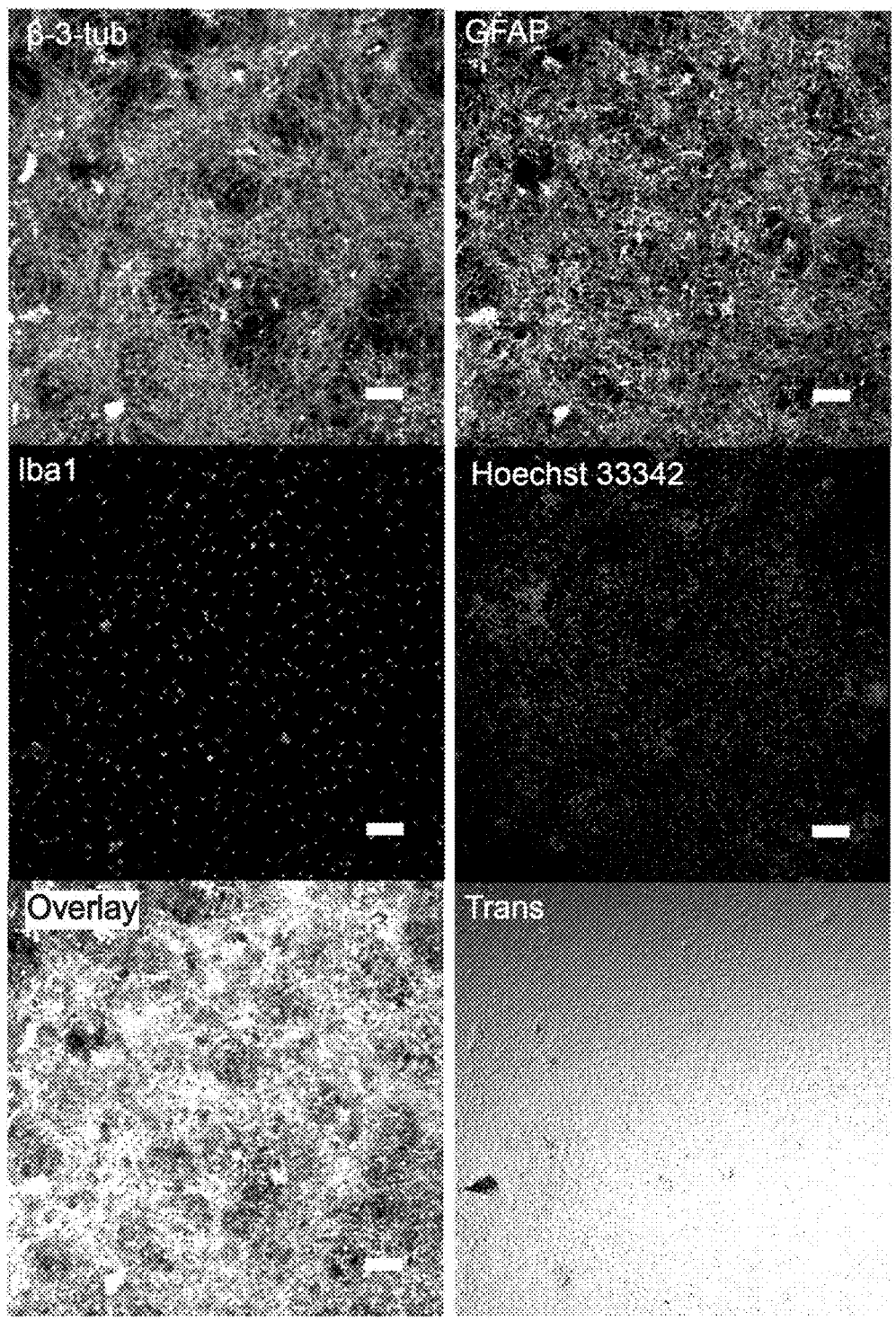
Figure 3:
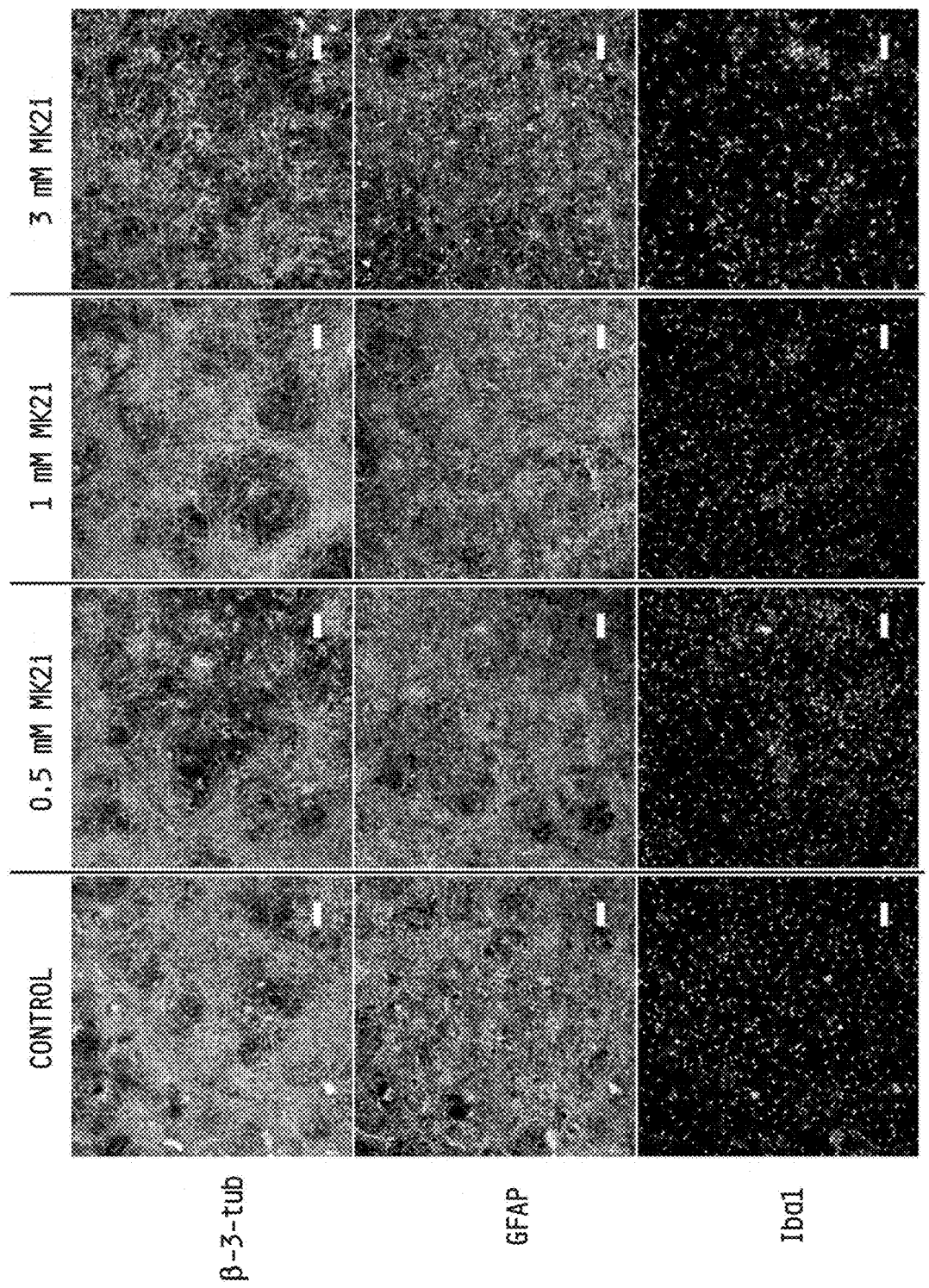
FIG. 3 shows micrographs of neurons (β-3-tub), astrocytes (GFAP), and microglia (Iba1), treated with 0 mM MK2i (YARAAARQARAKALARQLGVAA [SEQ ID NO: 33]), 0.5 mM MK2i, 1.0 mM MK2i, and 3 mM MK2i. Scale bar is 100 μm.
Figure 4:
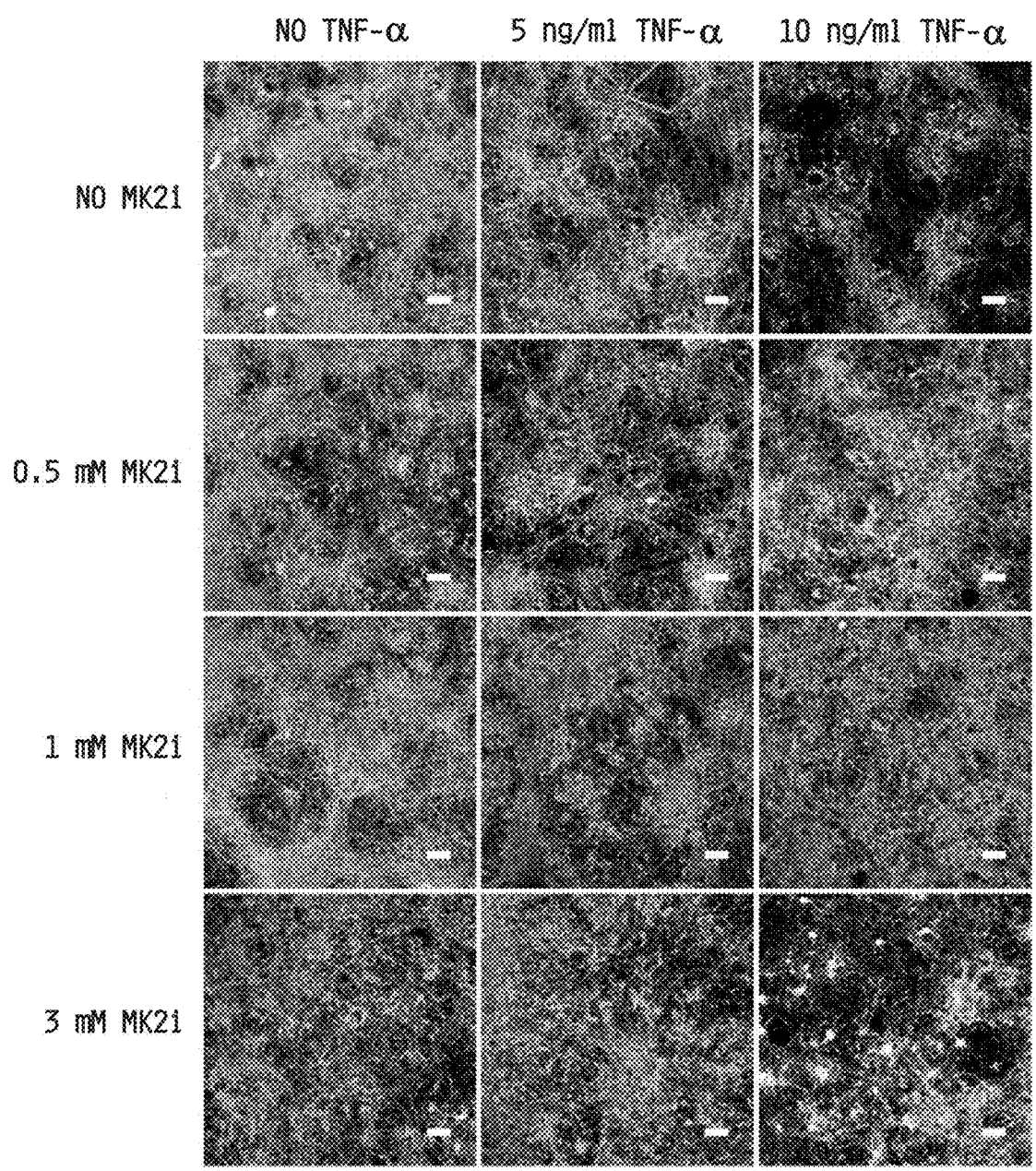
FIG. 4 shows micrographs of neurons treated with MK2i (YARAAARQARAKALARQLGVAA [SEQ ID NO: 33]) and TNF-α. Row 1 shows neurons treated with 0 mM MK2i and 0 ng/ml TNF-α, 5 ng/ml TNF-α, and 10 ng/ml TNF-α, respectively; Row 2 shows neurons treated with 0.5 mM MK2i and 0 ng/ml TNF-α, 5 ng/ml TNF-α, and 10 ng/ml TNF-α, respectively; Row 3 shows neurons treated with 1 mM MK2i and 0 ng/ml TNF-α, 5 ng/ml TNF-α, and 10 ng/ml TNF-α, respectively; and Row 4 shows neurons treated with 3 mM MK2i and 0 ng/ml TNF-α, 5 ng/ml TNF-α, and 10 ng/ml TNF-α, respectively. Scale bar is 100 μm.
Figure 5:
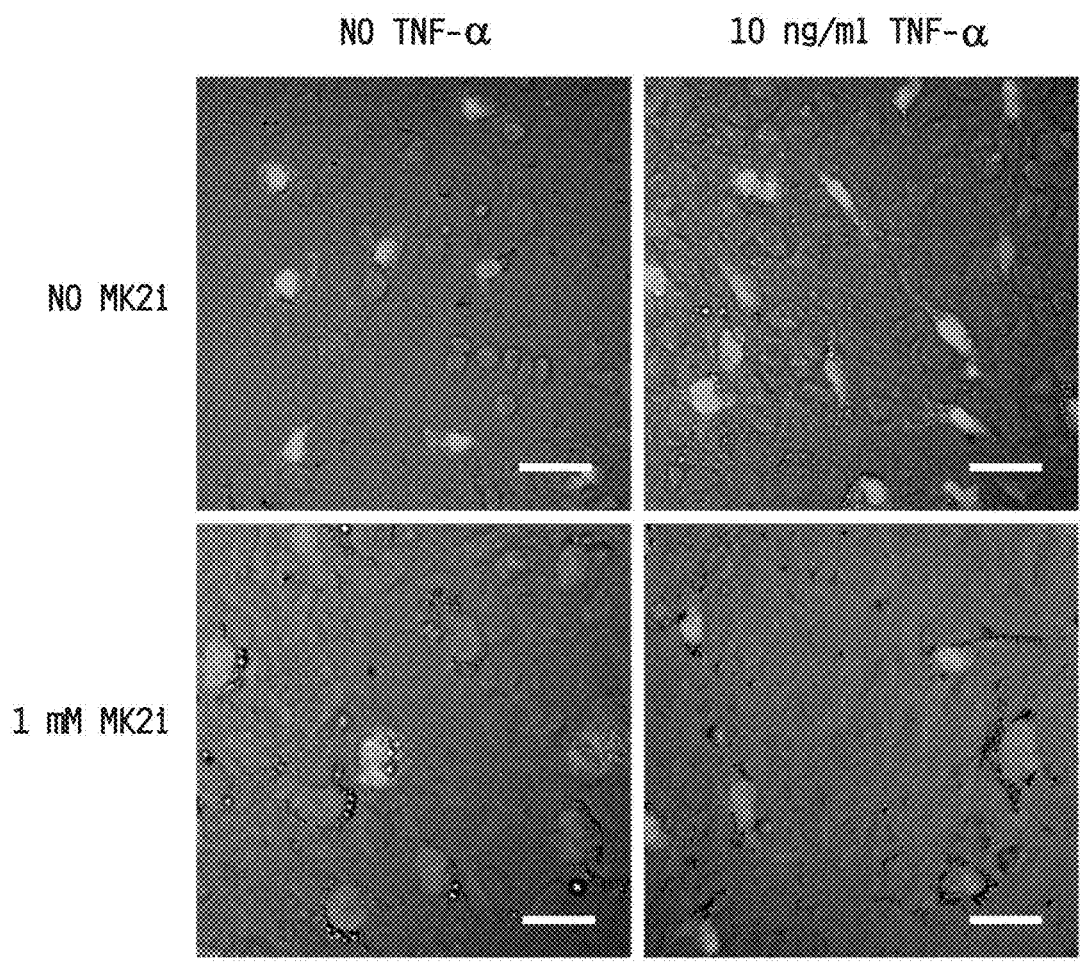
FIG. 5 shows micrographs of microglia treated with TNF-α and MK2i (YARAAARQARAKALARQLGVAA [SEQ ID NO: 33]). Row 1 shows non-MK2i-treated microglia (control) exposed to 0 ng/ml TNF-α and 10 ng/ml TNF-α; Row 2 shows 1 mM MK2i-treated microglia exposed to 0 ng/ml TNF-α and 10 ng/ml TNF-α. Scale bar is 25 μm.

The MK2i Peptide YARAAARQARAKALARQLGVAA [SEQ ID NO: 33] Reduces Cell Death and Microglial Activation Immunohistochemical images confirmed the presence of neurons, astrocytes, and microglia in 1-week old mixed cortical cultures (FIGS. 2A and 2B), which was maintained following the MK2i peptide YARAAARQARAKALARQL-GVAA [SEQ ID NO: 33] treatment. FIG. 3 shows micrographs of neurons (β-3-tub), astrocytes (GFAP), and microglia (Iba1), treated with 0 mM MK2i (YARAAARQARAKALARQLGVAA [SEQ ID NO: 33]), 0.5 mM MK2i, 1.0 mM MK2i, and 3 mM MK2i. Minimal morphological effects were observed until 3 mM treatment, which increased neuronal and astrocytic cell damage, as well as microglial proliferation. FIG. 4 shows micrographs of neurons treated with MK2i (YARAAARQARAKALARQL-GVAA [SEQ ID NO: 33]) and TNF-α. Row 1 shows neurons treated with 0 mM MK2i and 0 ng/ml TNF-α, 5 ng/ml TNF-α, and 10 ng/ml TNF-α, respectively; Row 2 shows neurons treated with 0.5 mM MK2i and 0 ng/ml TNF-α, 5 ng/ml TNF-α, and 10 ng/ml TNF-α, respectively; Row 3 shows neurons treated with 1 mM MK2i and 0 ng/ml TNF-α, 5 ng/ml TNF-α, and 10 ng/ml TNF-α, respectively;

and Row 4 shows neurons treated with 3 mM MK2i and 0 ng/ml TNF-α, 5 ng/ml TNF-α, and 10 ng/ml TNF-α, respectively. FIG. 4 shows the effect of TNF-α- and MK2i on neurons, indicating that 5 ng/ml and 10 ng/ml TNF-α treatment resulted in significant neuronal cell damage, which was suppressed by 0.5 and 1 mM MK2i. However, this suppression was not maintained at 3 mM MK2i treatment, which also resulted in neuronal cell damage. FIG. 5 shows micrographs of microglia treated with TNF-α and MK2i (YARAAARQARAKALARQLGVAA [SEQ ID NO: 33]), where Row 1 shows non-MK2i-treated microglia (control) exposed to 0 ng/ml TNF-α and 10 ng/ml TNF-α; and Row 2 shows 1 mM MK2i-treated microglia exposed to 0 ng/ml TNF-α and 10 ng/ml TNF-α. FIG. 5 indicates that 24-hr TNF-α treatment induces microglial spreading within mixed cortical cultures, and that 24 hour TNF-α and MK2i treatment induces microglial swelling, but suppresses the microglial spreading caused by TNF-α.

Figure 6:
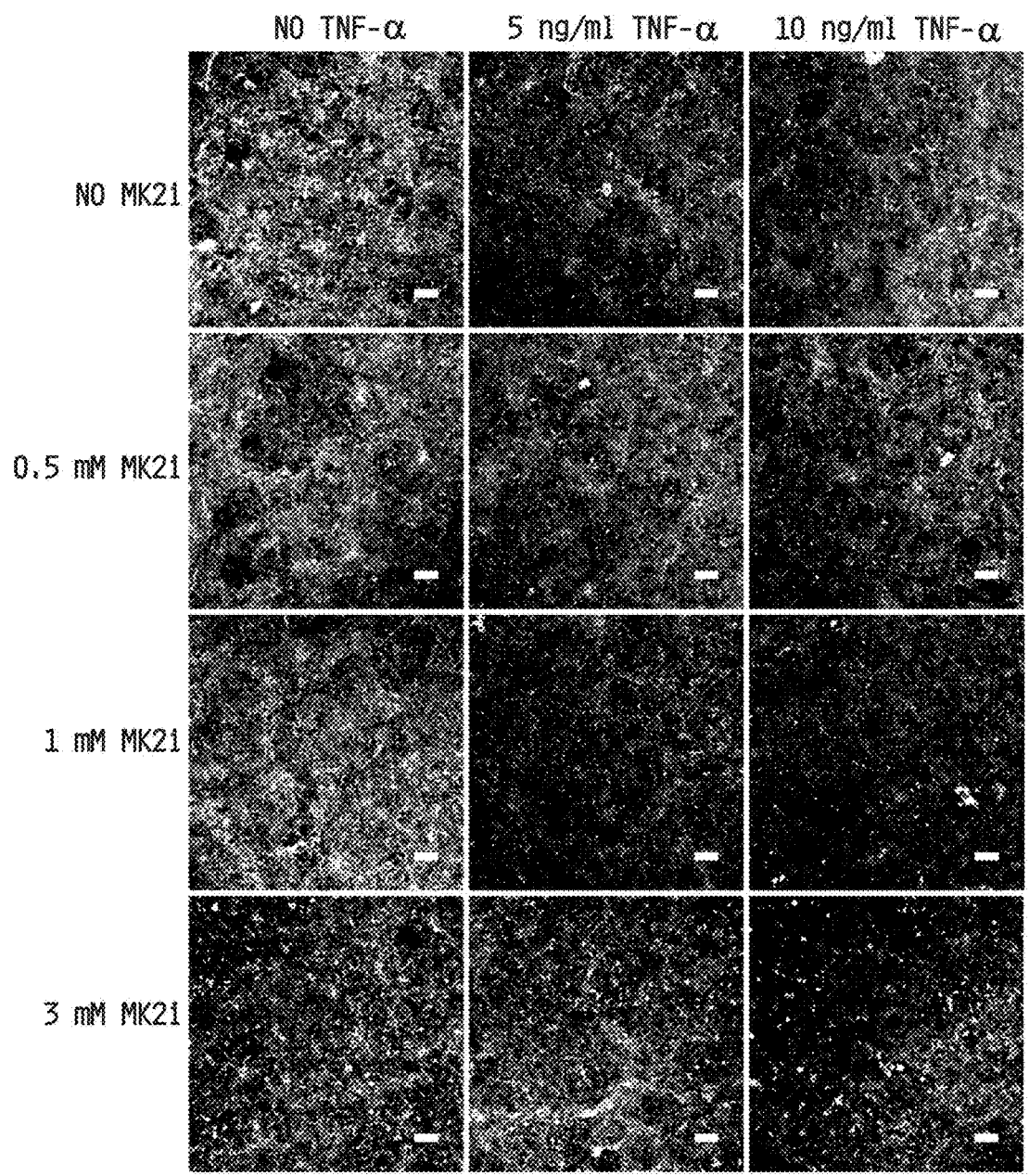
FIG. 6 shows micrographs of astrocytes treated with TNF-α and MK2i (YARAAARQARAKALARQLGVAA [SEQ ID NO: 33]). Row 1 shows non-MK2i-treated astrocytes exposed to 0 ng/ml, 5 ng/ml and 10 ng/ml TNF-α, respectively; Row 2 shows 0.5 mM MK2i-treated astrocytes exposed to 0 ng/ml, 5 ng/ml and 10 ng/ml TNF-α, respectively; Row 3 shows 1 mM MK2i-treated astrocytes exposed to 0 ng/ml, 5 ng/ml and 10 ng/ml TNF-α, respectively; and Row 4 shows 3 mm MK2i-treated astrocytes exposed to 0 ng/ml, 5 ng/ml and 10 ng/ml TNF-α, respectively. Scale bar is 100 μm.
Figure 7A:
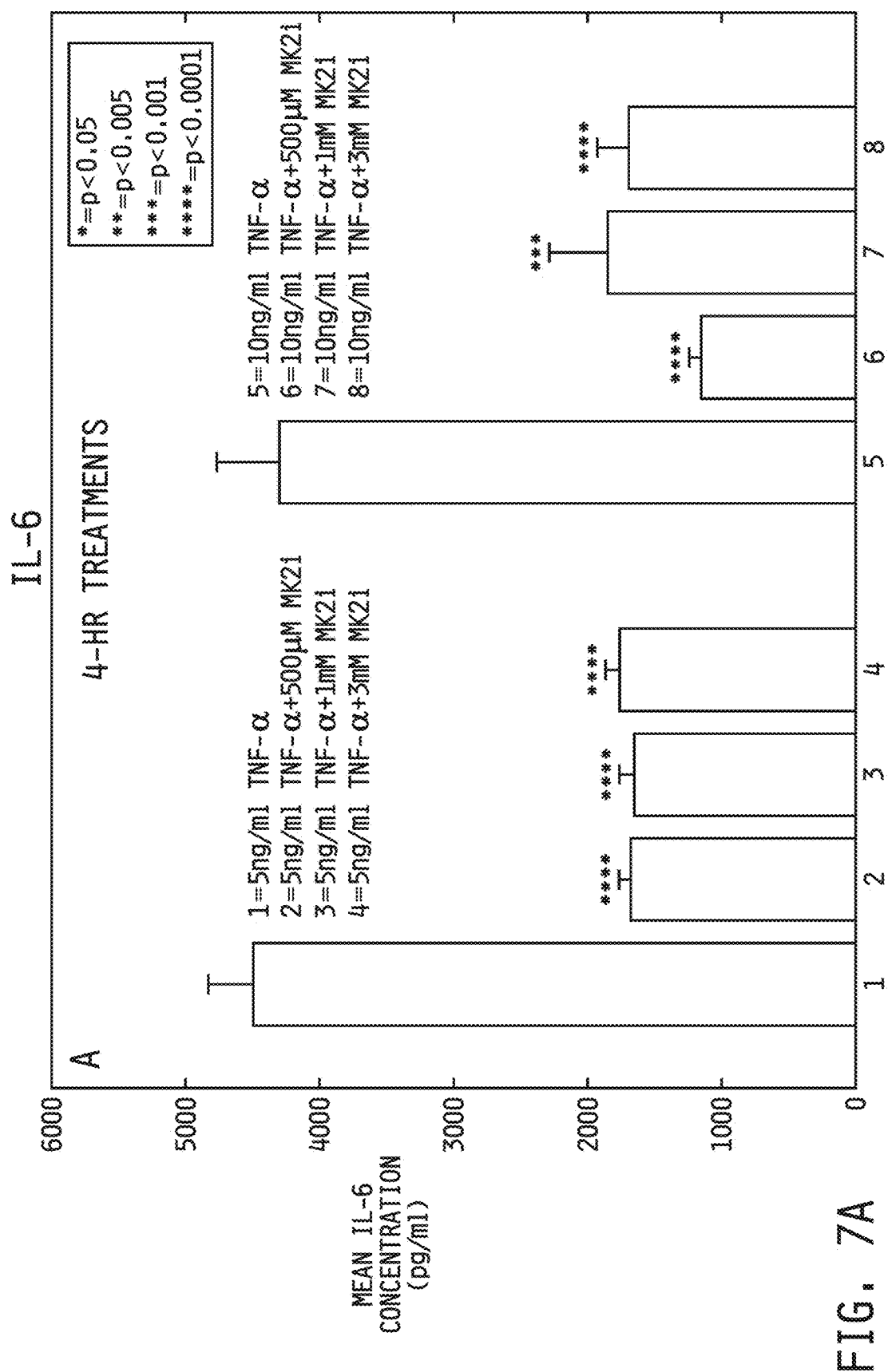
FIG. 7 shows graphs (A-F) of mean concentrations of IL-6 and IL-1β following 4 hour, 8 hour, and 24 hour treatments with TNF-α or TNF-α plus MK2i (YARAAAR-QARAKALARQLGVAA [SEQ ID NO: 33]).
Figure 7B:
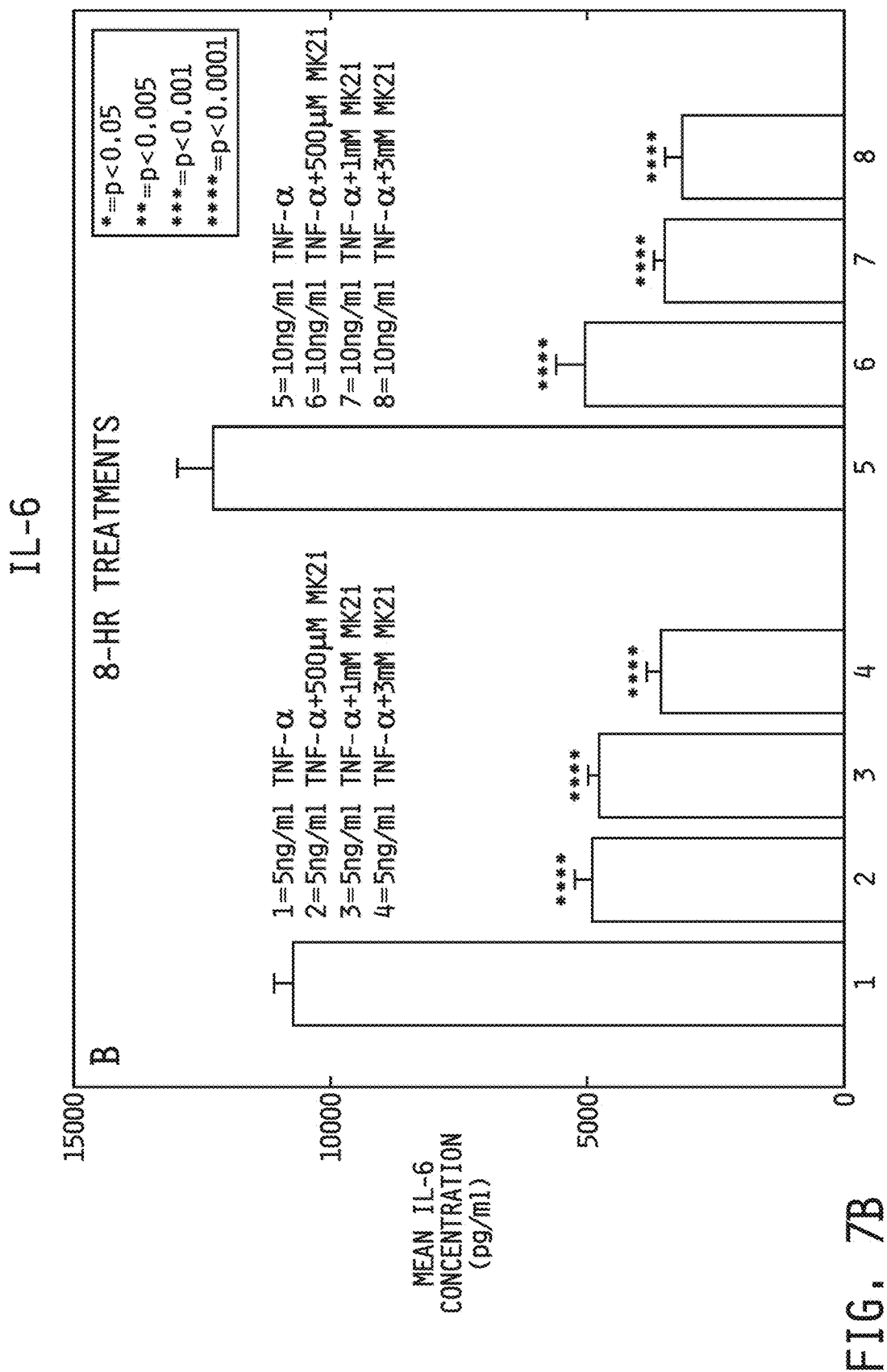
Figure 7D:
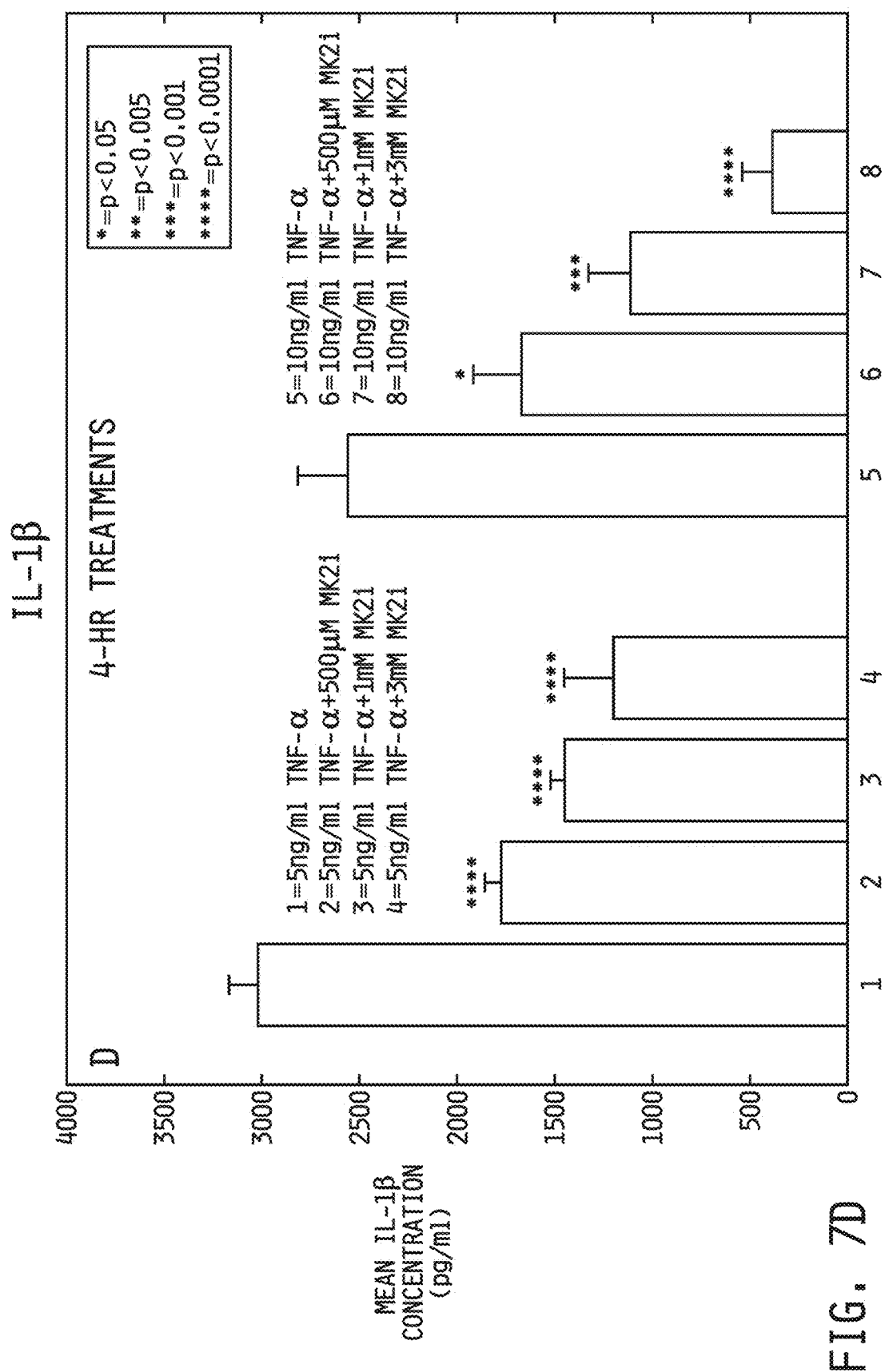
Figure 7E:
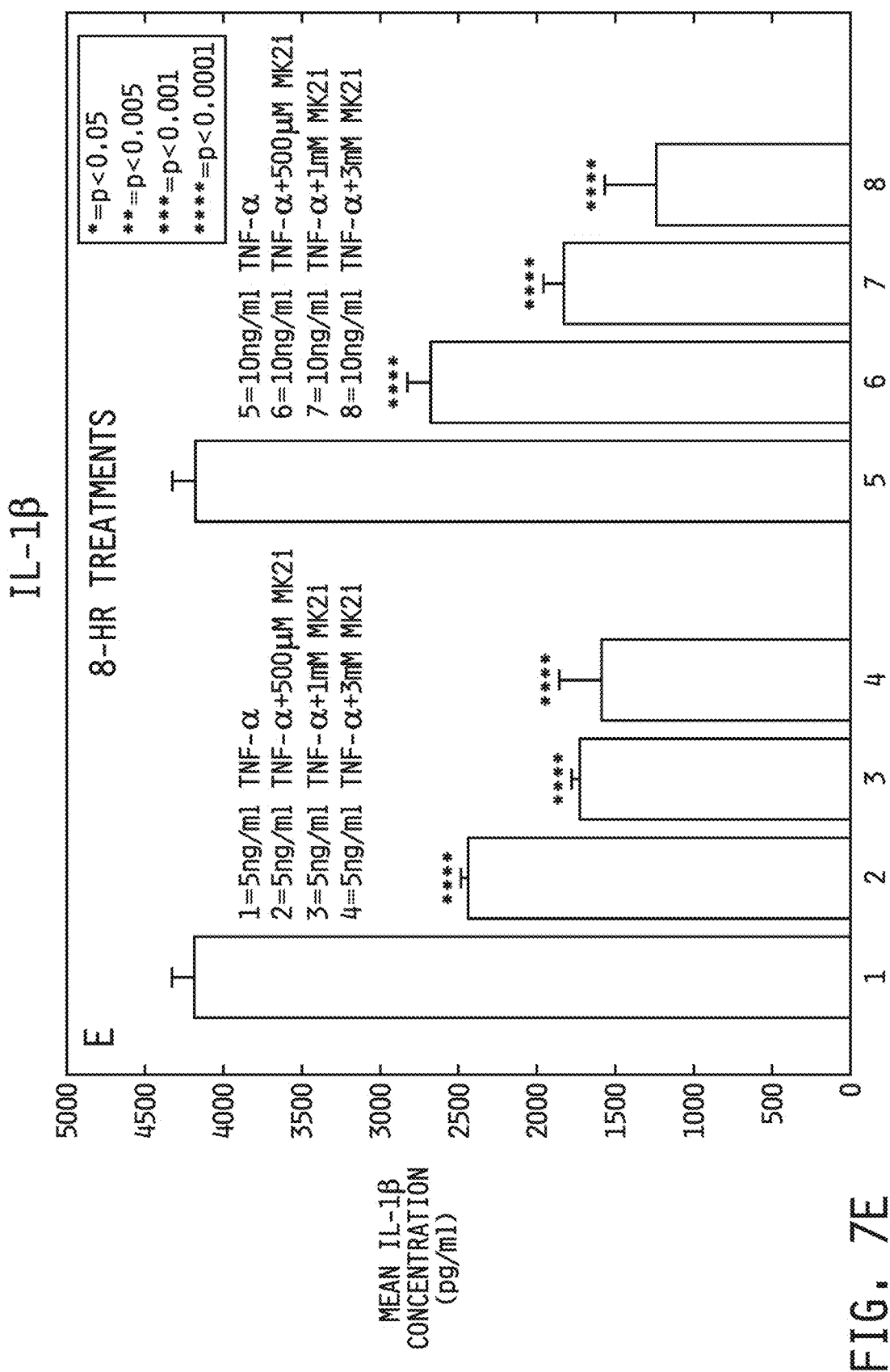
Figure 7F:
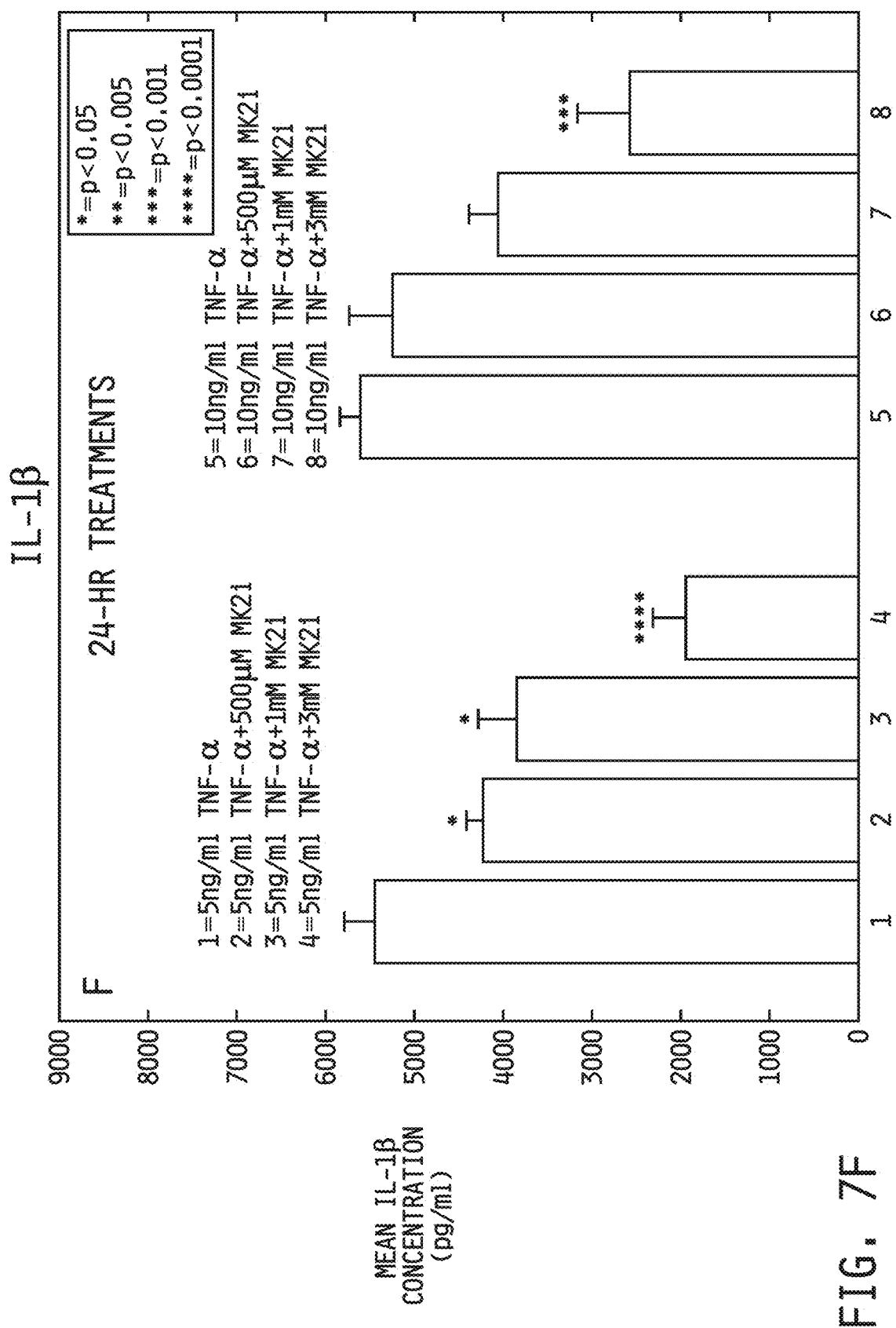

FIG. 6 shows micrographs of astrocytes treated with TNF-α and MK2i (YARAAARQARAKALARQLGVAA [SEQ ID NO: 33]). Row 1 shows non-MK2i-treated astrocytes exposed to 0 ng/ml, 5 ng/ml and 10 ng/ml TNF-α, respectively; Row 2 shows 0.5 mM MK2i-treated astrocytes exposed to 0 ng/ml, 5 ng/ml and 10 ng/ml TNF-α, respectively; Row 3 shows 1 mM MK2i-treated astrocytes exposed to 0 ng/ml, 5 ng/ml and 10 ng/ml TNF-α, respectively; and Row 4 shows 3 mm MK2i-treated astrocytes exposed to 0 ng/ml, 5 ng/ml and 10 ng/ml TNF-α, respectively. FIG. 6 shows damage to astrocytes treated with 3 mM MK2i.

Example 4. The Effect of MAPKAP Kinase 2 Inhibition (MK2i) on IL-6 and IL-1β Expression IL-6 ELISA Assays In order to investigate the effect of MK2i inhibition on IL-6 production, IL-6 ELISA assays were conducted to quantify changes in inflammatory cytokine production using the Rat IL-6 ELISA Development Kit (Peprotech Inc., Rocky Hill, N.J.). 100 µl of 1 µg/ml antigen-affinity purified goat anti-rat IL-6 was added to ELISA microplate wells (NuncMaxisorp) and incubated at room temperature overnight. Wells were washed 4 times with 300 µl wash buffer (0.05% Tween-20 in 1×PBS). 300 µl block buffer (1% BSA in 1×PBS) was added to each well and incubated for 1 hour at room temperature. Block buffer was aspirated and wells were washed 4 times with wash buffer. 8 ng/ml recombinant IL-6 was then diluted to zero in diluent (0.05% Tween-20, 0.1% BSA in 1×PBS). 100 µl of diluted recombinant IL-6 solutions were added in triplicate into microplate wells. 100 µl of media from MK2i treatments also were added to microplate wells. Microplates then were incubated at room temperature for 2 hours, aspirated and washed 4 times with wash buffer. 100 µl of 0.25 µg/ml biotinylated antigen-affinity purified goat anti-rat IL-6 was added to microplate wells and incubated for 2 hours. Microplates were aspirated and washed 4 times with wash buffer. 6 µl Avidin Peroxidase 1:2000 was diluted in 12 ml diluent. 100 µl of this solution was added to wells and incubated for 30 minutes at room temperature, aspirated, and washed 4 times with wash buffer. 100 µl of ABTS Liquid Substrate Solution (Sigma) was added to each well. Absorbance was then measured using a Spectramax M5 Microplate Reader (Molecular Devices). Absorbance values were monitored at 5-minute intervals for 50 minutes.

IL-1β ELISA Assays

In order to quantify changes in inflammatory cytokine (IL-1β) production upon MK2i inhibition, IL-1β ELISA assays were conducted using the Rat IL-1β ELISA Development Kit (Peprotech Inc., Rocky Hill, N.J.). 100 µl of 2 µg/ml antigen-affinity purified goat anti-rat IL-1β was added to ELISA microplate wells (NuncMaxisorp) and incubated at room temperature overnight. Wells were washed 4 times with 300 µl wash buffer (0.05% Tween-20 in 1×PBS). 300 µl block buffer (1% BSA in 1×PBS) was added to each well and incubated for 1 hour at room temperature. Block buffer was aspirated and wells were washed 4 times with wash buffer. 3 ng/ml recombinant IL-1β was then diluted to zero in diluent (0.05% Tween-20, 0.1% BSA in 1×PBS). 100 µl of diluted recombinant IL-1β solutions were added in triplicate into microplate wells. 100 µl of media from MK2i treatments also were added to microplate wells. Microplates were then incubated at room temperature for 2 hours, aspirated and washed 4 times with wash buffer. 100 µl of 0.5 µg/ml biotinylated antigen-affinity purified goat anti-rat IL-1β was added to microplate wells and incubated for 2 hours. Microplates were aspirated and washed 4 times with wash buffer. 5.5 µl Avidin Peroxidase 1:2000 was diluted in 11 ml diluent. 100 µl of this solution was added to wells and incubated for 30 minutes at room temperature, aspirated, and washed 4 times with wash buffer. 100 µl of ABTS Liquid Substrate Solution (Sigma) was added to each well. Absorbance was then measured using a Spectramax M5 Microplate Reader (Molecular Devices). Absorbance values were monitored at 5-minute intervals for 25 minutes.

The MK2i Peptide (YARAAARQARAKALARQLGVAA [SEQ ID NO: 33]) Significantly Reduces Mean IL-6 and IL-β Concentration Dunnett's method was used to compare the effect of TNF-α+MK2i (YARAAARQARAKALARQLGVAA [SEQ ID NO: 33]) treatment on IL-6 concentration to TNF-α treatment. For the 5 ng/ml and 10 ng/ml TNF-α controls, analysis showed that mean IL-6 concentrations significantly decreased following 0.5 mM, 1 mM, and 3 mM MK2i (YARAAARQARAKALARQLGVAA [SEQ ID NO: 33]) treatment for 4 hours, 8 hours, or 24 hours (FIG. 7, A-C).

Dunnett's method also was used to compare the effect of TNF-α+MK2i (YARAAARQARAKALARQLGVAA [SEQ ID NO: 33]) treatment on IL-1β concentration to TNF-α treatment alone (FIG. 7, D-F). For the 5 ng/ml TNF-α controls, analysis showed that after 4 hours, 8 hours and 24 hours, mean IL-1β concentrations significantly decreased after 0.5 mM, 1 mM, and 3 mM MK2i (YARAAARQARAKALARQLGVAA [SEQ ID NO: 33]) treatment. For the 10 ng/ml TNF-α controls, analysis showed that after 4 hours and 8 hours, mean IL-1β concentrations significantly decreased after 0.5 mM, 1 mM, and 3 mM MK2i (YARAAARQARAKALARQLGVAA [SEQ ID NO: 33]) treatment. After 24 hours, mean IL-1β concentrations also decreased after 0.5 mM, 1 mM, and 3 mM MK2i (YARAAARQARAKALARQLGVAA [SEQ ID NO: 33]) treatment; however, only 3 mM MK2i (YARAAARQARAKALARQLGVAA [SEQ ID NO: 33]) produced a statistically significant decrease. Results suggest that MK2i treatment is an effective method for down-regulating, but not eliminating, cytokine production following microglial activation.

Figure 8:
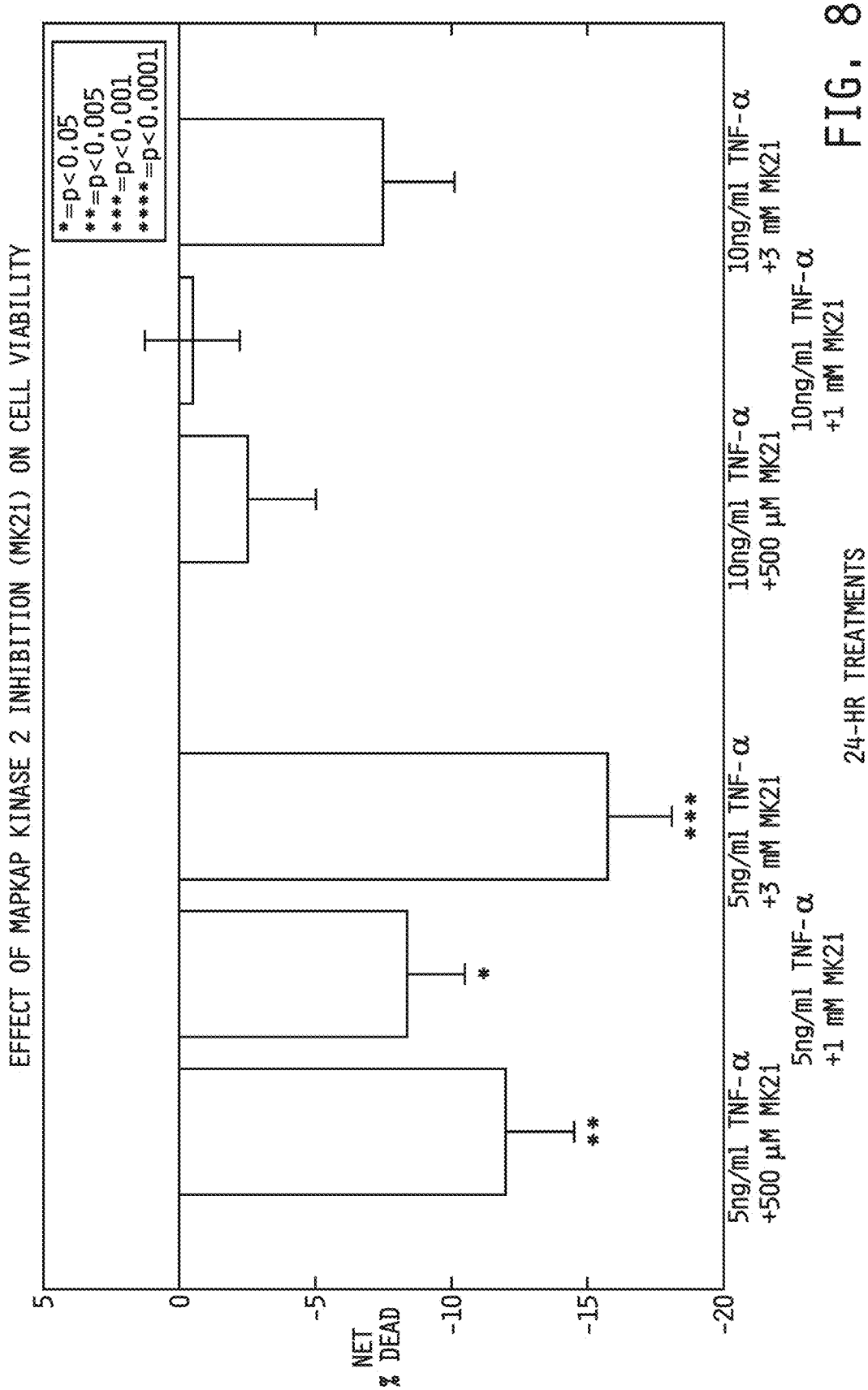
FIG. 8 shows a graph of the net % dead cells versus 24 treatments of 1) 5 ng/ml TNF-α plus 500 μm MK2i (YARAAARQARAKALARQLGVAA [SEQ ID NO: 33]); 2) 5 ng/ml TNF-α plus 1 mM MK2i; 3) 5 ng/ml TNF-α plus 3 mM MK2i; 4) 10 nm/ml TNF-α plus 500 μM MK2i; 5) 10 ng/ml TNF-α plus 1 mM MK2i; and 6) 10 ng/ml TNF-α plus 3 mM MK2i.

Example 5. The Effect of MAPKAP Kinase 2 Inhibition (MK2i) on Cortical Cell Viability Dunnett's method was used to compare the effect of TNF-α+MK2i (YARAAARQARAKALARQLGVAA [SEQ ID NO: 33]) treatment to TNF-α treatment on the percentage of dead cortical cells. FIG. 8 shows a graph of the net % dead cells versus 24 treatments of 1) 5 ng/ml TNF-α plus 500 µm MK2i (YARAAARQARAKALARQLGVAA [SEQ ID NO: 33]); 2) 5 ng/ml TNF-α plus 1 mM MK2i; 3) 5 ng/ml TNF-α plus 3 mM MK2i; 4) 10 nm/ml TNF-α plus 500 µM MK2i; 5) 10 ng/ml TNF-α plus 1 mM MK2i; and 6) 10 ng/ml TNF-α plus 3 mM MK2i. In FIG. 8, % dead values for TNF-α+MK2i (YARAAARQARAKALARQLGVAA [SEQ ID NO: 33]) treatments were normalized to TNF-α only treatments. After 24 hours, 5 ng/ml TNF-α+MK2i (YARAAARQARAKALARQLGVAA [SEQ ID NO: 33]) treatment significantly decreased % dead cells. 10 ng/ml TNF-α+MK2i (YARAAARQARAKALARQLGVAA [SEQ ID NO: 33]) treatment also decreased % dead values. However, this decrease was not statistically significant. FIG. 4 shows a decreased neuronal population when cells are treated with 10 ng/ml TNF-α. This effect was not observed in cultures simultaneously treated with 10 ng/ml TNF-α along with MK2i (both 0.5 mM and 1 mM concentration). This suggests that treatment with MK2i exerts a neuroprotective effect. These results also suggest that MK2i (YARAAARQARAKALARQLGVAA [SEQ ID NO: 33]) treatment creates a more viable cellular environment, potentially through avoiding TNF-α-induced neuroinflammation (see, for example, Lee et al 1999, Oh et al., 1999, Tambuyzer et al., 2009).

Figure 9:
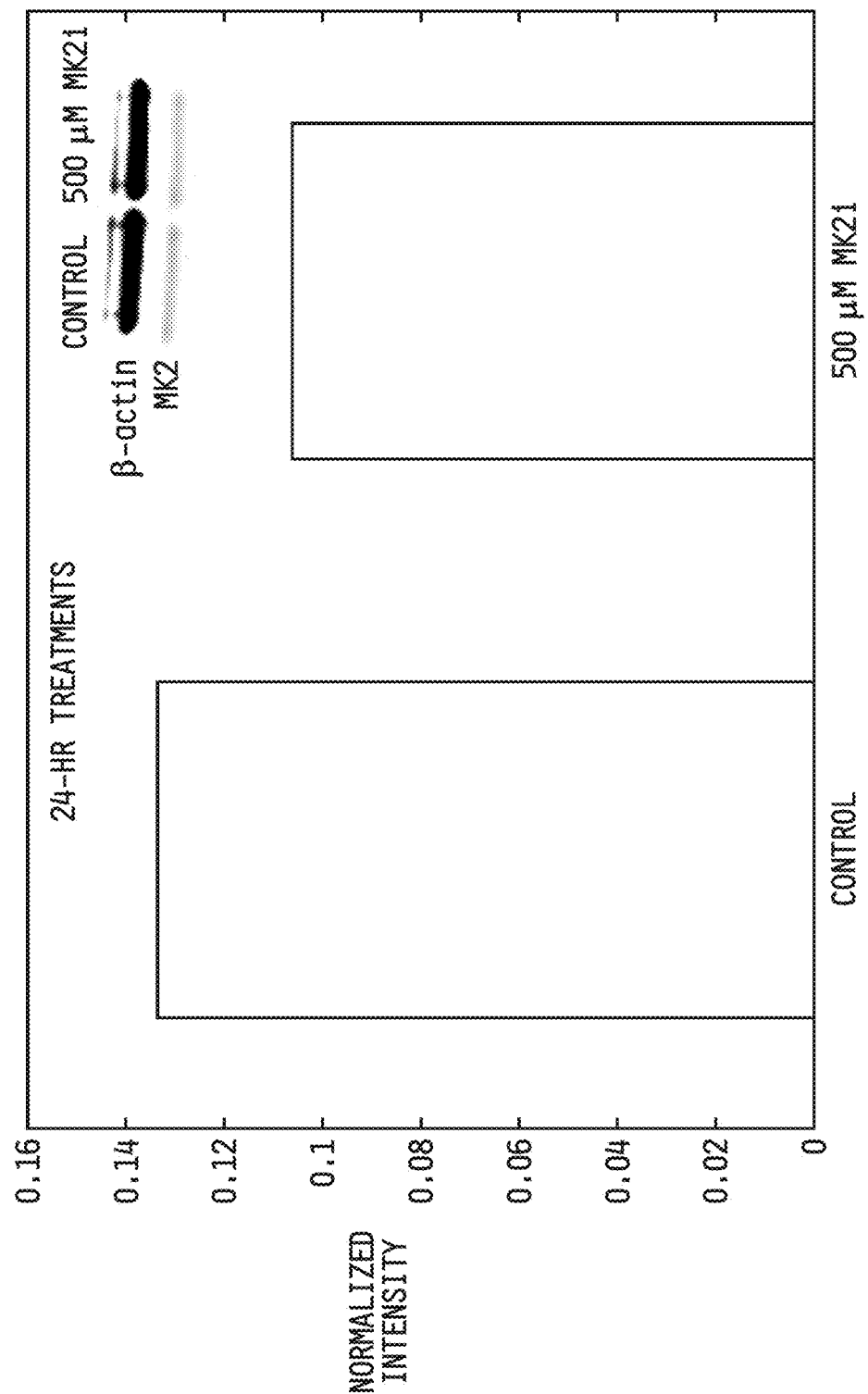
FIG. 9 shows a graph of normalized intensity of the expression level of the MK2 protein by cultured cortical cells following 24 hour MK2i (YARAAARQARAKALAR-QLGVAA [SEQ ID NO: 33]) (500 μM) treatment. The upper right corner of the figure shows a western blot analysis of the MK2 protein following MK2i (500 μM) treatment.

Example 6. The Effect of the MK2i Peptide YARAAARQARAKALARQLGVAA [SEQ ID NO: 33] on MK2 Expression Western blot analysis was used to determine the effect of the MK2i peptide YARAAARQARAKALARQLGVAA [SEQ ID NO: 33] on MK2 expression. FIG. 9 shows a graph of normalized intensity of the expression level of the MK2 protein by cultured cortical cells following 24 hour MK2i (YARAAARQARAKALARQLGVAA [SEQ ID NO: 33]) (500 µM) treatment. The upper right corner of the figure shows a western blot analysis of the MK2 protein following MK2i (500 µM) treatment. Comparison of control blots to treatment blots showed no significant reduction in MK2 expression following 24 hr 0.5 mM MK2i (YARAAAR-QARAKALARQLGVAA [SEQ ID NO: 33]) treatment. These results support MK2i's mechanism of action, i.e., MK2i interferes with substrate binding to MK2, but does not reduce MK2 activity (FIG. 9) or phosphorylation (data not shown).

Example 7. Animal Models

In another aspect, the present invention further describes experiments in animal models of human disease that will be used to determine the effect of the polypeptides of the present invention.
Spinal Cord Models
Spinal cord experiments: Sprague Dawley rats (200-300 mg) will be subjected to spinal cord injury using transection (Widenfalk, Lundstromer et al. 2001). Following halothane anesthesia, dorsal laminectomies at T9 expose the cord. Complete transection leaving a 2 mm gap will be achieved using an iris scalpel. Peptide concentrations ranging from 0.01-1 mM peptide or saline (control) will be applied to the injured cord is achieved using 50-100 µl volumes. Closure will be done using absorbable suture material, and the animals recover on warmed blankets. Prophylactic antibiotics will be administered for one week, and subsequently if needed. Urinary bladders will be emptied thrice daily by mechanical expression for the first week, and twice daily thereafter to prevent urinary tract infections. Animals will be sacrificed at two time points to provide assessment of the onset and sustained regeneration of axons (typically in cohorts of 6 and 16 on days 7 and 56 respectively. The day 7 time allows determination of the extent of proliferation of astrocytes and if there is a chronic immune response. Day 56 will provide information on axonal regeneration (Coumans, J. V., T. T.-S. Lin, et al. (2001). "Axonal regeneration and functional recovery after complete spinal cord transection in rats by delayed treatment with transplants and neurotrophins" The Journal of Neuroscience 21 (23): 9334-9344). A larger number of animals is needed for day 56 animals so that longitudinal and axonal sectioning as well as neuroanatomical tracing can be done (Woerly, Doan Woerly, S., V. D. Doan, et al. (2001). "Spinal cord reconstruction using Neurogel™ Implants and functional recovery after chronic injury." Journal of Neuroscience Research 66: 1187-1197).
Spinal Cord Histology:
Animals will be euthanized by $CO_2$ inhalation according to AVMA recommendations (Andrews, E. J., B. T. Bennett, et al. (1993). "Report of the AVMA panel on Euthanasia." Journal of the American Veterinary Association 202 (2): 229-249). Cardiac perfusion using 2% paraformaldehyde in PBS, followed by 10% sucrose precedes cord dissection to optimize histology (Andrew, D. and A. D. Craig, Spinothalamic lamina I neurons selectively sensitive to histamine: a central neural pathway for itch. Nature Neuroscience, 2001. 4 (1): p. 72-77). From the four animals not receiving neural tracing, the cord in the region of injury will be recovered, then processed by longitudinal cryostat sectioning (14 µm) along the injured axis. For assessment of proliferative cells in the injury site, anti-PCNA antibodies are applied according to supplier's instruction. Cell-type staining for occupation of the matrix in the context of spinal repair will include astrocytes (glial fibrillary acidic protein, GFAP), oligodendrocytes (myelin proteolipid protein, mPLP), neurons (neuron specific enolase, NSE), GAP-43 (found in the growth cone of extending axons), monocytes/macrophages (CD45), lymphocytes (CD16), and endothelial cells (factor VIII).
Cervical Contusion Injury.
A contusion injury will be created using an electromagnetic SCI device. Animals first will be anesthetized and then a vertical incision will be made along the cervical vertebra and the superficial muscle and skin retracted. A laminectomy will be used to expose at cervical vertebra C5 and the spinal cord underneath (C5) while maintaining an intact dura mater. The cervical contusion injury will be created with a force of 3 Kdyn. The exposed C5 spinal cord will be rated as either mildly, moderately or severely injured as determined by displacement of the spinal cord by 0.80 mm, 0.95 mm, or 1.10 mm, respectively, with a single, brief displacement of 20 msec. After injury, the muscles and skin will be sutured in layers. The rats will recover in a warmed cage with water and food easily accessible. Gentamicin (5 mg/kg, intramuscular) will be administered immediately post-surgery and then daily for seven days. The analgesic, Buprenex (0.01 mg/kg of 0.3 mg/mL, subcutaneous) will be delivered post-surgery and daily for 2 days to minimize animal discomfort. The rats will be maintained for 1 week or 9 weeks after injury. For each time point and severity of injury, 20 animals will be treated and 10 animals will serve as controls. Harvested tissues will be examined for cavitation, gliosis and axonal regeneration.

Example 8. Animal Models

Adult Sprague-Dawley rats were anesthetized with intraperitoneal injection of ketamine/xylazine and their dorsal thoracic skin scrubbed with an aseptic betadine solution. A T9-10 laminectomy was performed under sterile conditions to expose the spinal cord without disrupting the dura. FIG. 10 shows a graph of the MPO activity. A moderate spinal cord injury was delivered with a MASCIS impactor (Keck Center for Collaborative Research, Piscataway, N.J.) at a level of 25 cm. Immediately after the surgery the incision was closed in multiple layers. Thirty minutes following injury the animals were dosed with 0.5 ml YARAAAR-QARAKALARQLGVAA [SEQ ID NO: 33] (500 μM, 50 μM, or 5 μM) in 0.9% NaCl. After 4 hours, the animals were sacrificed via a lethal dose of pentobarbital. The injured spinal cord was dissected out. Myeloperoxidase enzyme (MPO) activity was measured. There was a significant reduction in the amount of MPO activity using the 5 M MK2i dose (I.V.) compared to the higher doses and the saline control.

While the present invention has been described with reference to the specific embodiments thereof, it should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for improving or enhancing neurite outgrowth following a nerve injury in a subject in need thereof, the method comprising:
   (a) providing a therapeutic amount of a composition comprising:
      (i) a MAPKAP kinase 2 inhibitor peptide of amino acid sequence YARAAARQARAKALARQLGVAA [SEQ ID NO: 33];
      (ii) a carrier; and
   (b) administering the composition to the subject in need thereof;
   wherein the therapeutic amount is effective
      1. to enhance or improve outgrowth of at least one neurite process from a neuron cell body; and
      2. to increase neurite length by at least 10% relative to neurite length of a neuron that has not been treated with the composition.

2. The method according to claim 1, wherein the composition is a pharmaceutical composition.

3. The method according to claim 1, wherein the neurite process is an axon.

4. The method according to claim 1, wherein the neurite process is a dendrite.

5. The method according to claim 1, wherein the composition inhibits production of at least one inflammatory cytokine following the nerve injury.

6. The method according to claim 5, wherein the at least one inflammatory cytokine is at least one of IL-1 beta, IL-6, and TNF-alpha.

7. The method according to claim 5, wherein the at least one inflammatory cytokine is produced by activated microglia and astrocytes following the nerve injury.

8. The method according to claim 1, wherein the concentration of the MAPKAP kinase 2 inhibitor peptide in the therapeutic composition is from 0.001 nM to less than 3 mM.

9. The method according to claim 1, wherein the composition is in a unit-dosage container or in a multi-dosage container.

10. A method for improving or enhancing nerve regeneration following a nerve injury in a subject in need thereof, the method comprising:
    (a) providing a therapeutic amount of a composition comprising:
       (i) a MAPKAP kinase 2 inhibitor peptide of amino acid sequence of YARAAARQARAKALARQLGVAA [SEQ ID NO: 33];
       (ii) a carrier; and
    (b) administering the composition to the subject in need thereof;
    wherein the therapeutic amount is effective
       1. to enhance or improve outgrowth of at least one neurite process from a neuron cell body; and
       2. to increase regrowth of a neurite process of a neuron by at least 10% in length relative to regrowth of a neurite process of a neuron that has not been treated with the composition.

11. The method according to claim 10, wherein the composition increases neurite regrowth by inhibiting expression of at least on inflammatory cytokine from activated microglia.

12. The method according to claim 11, wherein the at least one inflammatory cytokine is at least one of IL-1 beta, IL-6, and TNF-alpha.

13. The method according to claim 11, wherein the at least one inflammatory cytokine is produced by activated microglia and astrocytes following nerve injury.

14. The method according to claim 10, wherein the concentration of the MAPKAP kinase 2 inhibitor peptide in the therapeutic composition is from 0.001 nM to less than 3 mM.

15. A method for protecting against progression of a neuronal injury in a subject in need thereof, the method comprising:

(a) providing a therapeutic amount of a composition comprising:
   (i) a MAPKAP kinase 2 inhibitor peptide of amino acid sequence of YARAAARQARAKALARQLGVAA [SEQ ID NO: 33]; and
   (ii) a carrier; and
(b) administering the composition to the subject in need thereof;
wherein the therapeutic amount is effective
   1. to enhance or improve outgrowth of at least one neurite process form a neuron cell body;
   2. to reduce or inhibit at least one manifestation of progression of the neuronal injury in at least one neuronal cell population affected by the neuronal injury; and
   3. to increase survival of the at least one neuronal cell population affected by the neuronal injury.

16. The method according to claim 15, wherein the neuronal injury is a neurapraxia type injury.

17. The method according to claim 15, wherein the injury is an axonotmesis type injury.

18. The method according to claim 15, wherein the injury is a neurotmesis type injury.

19. The method according to claim 15, wherein the injury results from an acute disorder.

20. The method according to claim 19, wherein the acute disorder is a stroke, a spinal cord injury, or a traumatic brain injury.

21. The method according to claim 15, wherein the at least one manifestation of progression of the neuronal injury in at least one neuronal cell population is apoptotic cell death.

22. The method according to claim 15, wherein the at least one manifestation of progression of the neuronal injury in at least one neuronal cell population is microglial activation.

23. The method according to claim 15, wherein the at least one manifestation of progression of the neuronal injury in at least one neuronal cell population is inflammation.

24. The method according to claim 15, wherein the at least one manifestation of progression of the neuronal injury in at least one neuronal cell population is formation of a scar.

25. The method according to claim 15, wherein the neuronal cell population is a cortical cell population.

26. The method according to claim 15, wherein the neuronal cell population is a mixed cortical cell population.

27. The method according to claim 26, wherein the mixed cortical cell population comprises neurons, microglia, and astrocytes.

28. The method according to claim 15, wherein the composition protects at least one neuron from progression of a neuronal injury by inhibiting expression of at least one inflammatory cytokine from activated microglia.

29. The method according to claim 28, wherein the at least one inflammatory cytokine is at least one of IL-1 beta, IL-6, and TNF-alpha.

* * * * *